US007052850B2

(12) United States Patent
Munroe et al.

(10) Patent No.: US 7,052,850 B2
(45) Date of Patent: May 30, 2006

(54) ISOLATED HUMAN EDG-4 RECEPTOR

(75) Inventors: Donald G. Munroe, Waterdown (CA); Rajender Kamboj, Mississauga (CA); Diana Peters, Toronto (CA); Fatemeh Kooshesh, Etobicoke (CA); Tejal B. Vyas, Mississauga (CA); Ashwani K. Gupta, Mississauga (CA)

(73) Assignee: NPS Allelix Corp., Mississauga (CA)

( * ) Notice: Subject to any disclaimer, the term of this patent is extended or adjusted under 35 U.S.C. 154(b) by 170 days.

(21) Appl. No.: 10/084,507

(22) Filed: Feb. 28, 2002

(65) Prior Publication Data

US 2003/0054452 A1 Mar. 20, 2003

Related U.S. Application Data

(63) Continuation of application No. 09/222,995, filed on Dec. 30, 1998, now abandoned.

(60) Provisional application No. 60/109,885, filed on Nov. 25, 1998, provisional application No. 60/080,610, filed on Apr. 3, 1998, provisional application No. 60/070,185, filed on Dec. 30, 1997.

(51) Int. Cl.
*G01N 33/53* (2006.01)
*G01N 33/566* (2006.01)
*C12N 5/00* (2006.01)
*C12N 15/00* (2006.01)
*C07K 14/705* (2006.01)

(52) U.S. Cl. .................. 435/7.1; 435/69.1; 435/325; 530/350; 436/501

(58) Field of Classification Search ................ 435/7.1, 435/7.2, 69.1, 325; 530/350
See application file for complete search history.

(56) References Cited

U.S. PATENT DOCUMENTS

| 5,585,476 A | 12/1996 | MacLennan |
| 5,856,443 A | 1/1999 | MacLennan |

FOREIGN PATENT DOCUMENTS

| WO | WO 97/00952 | 1/1997 |
| WO | WO 98/53062 | 11/1998 |
| WO | WO 99/54351 | 10/1999 |

OTHER PUBLICATIONS

Hecht et al. Ventricular Zone Gene-1 (vzg-1) Encodes a Lysophosphatidic Acid Receptor Expresses in Neurogenic Regions of the Developing Cerebral Cortex. The Journal of Cell Biology vol. 135/4 1071-1083, (1996).*
AF034780 - GenBank Database Entry, MacLennan et al., from Mol. Cell. Neurosci. 5(3), 201-209 (1994).
AA804628 - GenBank Database Entry, NCI Cancer Genome Anatomy Project (1997).
RNU10699 - GenBank Database Entry, Okazaki et al., from Biochem. Biophys. Res. Commun. 190, 1104-1109 (1993).
AA827835 - GenBank Database Entry, NCI Cancer Genome Anatomy Project (1997).
AA834537 - GenBank Database Entry, NCI Cancer Genome Anatomy Project (1997).
AA767046 - GenBank Database Entry, NCI Cancer Genome Anatomy Project (1997).
N93714 - GenBank Database Entry, Hillier et al., from Genome Res. 6 (9), 807-828 (1996).
Shahrestanifar, et al., "Lysophosphatidic Acid Activates NF-κB in Fibroblasts", The Journal of Biological Chemistry, vol. 274, No. 6, pp 3828-3833 (1999).
Yamaguchi, et al., "Molecular Cloning of the Novel Human G Protein-Coupled Receptor (GPCR) Gene Mapped on Chromosome 9", Biochemical and Biophysical Research Communication, 227, pp. 608-614 (1996).
Maclennan, et al., "Cloning and Characterization of a Putative G-Protein Coupled Receptor Potentially Involved in Development", Molecular and Cellular Neurosciences, 5:pp 201-209 (1994).
An, et al., "Molecular Cloning of the Human Edg 2 Protein and Its Identification as a Functional Cellular Receptor for Lysophosphatidic Acid", Biochemical and Biophysical Research Communications 231, pp 619-622 (1997).
Shatrov, et al., "Sphingosine-1-phosphate Mobilizes Intracellular Calcium and Activates Transcription Factor NF-κB in U937 Cells", Biochemical and Biophysical Research Communications, 234, pp. 121-124 (1997).
Well, JA "Additivity of Mutational Effects in Proteins", Biochemistry 29:8509-8517 (1990).
Ngo et al., "Computational Complexity, Protein Structure Prediction and the Levinthal Paradox", The Protein Folding Problem and Tertiary Structure Prediction, 492-495 Birkhauser Boston (1994).
Bork P., "Powers and Pitfalls in Sequence Analysis: The 70% Hurdle" Genome Research 10:398-400 (2000).
Skolnick et al., "From genes to protein structure and function: novel applications of computational approaches in the genomic era", Trends in Biotech 18(1): 34-39 (2000).

* cited by examiner

*Primary Examiner*—Joseph Murphy
*Assistant Examiner*—Regina M. DeBerry
(74) *Attorney, Agent, or Firm*—Rothwell, Figg, Ernst&Manbeck, P.C.

(57) ABSTRACT

A novel, isolated EDG receptor that upon activation results in increased induction of IL-8 or NF-κB. Preferably, the EDG receptor is a human EDG-4 receptor, which has an amino acid sequence shown in FIGS. 16A and 16B, or a variant of these sequences having at least 91% sequence identity.

18 Claims, 36 Drawing Sheets

FIGURE 14

```
            1                                                          50
AA834537    -------AAA GCCCCATGGC CCCAGCAGGC CTCTGAGCCC CACCATGGGC
AA804628    -------AAA GCCCCATGGC CCCAGCAGGC CTCTGAGCCC CACCATGGGC
AA827835    AGTTCTGAAA GCCCCATGGC CCCAGCAGGC CTCTGAGCCC CACCATGGGC 51                                                         100
AA834537    AGCTTGTACT CGGAGTACCT GAACCCCAAC AAGGTCCAGG AACACTATAA
AA804628    AGCTTGTACT CGGAGTACCT GAACCCCAAC AAGGTCCAGG AACACTATAA
AA827835    AGCTTGTACT CGGAGTACCT GAACCCCAAC AAGGTCCAGG AACACTATAA 101                                                        150
AA834537    TTATACCAAG GAGACGCTGG AAACGCAGGA GACGACCTCC CGCCAGGTGG
AA804628    TTATACCAAG GAGACGCTGG AAACGCAGGA GACGACCTCC CGCCAGGTGG
AA827835    TTATACCAAG GAGACGCTGG AAACGCAGGA GACGACCTCC CGCCAGGTGG 151                                                        200
AA834537    CCTCGGCATT CATCGTCATC CTCTGTTGCG CCATTGTGGT GGAAAACCTT
AA804628    CCTCGGCCTT CATCGTCATC CTCTGTTGCG CCATTGTGGT GGAAAACCTT
AA827835    GCTCGGCCTT CATCGTCATC CTCTGTTGCG CCATTGTGGT GGAAAACCTT 201                                                        250
AA834537    CTGGTGCTCA TTGCGGTGGC CCGAAACAGC AAGTTCCACT CGGCAATGTA
AA804628    CTGGTGCTCA TTGCGGTGGC CCGAAACAGC AAGTTCCACT CGGCAATGTA
AA827835    CTGGTGCTCA TTGCGGTGGC CCGAAACAGC AAGTTCCACT CGGCAATGTA 251                                                        300
AA834537    CCTGTTTCTG GGCAACCTGG CCGCCTCCGA TCTACTGGCA GGCGTGGCCT
AA804628    CCTGTTTCTG GGCAACCTGG CCGCCTCCGA TCTACTGGCA GGCGTGGCCT
AA827835    CCTGTTTCTG GGCAACCTGG CCGCCTCCGA TCTACTGGCA GGCGTGG.CT 301                                                        350
AA834537    TCGTAGCCAA TACCTTGCTC TCTGGCTCTG TCACGCTGAG GCTGACGCCT
AA804628    TCGTAGCCAA TACCTTGCTC TCTGGCTCTG TCACGCTGAG GCTGACGCCT
AA827835    TCGTAGCCAA TACCTTGCTC TCTGGCTCTG TCACGCTGAG GCTGACGCCT 351                                                        400
AA834537    GTGCAGTGGT TTGCCCGGGA CGGTCTGCCT TCATCACGCT CTCGGCCTCT
AA804628    GTGCAGTGGT TTGCCCGGGA C--------- ---------- ----------
AA827835    GTGCAGTGGT TTGCCCGGGA ---------- ---------- ----------

401                                                        450
AA834537    GTCTTCAGCC TCCTGGCCAT CGCCATTGAG CGCCACGTGG CCATTGCAAA
AA804628    ---------- ---------- ---------- ---------- ----------
AA827835    ---------- ---------- ---------- ---------- ----------

```
                                                    M  G  S  L  Y  S  E  Y
   AAAGCCCCATGGCCCCAGCAGGCCTCTGAGCCCCACCATGGGCAGCTTGTACTCGGAGTA
 1 ------------+---------+---------+---------+---------+---------+  60
   TTTCGGGGTACCGGGGTCGTCCGGAGACTCGGGGTGGTACCCGTCGAACATGAGCCTCAT

L  N  P  N  K  V  Q  E  E  Y  N  Y  T  K  E  T  L  E  T  Q
   CCTGAACCCCAACAAGGTCCAGGAACACTATAATTATACCAAGGAGACGCTGGAAACGCA
61 ------------+---------+---------+---------+---------+---------+ 120
   GGACTTGGGGTTGTTCCAGGTCCTTGTGATATTAATATGGTTCCTCTGCGACCTTTGCGT

E  T  T  S  R  Q  V  A  S  A  F  I  V  I  L  C  C  A  I  V
   GGAGACGACCTCCCGCCAGGTGGCCTCGGCCTTCATCGTCATCCTCTGTTGCGCCATTGT
121 -----------+---------+---------+---------+---------+---------+ 180
   CCTCTGCTGGAGGGCGGTCCACCGGAGCCGGAAGTAGCAGTAGGAGACAACGCGGTAACA

V  E  N  L  L  V  L  I  A  V  A  R  N  S  K  F  H  S  A  M
   GGTGGAAAACCTTCTGGTGCTCATTGCGGTGGCCCGAAACAGCAAGTTCCACTCGGCAAT
181 -----------+---------+---------+---------+---------+---------+ 240
   CCACCTTTTGGAAGACCACGAGTAACGCCACCGGGCTTTGTCGTTCAAGGTGAGCCGTTA

Y  L  F  L  G  N  L  A  A  S  D  L  L  A  G  V  A  F  V  A
   GTACCTGTTTCTGGGCAACCTGGCCGCCTCCGATCTACTGGCAGGCGTGGCCTTCGTAGC
241 -----------+---------+---------+---------+---------+---------+ 300
   CATGGACAAAGACCCGTTGGACCGGCGGAGGCTAGATGACCGTCCGCACCGGAAGCATCG

N  T  L  L  S  G  S  V  T  L  R  L  T  P  V  Q  W  F  A  R
   CAATACCTTGCTCTCTGGCTCTGTCACGCTGAGGCTGACGCCTGTGCAGTGGTTTGCCCG
301 -----------+---------+---------+---------+---------+---------+ 360
   GTTATGGAACGAGAGACCGAGACAGTGCGACTCCGACTGCGGACACGTCACCAAACGGGC

E  G  S  A  F  I  T  L  S  A  S  V  F  S  L  L  A  I  A  I
   GGAGGGCTCTGCCTTCATCACGCTCTCGGCCTCTGTCTTCAGCCTCCTGGCCATCGCCAT
361 -----------+---------+---------+---------+---------+---------+ 420
   CCTCCCGAGACGGAAGTAGTGCGAGAGCCGGAGACAGAAGTCGGAGGACCGGTAGCGGTA

E  R  H  V  A  I  A  K  V  K  L  Y  G  S  D  K  S  C  R  M
   TGAGCGCCACGTGGCCATTGCCAAGGTCAAGCTGTATGGCAGCGACAAGAGCTGCCGCAT
421 -----------+---------+---------+---------+---------+---------+ 480
   ACTCGCGGTGCACCGGTAACGGTTCCAGTTCGACATACCGTCGCTGTTCTCGACGGCGTA

L  L  L  I  G  A  S  W  L  I  S  L  V  G  G  L  P  I  L
   GCTTCTGCTCATCGGGGCCTCGTGGCTCATCTCGCTGGTCCTCGGTGGCCTGCCCATCCT
481 -----------+---------+---------+---------+---------+---------+ 540
   CGAAGACGAGTAGCCCCGGAGCACCGAGTAGAGCGACCAGGAGCCACCGGACGGGTAGGA

G  W  N  C  L  G  E  L  E  A  C  S  T  V  L  P  L  Y  A  K
   TGGCTGGAACTGCCTGGGCCACCTCGAGGCCTGCTCCACTGTCCTGCCTCTCTACGCCAA
541 -----------+---------+---------+---------+---------+---------+ 600
   ACCGACCTTGACGGACCCGGTGGAGCTCCGGACGAGGTGACAGGACGGAGAGATGCGGTT

H  Y  V  L  C  V  V  T  I  F  S  I  I  L  L  A  I  V  A  L
   GCATTATGTGCTGTGCGTGGTGACCATCTTCTCCATCATCCTGTTGGCCATCGTGGCCCT
601 -----------+---------+---------+---------+---------+---------+ 660
   CGTAATACACGACACGCACCACTGGTAGAAGAGGTAGTAGGACAACCGGTAGCACCGGGA
```

Fig.15A-2

```
        Y  V  R  I  Y  C  V  V  R  S  S  H  A  D  M  A  A  P  Q  T
       GTACGTGCGCATCTACTGCGTGGTCCGCTCAAGCCACGCTGACATGGCCGCCCCGCAGAC
661    ------------+---------+---------+---------+---------+---------+  720
       CATGCACGCGTAGATGACGCACCAGGCGAGTTCGGTGCGACTGTACCGGCGGGGCGTCTG

L  A  L  L  K  T  V  T  I  V  L  G  V  F  I  V  C  W  L  P
       GCTAGCCCTGCTCAAGACGGTCACCATCGTGCTAGGCGTCTTTATCGTCTGCTGGCTGCC
721    ------------+---------+---------+---------+---------+---------+  780
       CGATCGGGACGAGTTCTGCCAGTGGTAGCACGATCCGCAGAAATAGCAGACGACCGACGG

A  F  S  I  L  L  L  D  Y  A  C  P  V  H  S  C  P  I  L  Y
       CGCCTTCAGCATCCTCCTTCTGGACTATGCCTGTCCCGTCCACTCCTGCCCGATCCTCTA
781    ------------+---------+---------+---------+---------+---------+  840
       GCGGAAGTCGTAGGAGGAAGACCTGATACGGACAGGGCAGGTGAGGACGGGCTAGGAGAT

K  A  H  Y  X  F  A  V  S  T  L  N  S  L  L  N  P  V  I  Y
       CAAAGCCCACTACTTTTTCGCCGTCTCCACCCTGAATTCCCTGCTCAACCCCGTCATCTA
841    ------------+---------+---------+---------+---------+---------+  900
       GTTTCGGGTGATGAAAAAGCGGCAGAGGTGGGACTTAAGGGACGAGTTGGGGCAGTAGAT

T  W  R  S  R  D  L  R  R  E  V  L  R  P  L  Q  C  W  R  P
       CACGTGGCGCAGCCGGGACCTGCGGCGGGAGGTGCTTCGGCCGCTGCAGTGCTGGCGGCC
901    ------------+---------+---------+---------+---------+---------+  960
       GTGCACCGCGTCGGCCCTGGACGCCGCCCTCCACGAAGCCGGCGACGTNACGACCGCCGG

G  V  G  V  Q  G  R  R  R  G  G  T  P  G  H  L  L  P  L
       GGGGGTGGGGGTGCAAGGACGGAGGCGGGGCGGGACCCCGGGCCACCACCTCCTGCCACT
961    ------------+---------+---------+---------+---------+---------+  1020
       CCCCCACCCCCACGTTCCTGCCTCCGCCCCGCCCTGGGGCCCGGTGGTGGAGGACGGTGA

R  S  S  S  S  L  E  R  G  M  H  M  P  T  S  P  T  F  L  E
       CCGCAGCTCCAGCTCCCTGGAGAGGGGCATGCACATGCCCACGTCACCCACGTTTCTGGA
1021   ------------+---------+---------+---------+---------+---------+  1080
       GGCGTCGAGGTCGAGGGACCTCTCCCCGTACGTGTACGGGTGCAGTGGGTGAAAGACCT

G  N  T  V  V  *
       GGGCAACACGGTGGTCTGAGGGTGGGGGTGGACCAACAACCAGGCCAGGGCATAGGGGTT
1081   ------------+---------+---------+---------+---------+---------+  1140
       CCCGTTGTGCCACCAGACTCCCACCCCCACCTGGTTGTTGGTCCGGTCCCGTATCCCCAA

CATGGAAAGGCCACTGGGTGACCCCAAATA
1141   ------------+---------+---------+  1170
       GTACCTTTCCGGTGACCCACTGGGGTTTAT
```

Fig.15B-1 cDNA sequence of clone pC3-hedg4#36 encoding functional HEDG4 receptor protein.

```
        ATGGGCAGCTTGTACTCGGAGTACCTGAACCCCAACAAGGTCCAGGAACACTATAATTAT
  1     ---------+---------+---------+---------+---------+---------+    60
        TACCCGTCGAACATGAGCCTCATGGACTTGGGGTTGTTCCAGGTCCTTGTGATATTAATA

ACCAAGGAGACGCTGGAAACGCAGGAGACGACCTCCCGCCAGGTGGCCTCGGCCTTCATC
 61     ---------+---------+---------+---------+---------+---------+   120
        TGGTTCCTCTGCGACCTTTGCGTCCTCTGCTGGAGGGCGGTCCACCGGAGCCGGAAGTAG

GTCATCCTCTGTTGCGCCATTGTGGTGGAAAAACCTTCTGGTGCTCATTGCGGTGGCCCGA
121     ---------+---------+---------+---------+---------+---------+   180
        CAGTAGGAGACAACGCGGTAACACCACCTTTTGGAAGACCACGAGTAACGCCACCGGGCT

AACAGCAAGTTCCACTCGGCAATGTACCTGTTTCTGGGCAACCTGGCCGCCTCCGATCTA
181     ---------+---------+---------+---------+---------+---------+   240
        TTGTCGTTCAAGGTGAGCCGTTACATGGACAAAGACCCGTTGGACCGGCGGAGGCTAGAT

CTGGCAGGCGTGGCCTTCGTAGCCAATACCTTGCTCTCTGGCTGTGTCACGCTGAGGCTG
241     ---------+---------+---------+---------+---------+---------+   300
        GACCGTCCGCACCGGAAGCATCGGTTATGGAACGAGAGACCGAGACAGTGCGACTCCGAC

ACGCCTGTGCAGTGGTTTGCCCGGGAGGGCTCTGCCTTCATCACGCTCTCGGCCTCTGTC
301     ---------+---------+---------+---------+---------+---------+   360
        TGCGGACACGTCACCAAACGGGCCCTCCCGAGACGGAAGTAGTGCGAGAGCCGGAGACAG

TTCAGCCTCCTGGCCATCGCCATTGAGCGCCACGTGGCCATTGCCAAGGTCAAGCTGTAT
361     ---------+---------+---------+---------+---------+---------+   420
        AAGTCGGAGGACCGGTAGCGGTAACTCGCGGTGCACCGGTAACGGTTCCAGTTCGACATA

GGCAGCGACAAGAGCTGCCGCATGCTTCTGCTCATCGGGGCCTCGTGGCTCATCTCGCTG
421     ---------+---------+---------+---------+---------+---------+   480
        CCGTCGCTGTTCTCGACGGCGTACGAAGACGAGTAGCCCCGGAGCACCGAGTAGAGCGAC

GTCCTCGGTGGCCTGCCCATCCTTGGCTGGAACTGCCTGGGCCACCTCGAGGCCTGCTCC
481     ---------+---------+---------+---------+---------+---------+   540
        CAGGAGCCACCGGACGGGTAGGAACCGACCTTGACGGACCCGGTGGAGCTCCGGACGAGG

ACTGTCCTGCCTCTCTACGCCAAGCATTATGTGCTGTGCGTGGTGACCATCTTCTCCATC
541     ---------+---------+---------+---------+---------+---------+   600
        TGACAGGACGGAGAGATGCGGTTCGTAATACACGACACGCACCACTGGTAGAAGAGGTAG

ATCCTGTTGGCCGTCGTGGCCCTGTACGTGCGCATCTACTGCGTGGTCCGCTCAAGCCAC
601     ---------+---------+---------+---------+---------+---------+   660
        TAGGACAACCGGCAGCACCGGGACATGCACGCGTAGATGACGCACCAGGCGAGTTCGGTG

GCTGACATGGCCGCCCCGCAGACGCTAGCCCTGCTCAAGACGGTCACCATCGTGCTAGGC
661     ---------+---------+---------+---------+---------+---------+   720
        CGACTGTACCGGCGGGGCGTCTGCGATCGGGACGAGTTCTGCCAGTGGTAGCACGATCCG

GTCTTTATCGTCTGCTGGCTGCCCGCCTTCAGCATCCTCCTTCTGGACTATGCCTGTCCC
721     ---------+---------+---------+---------+---------+---------+   780
```

Fig.15B-2

```
         CAGAAATAGCAGACGACCGACGGGCGGAAGTCGTAGGAGGAAGACCTGATACGGACAGGG

GTCCACTCCTGCCCGATCCTCTACAAAGCCCACTACCTTTTCGCCGTCTCCACCCTGAAT
781      ---------+---------+---------+---------+---------+---------+   840
         CAGGTGAGGACGGGCTAGGAGATGTTTCGGGTGATGGAAAAGCGGCAGAGGTGGGACTTA

TCCCTGCTCAACCCCGTCATCTACACGTGGCGCAGCCGGGACCTGCGGCGGGAGGTGCTT
841      ---------+---------+---------+---------+---------+---------+   900
         AGGGACGAGTTGGGGCAGTAGATGTGCACCGCGTCGGCCCTGGACGCCGCCCTCCACGAA

CGGCCGCTGCAGTGCTGGCGGCCGGGGTGGGGGTGCAAGGACGGAGGCGGGCGGGACC
901      ---------+---------+---------+---------+---------+---------+   960
         GCCGGCGACGTCACGACCGCCGGCCCCACCCCCACGTTCCTGCCTCCGCCCCGCCCTGG

CCGGGCCACCACCTCCTGCCACTCCGCAGCTCCAGCTCCCTGGAGAGGGGCATGCACATG
961      ---------+---------+---------+---------+---------+---------+   1020
         GGCCCGGTGGTGGAGGACGGTGAGGCGTCGAGGTCGAGGGACCTCTCCCCGTACGTGTAC

CCCACGTCACCCACGTTTCTGGAGGGCAACACGGTGGTCTGA
1021     ---------+---------+---------+---------+--   1062
         GGGTGCAGTGGGTGCAAAGACCTCCCGTTGTGCCACCAGACT
```

FIGURE 16 A

```
  1  MGSLYSEYLN PNKVQEHYNY TKETLETQET TSRQVASAFI VILCCAIVVE

51  NLLVLIAVAR NSKFHSAMYL FLGNLAASDL LAGVAFVANT LLSGSVTLRL

101  TPVQWFAREG SAFITLSASV FSLLAIAIER HVAIAKVKLY GSDKSCRMLL

151  LIGASWLISL VLGGLPILGW NCLGHLEACS TVLPLYAKHY VLCVVTIFSI

201  ILLAIVALYV RIYCVVRSSH ADMAAPQTLA LLKTVTIVLG VFIVCWLPAF

251  SILLLDYACP VHSCPILYKA HYXFAVSTLN SLLNPVIYTW RSRDLRREVL

301  RPLQCWRPGV GVQGRRRGGT PGHHLLPLRS SSSLERGMHM PTSPTFLEGN

351  TVV*
```

Conserved features of G-protein coupled receptors include:
    N-terminal extracellular domain:  Residues 1 - 36
    TM-I:  Residues 37 - 57
    Intracellular loop 1:  Residues 58 - 68
    TM-II:  Residues 69 - 92
    Extracellular loop 1:  Residues 93 - 111
    TM-III:  Residues 112 - 130
    Intracellular loop 2:  Residues 131 - 149
    TM-IV:  Residues 150 - 168
    Extracellular loop 2:  Residues 169 - 185
    TM-V:  Residues 186 - 210
    Intracellular loop 3:  Residues 211 - 232
    TM-VI:  Residues 233 - 254
    Extracellular loop 3:  Residues 255 - 266
    TM-VII:  Residues 267 - 285
    C-terminal cytoplasmic domain:  Residues 286 - 353

Potential post-transcriptional modification sites:
    N-glycosylation:  Residues 19
    Phosphorylation:  Residues 142, 145, 219, 289, 332, 345
    Myristylation:  Residues 141, 318

Figure 16B

Predicted amino acid sequence of HEDG4 polypeptide encoded by pC3-hedg4#36.

```
  1  MGSLYSEYLN  PNKVQEHYNY  TKETLETQET  TSRQVASAFI  VILCCAIVVE

51  NLLVLIAVAR  NSKFHSAMYL  FLGNLAASDL  LAGVAFVANT  LLSGSVTLRL

101  TPVQWFAREG  SAFITLSASV  FSLLAIAIER  HVAIAKVKLY  GSDKSCRMLL

151  LIGASWLISL  VLGGLPILGW  NCLGHLEACS  TVLPLYAKHY  VLCVVTIFSI

201  ILLAVVALYV  RIYCVVRSSH  ADMAAPQTLA  LLKTVTIVLG  VFIVCWLPAF

251  SILLLDYACP  VHSCPILYKA  HYLFAVSTLN  SLLNPVIYTW  RSRDLRREVL

301  RPLQCWRPGV  GVQGRRRGGT  PGHHLLPLRS  SSSLERGMHM  PTSPTFLEGN

351  TVV
```

FIGURE 17 A

```
Human    1 MGSLYSEYLNPNKVQEHYNYTKETLETQETTSRQVASAFIVILCCAIVVE  50
           || ||·||||||  ||||||||||||||: ||| ||·||||||:||||||||
Rat      1 MGGLYSEYLNPEKVQEHYNYTKETLDMQETPSRKVASAFIIILCCAIVVE  50

Human   51 NLLVLIAVARNSKFHSAMYLFLGNLAASDLLAGVAFVANTLLSGSVTLRL 100
           |||||||||||||||||||||||||||||||||||||||||||| ||| |
Rat     51 NLLVLIAVARNSKFHSAMYLFLGNLAASDLLAGVAFVANTLLSGPVTLSL 100

Human  101 TPVQWFAREGSAFITLSASVFSLLAIAIERHVAIAKVKLYGSDKSCRMLL 150
           ||·||||||||||||||||||||||||||| ||||||||||||||||||:
Rat    101 TPLQWFAREGSAFITLSASVFSLLAIAIERQVAIAKVKLYGSDKSCRMLM 150

Human  151 LIGASWLISLVLGGLPILGWNCLGHLEACSTVLPLYAKHYVLCVVTIFSI 200
           |||||||||:|||||||||||||·||||||||||||||||||||||||:
Rat    151 LIGASWLISLILGGLPILGWNCLDHLEACSTVLPLYAKHYVLCVVTIFSV 200

Human  201 ILLAIVALYVRIYCVVRSSHADMAAPQTLALLKTVTIVLGVFIVCWLPAF 250
           |||||||||||||| ||||||||·| ||||||||||||||||:||||||
Rat    201 ILLAIVALYVRIYFVVRSSHADVAGPQTLALLKTVTIVLGVFIICWLPAF 250

Human  251 SILLLDYACPVHSCPILYKAHYXFAVSTLNSLLNPVIYTWRSRDLRREVL 300
           ||||||  ||| ·||:|||||| ||·||||||||||||||||||||||||
Rat    251 SILLLDSTCPVRACPVLYKAHYFFAFATLNSLLNPVIYTWRSRDLRREVL 300

Human  301 RPLQCWRPGVGVQGRRRGGTPGHHLLPLRSSSSLERGMHMPTSPTFLEGN 350
           ||| ||| | |  |  ||||  ||| |||||||||||||:|||||||||||
Rat    301 RPLLCWRQGKGATG.RRGGNPGHRLLPLRSSSSLERGLHMPTSPTFLEGN 349

Human  351 TVV* 353
           |||
Rat    350 TVV* 352
```

Figure 17B

Alignment of HEDG4 with pC3-hedg4#36 translation product and rat H218 (REDG4). Differences between pC3-hedg4#36 translation product and previously determined HEDG4 polypeptide are indicated in reverse text. Differences between rat and human edg-4 polypeptide sequences are shown in bold, shaded text.

```
                 1                                                    50
      HEDG4     MGSLYSEYLN PNKVQEHYNY TKETLETQET TSRQVASAFI VILCCAIVVE
      HEDG4#36  MGSLYSEYLN PNKVQEHYNY TKETLETQET TSRQVASAFI VILCCAIVVE
      REDG4     MGGLYSEYLN PEKVQEHYNY TKETLDMQET PSRKVASAFI IILCCAIVVE 51                                                   100
      HEDG4     NLLVLIAVAR NSKFHSAMYL FLGNLAASDL LAGVAFVANT LLSGSVTLRL
      HEDG4#36  NLLVLIAVAR NSKFHSAMYL FLGNLAASDL LAGVAFVANT LLSGSVTLRL
      REDG4     NLLVLIAVAR NSKFHSAMYL FLGNLAASDL LAGVAFVANT LLSGPVTLSL 101                                                  150
      HEDG4     TPVQWFAREG SAFITLSASV FSLLAIAIER HVAIAKVKLY GSDKSCRMLL
      HEDG4#36  TPVQWFAREG SAFITLSASV FSLLAIAIER HVAIAKVKLY GSDKSCRMLL
      REDG4     TPLQWFAREG SAFITLSASV FSLLAIAIER QVAIAKVKLY GSDKSCRMLM 151                                                  200
      HEDG4     LIGASWLISL VLGGLPILGW NCLGHLEACS TVLPLYAKHY VLCVVTIFSI
      HEDG4#36  LIGASWLISL VLGGLPILGW NCLGHLEACS TVLPLYAKHY VLCVVTIFSI
      REDG4     LIGASWLISL ILGGLPILGW NCLDHLEACS TVLPLYAKHY VLCVVTIFSV 201                                                  250
      HEDG4     ILLAVVALYV RIYCVVRSSH ADMAAPQTLA LLKTVTIVLG VFIVCWLPAF
      HEDG4#36  ILLAVVALYV RIYCVVRSSH ADMAAPQTLA LLKTVTIVLG VFIVCWLPAF
      REDG4     ILLAIVALYV RIYFVVRSSH ADVAGPQTLA LLKTVTIVLG VFIICWLPAF 251                                                  300
      HEDG4     SILLLDYACP VHSCPILYKA HYXFAVSTLN SLLNPVIYTW RSRDLRREVL
      HEDG4#36  SILLLDYACP VHSCPILYKA HYLFAVSTLN SLLNPVIYTW RSRDLRREVL
      REDG4     SILLLDSTCP VRACPVLYKA HYFFAFATLN SLLNPVIYTW RSRDLRREVL 301                                                  350
      HEDG4     RPLQCWRPGV GVQGRRRGGT PGHHLLPLRS SSSLERGMHM PTSPTFLEGN
      HEDG4#36  RPLQCWRPGV GVQGRRRGGT PGHHLLPLRS SSSLERGMHM PTSPTFLEGN
      REDG4     RPLLCWRQGK GATG.RRGGN PGHRLLPLRS SSSLERGLHM PTSPTFLEGN

351
      HEDG4     TVV-
      HEDG4#36  TVV-
      REDG4     TVV-
```

Figure 21. Human Edg-6 Amino Acid Sequence.

```
      MVIMGQCYYNETIGFFYNNSGKELSSHWRPKDVVVVALGLTVSVLVLLTNLLVIAAIASN
  1   ---------+---------+---------+---------+---------+---------+   60

RRFHQPIYYLLGNLAAADLFAGVAYLFLMFHTGPRTARLSLEGWFLRQGLLDTSLTASVA
 61   ---------+---------+---------+---------+---------+---------+  120

TLLAIAVERHRSVMAVQLHSRLPRGRVVMLIVGVWVAALGLGLLPAHSWHCLCALDRCSR
121   ---------+---------+---------+---------+---------+---------+  180

MAPLLSRSYLAVWALSSLLVFLLMVAVYTRIFFYVRRRVQRMAEHVSCHPRYRETTLSLV
181   ---------+---------+---------+---------+---------+---------+  240

KTVVIILGAFVVCWTPGQVVLLLDGLGCESCNVLAVEKYFLLLAEANSLVNAAVYSCRDA
241   ---------+---------+---------+---------+---------+---------+  300

EMRRTFRRLLCCACLRQSTRESVHYTSSAQGGASTRIMLPENGHPLMDSTL*
301   ---------+---------+---------+---------+---------+--   352
```

Fig. 22A

Human Edg-6 Sequence

```
     ATGGTCATCATGGGCCAGTGCTACTACAACGAGACCATCGGCTTCTTCTATAACAACAGT
  1  ------------+----------+----------+----------+----------+   60
     TACCAGTAGTACCCGGTCACGATGATGTTGCTCTGGTAGCCGAAGAAGATATTGTTGTCA

GGCAAAGAGCTCAGCTCCCACTGGCGGCCCAAGGATGTGGTCGTGGTGGCACTGGGGCTG
 61  ------------+----------+----------+----------+----------+  120
     CCGTTTCTCGAGTCGAGGGTGACCGCCGGGTTCCTACACCAGCACCACCGTGACCCCGAC

ACCGTCAGCGTGCTGGTGCTGCTGACCAATCTGCTGGTCATAGCAGCCATCGCCTCCAAC
121  ------------+----------+----------+----------+----------+  180
     TGGCAGTCGCACGACCACGACGACTGGTTAGACGACCAGTATCGTCGGTAGCGGAGGTTG

CGCCGCTTCCACCAGCCCATCTACTACCTGCTCGGCAATCTGGCCGCGGCTGACCTCTTC
181  ------------+----------+----------+----------+----------+  240
     GCGGCGAAGGTGGTCGGGTAGATGATGGACGAGCCGTTAGACCGGCGCCGACTGGAGAAG

GCGGGCGTGGCCTACCTCTTCCTCATGTTCCACACTGGTCCCCGCACAGCCCGACTTTCA
241  ------------+----------+----------+----------+----------+  300
     CGCCCGCACCGGATGGAGAAGGAGTACAAGGTGTGACCAGGGGCGTGTCGGGCTGAAAGT

CTTGAGGGCTGGTTCCTGCGGCAGGGCTTGCTGGACACAAGCCTCACTGCGTCGGTGGCC
301  ------------+----------+----------+----------+----------+  360
     GAACTCCCGACCAAGGACGCCGTCCCGAACGACCTGTGTTCGGAGTGACGCAGCCACCGG

ACACTGCTGGCCATCGCCGTGGAGCGGCACCGCAGTGTGATGGCCGTGCAGCTGCACAGC
361  ------------+----------+----------+----------+----------+  420
     TGTGACGACCGGTAGCGGCACCTCGCCGTGGCGTCACACTACCGGCACGTCGACGTGTCG

CGCCTGCCCCGTGGCCGCGTGGTCATGCTCATTGTGGGCGTGTGGGTGGCTGCCCTGGGC
421  ------------+----------+----------+----------+----------+  480
     GCGGACGGGGCACCGGCGCACCAGTACGAGTAACACCCGCACACCCACCGACGGGACCCG

CTGGGGCTGCTGCCTGCCCACTCCTGGCACTGCCTCTGTGCCCTGGACCGCTGCTCACGC
481  ------------+----------+----------+----------+----------+  540
     GACCCCGACGACGGACGGGTGAGGACCGTGACGGAGACACGGGACCTGGCGACGAGTGCG

ATGGCACCCCTGCTCAGCCGCTCCTATTTGGCCGTCTGGGCTCTGTCGAGCCTGCTTGTC
541  ------------+----------+----------+----------+----------+  600
     TACCGTGGGGACGAGTCGGCGAGGATAAACCGGCAGACCCGAGACAGCTCGGACGAACAG

TTCCTGCTCATGGTGGCTGTGTACACCCGCATTTTCTTCTACGTGCGGCGGCGAGTGCAG
601  ------------+----------+----------+----------+----------+  660
     AAGGACGAGTACCACCGACACATGTGGGCGTAAAAGAAGATGCACGCCGCCGCTCACGTC

CGCATGGCAGAGCATGTCAGCTGCCACCCCGCTACCGAGAGACCACGCTCAGCCTGGTC
661  ------------+----------+----------+----------+----------+  720
     GCGTACCGTCTCGTACAGTCGACGGTGGGGCGATGGCTCTCTGGTGCGAGTCGGACCAG

AAGACTGTTGTCATCATCCTGGGGGCGTTCGTGGTCTGCTGGACACCAGGCCAGGTGGTA
721  ------------+----------+----------+----------+----------+  780
     TTCTGACAACAGTAGTAGGACCCCCGCAAGCACCAGACGACCTGTGGTCCGGTCCACCAT

CTGCTCCTGGATGGTTTAGGCTGTGAGTCCTGCAATGTCCTGGCTGTAGAAAAGTACTTC
781  ------------+----------+----------+----------+----------+  840
     GACGAGGACCTACCAAATCCGACACTCAGGACGTTACAGGACCGACATCTTTTCATGAAG
```

Fig.22B

```
       CTACTGcTGGCCGAGGCCAACTCACTGGTCAATGCTGCTGTGTACTCTTGCCGAGATGCT
841    ------------+---------+---------+---------+---------+---------+    900
       GATGACgACCGGCTCCGGTTGAGTGACCAGTTACGACGACACATGAGAACGGCTCTACGA

GAGATGCGCCGCACCTTCCGCCGCCTTCTCTGCTGCGGGTGCCTCCGCCAGTCCACCCGC
901    ------------+---------+---------+---------+---------+---------+    960
       CTCTACGCGGCGTGGAAGGCGGCGGAAGAGACGACGCGCACGGAGGCGGTCAGGTGGGCG

GAGTCTGTCCACTATACATCCTCTGCCCAGGGAGGTGCCAGCACTCGCATCATGCTTCCC
961    ------------+---------+---------+---------+---------+---------+    1020
       CTCAGACAGGTGATATGTAGGAGACGGGTCCCTCCACGGTCGTGAGCGTAGTACGAAGGG

GAGAACGGCCACCCACTGATGGACTCCACCCTTTAG
1021   ------------+---------+---------+------    1056
       CTCTTGCCGGTGGGTGACTACCTGAGGTGGGAAATC

                          SEQUENCE LISTING

<160> NUMBER OF SEQ ID NOS: 24

<210> SEQ ID NO 1
<211> LENGTH: 35
<212> TYPE: DNA
<213> ORGANISM: Rattus sp.

<400> SEQUENCE: 1
gagaaggttc aggaacacta caattacacc aagga                              35

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: synthetic
      primer

<400> SEQUENCE: 2
attataccaa ggagacgctg gaaac                                         25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: synthetic
      primer

<400> SEQUENCE: 3
agagagcaag gtattggcta cgaag                                         25

<210> SEQ ID NO 4
<211> LENGTH: 22
<212> TYPE: DNA
<213> ORGANISM: Artificial Sequence
```

```
<220> FEATURE:
<223> OTHER INFORMATION: Description of Artificial Sequence: synthetic
      primer

<400> SEQUENCE: 4
tcctctcctc gtcacatttc cc                                                  22

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: synthetic
      primer

<400> SEQUENCE: 5
gcattcacaa gaaattactc tgaggc                                              26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: synthetic
      primer

<400> SEQUENCE: 6
gagccccacc atgggcagct tgtact                                              26

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: synthetic
      primer

<400> SEQUENCE: 7
gcattcacaa gaaattactc tgaggc                                              26

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: synthetic
      primer

<400> SEQUENCE: 8
tttaaaaagc ttcccaccat gggcagcttg tact                                     34

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: synthetic
      primer

<400> SEQUENCE: 9
tatatatcta gacattcaca agaaattact ctgaggc                                  37

<210> SEQ ID NO 10
<211> LENGTH: 32
<212> TYPE: DNA
<213> ORGANISM: Artificial Sequence
<220> FEATURE:
```

<223> OTHER INFORMATION: Description of Artificial Sequence: synthetic
    primer

<400> SEQUENCE: 10
tatatatcta gaggaaatgt gacgaggaga gg                32

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: synthetic
    primer

<400> SEQUENCE: 11
tttaaaggta ccgccaccat gggcagcttg tac               33

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: synthetic
    primer

<400> SEQUENCE: 12
tatatatcta gagaccaccg tgttgccctc cag               33

<210> SEQ ID NO 13
<211> LENGTH: 445
<212> TYPE: DNA
<213> ORGANISM: Homo sapiens

<400> SEQUENCE: 13
aaagccccat ggccccagca ggcctctgag ccccaccatg ggcagcttgt actcggagta    60
cctgaacccc aacaaggtcc aggaacacta taattatacc aaggagacgc tggaaacgca   120
ggagacgacc tcccgccagg tggcctcggc attcatcgtc atcctctgtt gcgccattgt   180
ggtggaaaac cttctggtgc tcattgcggt ggcccgaaac agcaagttcc actcggcaat   240
gtacctgttt ctgggcaacc tggccgcctc cgatctactg caggcgtggg ccttcgtagc   300
caataccttg ctctctggct ctgtcacgct gaggctgacg cctgtgcagt ggtttgcccg   360
ggacggtctg ccttcatcac gctctcggcc tctgtcttca gcctcctggc catcgccatt   420
gagcgccacg tggccattgc aaagg                                         445

<210> SEQ ID NO 14
<211> LENGTH: 364
<212> TYPE: DNA
<213> ORGANISM: Homo sapiens

<400> SEQUENCE: 14
aaagccccat ggccccagca ggcctctgag ccccaccatg ggcagcttgt actcggagta    60
cctgaacccc aacaaggtcc aggaacacta taattatacc aaggagacgc tggaaacgca   120
ggagacgacc tcccgccagg tggcctcggc cttcatcgtc atcctctgtt gcgccattgt   180
ggtggaaaac cttctggtgc tcattgcggt ggcccgaaac agcaagttcc actcggcaat   240
gtacctgttt ctgggcaacc tggccgcctc cgatctactg caggcgtggg ccttcgtagc   300
caataccttg ctctctggct ctgtcacgct gaggctgacg cctgtgcagt ggtttgcccg   360
ggac                                                                364

-continued

```
<210> SEQ ID NO 15
<211> LENGTH: 369
<212> TYPE: DNA
<213> ORGANISM: Homo sapiens

<400> SEQUENCE: 15
agttctgaaa gccccatggc cccagcaggc ctctgagccc caccatgggc agcttgtact      60
cggagtacct gaaccccaac aaggtccagg aacactataa ttataccaag gagacgctgg    120
aaacgcagga gacgacctcc cgccaggtgg gctcggcctt catcgtcatc ctctgttgcg    180
ccattgtggt ggaaaacctt ctggtgctca ttgcggtggc ccgaaacagc aagttccact    240
cggcaatgta cctgtttctg gcaacctggg ccgcctccga tctactggca ggcgtggctt    300
cgtagccaat accttgctct ctggctctgt cacgctgagg ctgacgcctg tgcagtggtt    360
tgcccggga                                                            369

<210> SEQ ID NO 16
<211> LENGTH: 1170
<212> TYPE: DNA
<213> ORGANISM: Homo sapiens
<220> FEATURE:
<221> NAME/KEY: CDS
<222> LOCATION: (38)..(1096)
<220> FEATURE:
<221> NAME/KEY: MOD_RES
<222> LOCATION: (273)
<223> OTHER INFORMATION: Leu or Phe

<400> SEQUENCE: 16
aaagccccat ggccccagca ggcctctgag ccccacc atg ggc agc ttg tac tcg      55
                                        Met Gly Ser Leu Tyr Ser
                                         1               5 gag tac ctg aac ccc aac aag gtc cag gaa cac tat aat tat acc aag     103
Glu Tyr Leu Asn Pro Asn Lys Val Gln Glu His Tyr Asn Tyr Thr Lys
             10                  15                  20 gag acg ctg gaa acg cag gag acg acc tcc cgc cag gtg gcc tcg gcc     151
Glu Thr Leu Glu Thr Gln Glu Thr Thr Ser Arg Gln Val Ala Ser Ala
         25                  30                  35 ttc atc gtc atc ctc tgt tgc gcc att gtg gtg gaa aac ctt ctg gtg     199
Phe Ile Val Ile Leu Cys Cys Ala Ile Val Val Glu Asn Leu Leu Val
     40                  45                  50 ctc att gcg gtg gcc cga aac agc aag ttc cac tcg gca atg tac ctg     247
Leu Ile Ala Val Ala Arg Asn Ser Lys Phe His Ser Ala Met Tyr Leu
 55                  60                  65                  70 ttt ctg ggc aac ctg gcc gcc tcc gat cta ctg gca ggc gtg gcc ttc     295
Phe Leu Gly Asn Leu Ala Ala Ser Asp Leu Leu Ala Gly Val Ala Phe
                 75                  80                  85 gta gcc aat acc ttg ctc tct ggc tct gtc acg ctg agg ctg acg cct     343
Val Ala Asn Thr Leu Leu Ser Gly Ser Val Thr Leu Arg Leu Thr Pro
             90                  95                 100 gtg cag tgg ttt gcc cgg gag ggc tct gcc ttc atc acg ctc tcg gcc     391
Val Gln Trp Phe Ala Arg Glu Gly Ser Ala Phe Ile Thr Leu Ser Ala
         105                 110                 115 tct gtc ttc agc ctc ctg gcc atc gcc att gag cgc cac gtg gcc att     439
Ser Val Phe Ser Leu Leu Ala Ile Ala Ile Glu Arg His Val Ala Ile
     120                 125                 130 gcc aag gtc aag ctg tat ggc agc gac aag agc tgc cgc atg ctt ctg     487
Ala Lys Val Lys Leu Tyr Gly Ser Asp Lys Ser Cys Arg Met Leu Leu
135                 140                 145                 150 ctc atc ggg gcc tcg tgg ctc atc tcg ctg gtc ctc ggt ggc ctg ccc     535
Leu Ile Gly Ala Ser Trp Leu Ile Ser Leu Val Leu Gly Gly Leu Pro
```

```
                155                 160                 165
atc ctt ggc tgg aac tgc ctg ggc cac ctc gag gcc tgc tcc act gtc     583
Ile Leu Gly Trp Asn Cys Leu Gly His Leu Glu Ala Cys Ser Thr Val
            170                 175                 180 ctg cct ctc tac gcc aag cat tat gtg ctg tgc gtg gtg acc atc ttc     631
Leu Pro Leu Tyr Ala Lys His Tyr Val Leu Cys Val Val Thr Ile Phe
        185                 190                 195 tcc atc atc ctg ttg gcc atc gtg gcc ctg tac gtg cgc atc tac tgc     679
Ser Ile Ile Leu Leu Ala Ile Val Ala Leu Tyr Val Arg Ile Tyr Cys
    200                 205                 210 gtg gtc cgc tca agc cac gct gac atg gcc gcc ccg cag acg cta gcc     727
Val Val Arg Ser Ser His Ala Asp Met Ala Ala Pro Gln Thr Leu Ala
215                 220                 225                 230 ctc ctc aag acg gtc acc atc gtg cta ggc gtc ttt atc gtc tgc tgg     775
Leu Leu Lys Thr Val Thr Ile Val Leu Gly Val Phe Ile Val Cys Trp
                235                 240                 245 ctg ccc gcc ttc agc atc ctc ctt ctg gac tat gcc tgt ccc gtc cac     823
Leu Pro Ala Phe Ser Ile Leu Leu Leu Asp Tyr Ala Cys Pro Val His
            250                 255                 260 tcc tgc ccg atc ctc tac aaa gcc cac tac ytt ttc gcc gtc tcc acc     871
Ser Cys Pro Ile Leu Tyr Lys Ala His Tyr Xaa Phe Ala Val Ser Thr
        265                 270                 275 ctg aat tcc ctg ctc aac ccc gtc atc tac acg tgg cgc agc cgg gac     919
Leu Asn Ser Leu Leu Asn Pro Val Ile Tyr Thr Trp Arg Ser Arg Asp
    280                 285                 290 ctg cgg cgg gag gtg ctt cgg ccg ctg cag tgc tgg cgg ccg ggg gtg     967
Leu Arg Arg Glu Val Leu Arg Pro Leu Gln Cys Trp Arg Pro Gly Val
295                 300                 305                 310 ggg gtg caa gga cgg agg cgg ggc ggg acc ccg ggc cac cac ctc ctg     1015
Gly Val Gln Gly Arg Arg Arg Gly Gly Thr Pro Gly His His Leu Leu
                315                 320                 325 cca ctc cgc agc tcc agc tcc ctg gag agg ggc atg cac atg ccc acg     1063
Pro Leu Arg Ser Ser Ser Ser Leu Glu Arg Gly Met His Met Pro Thr
            330                 335                 340 tca ccc acg ttt ctg gag ggc aac acg gtg gtc tgagggtggg ggtggaccaa   1116
Ser Pro Thr Phe Leu Glu Gly Asn Thr Val Val
        345                 350 caaccaggcc agggcatagg ggttcatgga aaggccactg ggtgacccca aata          1170

<210> SEQ ID NO 17
<211> LENGTH: 353
<212> TYPE: PRT
<213> ORGANISM: Homo sapiens
<220> FEATURE:
<221> NAME/KEY: MOD_RES
<222> LOCATION: (273)
<223> OTHER INFORMATION: Leu or Phe

<400> SEQUENCE: 17

Met Gly Ser Leu Tyr Ser Glu Tyr Leu Asn Pro Asn Lys Val Gln Glu
 1               5                  10                  15

His Tyr Asn Tyr Thr Lys Glu Thr Leu Glu Thr Gln Glu Thr Thr Ser
            20                  25                  30

Arg Gln Val Ala Ser Ala Phe Ile Val Ile Leu Cys Cys Ala Ile Val
        35                  40                  45

Val Glu Asn Leu Leu Val Leu Ile Ala Val Ala Arg Asn Ser Lys Phe
    50                  55                  60

His Ser Ala Met Tyr Leu Phe Leu Gly Asn Leu Ala Ala Ser Asp Leu
65                  70                  75                  80
```

```
Leu Ala Gly Val Ala Phe Val Ala Asn Thr Leu Leu Ser Gly Ser Val
                85                  90                  95

Thr Leu Arg Leu Thr Pro Val Gln Trp Phe Ala Arg Glu Gly Ser Ala
            100                 105                 110

Phe Ile Thr Leu Ser Ala Ser Val Phe Ser Leu Leu Ala Ile Ala Ile
        115                 120                 125

Glu Arg His Val Ala Ile Ala Lys Val Lys Leu Tyr Gly Ser Asp Lys
    130                 135                 140

Ser Cys Arg Met Leu Leu Ile Gly Ala Ser Trp Leu Ile Ser Leu
145                 150                 155                 160

Val Leu Gly Gly Leu Pro Ile Leu Gly Trp Asn Cys Leu His Leu
                165                 170                 175

Glu Ala Cys Ser Thr Val Leu Pro Leu Tyr Ala Lys His Tyr Val Leu
            180                 185                 190

Cys Val Val Thr Ile Phe Ser Ile Ile Leu Leu Ala Ile Val Ala Leu
        195                 200                 205

Tyr Val Arg Ile Tyr Cys Val Val Arg Ser Ser His Ala Asp Met Ala
    210                 215                 220

Ala Pro Gln Thr Leu Ala Leu Leu Lys Thr Val Thr Ile Val Leu Gly
225                 230                 235                 240

Val Phe Ile Val Cys Trp Leu Pro Ala Phe Ser Ile Leu Leu Leu Asp
                245                 250                 255

Tyr Ala Cys Pro Val His Ser Cys Pro Ile Leu Tyr Lys Ala His Tyr
            260                 265                 270

Xaa Phe Ala Val Ser Thr Leu Asn Ser Leu Leu Asn Pro Val Ile Tyr
        275                 280                 285

Thr Trp Arg Ser Arg Asp Leu Arg Arg Glu Val Leu Arg Pro Leu Gln
    290                 295                 300

Cys Trp Arg Pro Gly Val Gly Val Gln Gly Arg Arg Gly Gly Thr
305                 310                 315                 320

Pro Gly His His Leu Leu Pro Leu Arg Ser Ser Ser Leu Glu Arg
                325                 330                 335

Gly Met His Met Pro Thr Ser Pro Thr Phe Leu Glu Gly Asn Thr Val
            340                 345                 350

Val

<210> SEQ ID NO 18
<211> LENGTH:
<212> TYPE:
<213> ORGANISM:

<400> SEQUENCE: 18

000

<210> SEQ ID NO 19
<211> LENGTH: 1062
<212> TYPE: DNA
<213> ORGANISM: Homo sapiens

<400> SEQUENCE: 19
atgggcagct tgtactcgga gtacctgaac cccaacaagg tccaggaaca ctataattat    60
accaaggaga cgctggaaac gcaggagacg acctcccgcc aggtggcctc ggccttcatc   120
gtcatcctct gttgcgccat tgtggtggaa aaccttctgg tgctcattgc ggtggcccga   180
aacagcaagt tccactcggc aatgtacctg tttctgggca acctggccgc ctccgatcta   240
```

-continued

| | |
|---|---|
| ctggcaggcg tggccttcgt agccaatacc ttgctctctg gctctgtcac gctgaggctg | 300 |
| acgcctgtgc agtggtttgc ccgggagggc tctgccttca tcacgctctc ggcctctgtc | 360 |
| ttcagcctcc tggccatcgc cattgagcgc acgtggcca ttgccaaggt caagctgtat | 420 |
| ggcagcgaca agagctgccg catgcttctg ctcatcgggg cctcgtggct catctcgctg | 480 |
| gtcctcggtg gcctgcccat ccttggctgg aactgcctgg ccacctcga ggcctgctcc | 540 |
| actgtcctgc tctctacgc caagcattat gtgctgtgcg tggtgaccat cttctccatc | 600 |
| atcctgttgg ccgtcgtggc cctgtacgtg cgcatctact gcgtggtccg ctcaagccac | 660 |
| gctgacatgg ccgccccgca gacgctagcc ctgctcaaga cggtcaccat cgtgctaggc | 720 |
| gtctttatcg tctgctggct gcccgccttc agcatcctcc ttctggacta tgcctgtccc | 780 |
| gtccactcct gcccgatcct ctacaaagcc cactaccttt cgccgtctc caccctgaat | 840 |
| tccctgctca cccccgtcat ctacacgtgg cgcagccggg acctgcggcg ggaggtgctt | 900 |
| cggccgctgc agtgctggcg gccggggggtg ggggtgcaag gacggaggcg gggcgggacc | 960 |
| ccgggccacc acctcctgcc actccgcagc tccagctccc tggagagggg catgcacatg | 1020 |
| cccacgtcac ccacgtttct ggagggcaac acggtggtct ga | 1062 |

<210> SEQ ID NO 20
<211> LENGTH:
<212> TYPE:
<213> ORGANISM:

<400> SEQUENCE: 20

000

<210> SEQ ID NO 21
<211> LENGTH: 352
<212> TYPE: PRT
<213> ORGANISM: Rattus sp.

<400> SEQUENCE: 21

Met Gly Gly Leu Tyr Ser Glu Tyr Leu Asn Pro Glu Lys Val Gln Glu
 1               5                  10                  15

His Tyr Asn Tyr Thr Lys Glu Thr Leu Asp Met Gln Glu Thr Pro Ser
                20                  25                  30

Arg Lys Val Ala Ser Ala Phe Ile Ile Ile Leu Cys Cys Ala Ile Val
            35                  40                  45

Val Glu Asn Leu Leu Val Leu Ile Ala Val Ala Arg Asn Ser Lys Phe
        50                  55                  60

His Ser Ala Met Tyr Leu Phe Leu Gly Asn Leu Ala Ala Ser Asp Leu
65                  70                  75                  80

Leu Ala Gly Val Ala Phe Val Ala Asn Thr Leu Leu Ser Gly Pro Val
                85                  90                  95

Thr Leu Ser Leu Thr Pro Leu Gln Trp Phe Ala Arg Glu Gly Ser Ala
            100                 105                 110

Phe Ile Thr Leu Ser Ala Ser Val Phe Ser Leu Leu Ala Ile Ala Ile
        115                 120                 125

Glu Arg Gln Val Ala Ile Ala Lys Val Lys Leu Tyr Gly Ser Asp Lys
    130                 135                 140

Ser Cys Arg Met Leu Met Leu Ile Gly Ala Ser Trp Leu Ile Ser Leu
145                 150                 155                 160

Ile Leu Gly Gly Leu Pro Ile Leu Gly Trp Asn Cys Leu Asp His Leu
                165                 170                 175

```
Glu Ala Cys Ser Thr Val Leu Pro Leu Tyr Ala Lys His Tyr Val Leu
            180                 185                 190
Cys Val Val Thr Ile Phe Ser Val Ile Leu Leu Ala Ile Val Ala Leu
            195                 200                 205
Tyr Val Arg Ile Tyr Phe Val Arg Ser Ser His Ala Asp Val Ala
210                 215                 220
Gly Pro Gln Thr Leu Ala Leu Leu Lys Thr Val Thr Ile Val Leu Gly
225                 230                 235                 240
Val Phe Ile Ile Cys Trp Leu Pro Ala Phe Ser Ile Leu Leu Leu Asp
            245                 250                 255
Ser Thr Cys Pro Val Arg Ala Cys Pro Val Leu Tyr Lys Ala His Tyr
            260                 265                 270
Phe Phe Ala Phe Ala Thr Leu Asn Ser Leu Leu Asn Pro Val Ile Tyr
            275                 280                 285
Thr Trp Arg Ser Arg Asp Leu Arg Arg Glu Val Leu Arg Pro Leu Leu
            290                 295                 300
Cys Trp Arg Gln Gly Lys Gly Ala Thr Gly Arg Arg Gly Gly Asn Pro
305                 310                 315                 320
Gly His Arg Leu Leu Pro Leu Arg Ser Ser Ser Leu Glu Arg Gly
            325                 330                 335
Leu His Met Pro Thr Ser Pro Thr Phe Leu Glu Gly Asn Thr Val Val
            340                 345                 350

<210> SEQ ID NO 22
<211> LENGTH: 353
<212> TYPE: PRT
<213> ORGANISM: Homo sapiens

<400> SEQUENCE: 22

Met Gly Ser Leu Tyr Ser Glu Tyr Leu Asn Pro Asn Lys Val Gln Glu
1               5                   10                  15
His Tyr Asn Tyr Thr Lys Glu Thr Leu Glu Thr Gln Glu Thr Thr Ser
            20                  25                  30
Arg Gln Val Ala Ser Ala Phe Ile Val Ile Leu Cys Cys Ala Ile Val
            35                  40                  45
Val Glu Asn Leu Leu Val Leu Ile Ala Val Ala Arg Asn Ser Lys Phe
        50                  55                  60
His Ser Ala Met Tyr Leu Phe Leu Gly Asn Leu Ala Ala Ser Asp Leu
65                  70                  75                  80
Leu Ala Gly Val Ala Phe Val Ala Asn Thr Leu Leu Ser Gly Ser Val
                85                  90                  95
Thr Leu Arg Leu Thr Pro Val Gln Trp Phe Ala Arg Glu Gly Ser Ala
            100                 105                 110
Phe Ile Thr Leu Ser Ala Ser Val Phe Ser Leu Leu Ala Ile Ala Ile
            115                 120                 125
Glu Arg His Val Ala Ile Ala Lys Val Lys Leu Tyr Gly Ser Asp Lys
            130                 135                 140
Ser Cys Arg Met Leu Leu Leu Ile Gly Ala Ser Trp Leu Ile Ser Leu
145                 150                 155                 160
Val Leu Gly Gly Leu Pro Ile Leu Gly Trp Asn Cys Leu Gly His Leu
                165                 170                 175
Glu Ala Cys Ser Thr Val Leu Pro Leu Tyr Ala Lys His Tyr Val Leu
            180                 185                 190
Cys Val Val Thr Ile Phe Ser Ile Ile Leu Leu Ala Val Val Ala Leu
            195                 200                 205
```

-continued

```
Tyr Val Arg Ile Tyr Cys Val Val Arg Ser Ser His Ala Asp Met Ala
        210                 215                 220
Ala Pro Gln Thr Leu Ala Leu Leu Lys Thr Val Thr Ile Val Leu Gly
225                 230                 235                 240
Val Phe Ile Val Cys Trp Leu Pro Ala Phe Ser Ile Leu Leu Leu Asp
                    245                 250                 255
Tyr Ala Cys Pro Val His Ser Cys Pro Ile Leu Tyr Lys Ala His Tyr
                260                 265                 270
Leu Phe Ala Val Ser Thr Leu Asn Ser Leu Asn Pro Val Ile Tyr
            275                 280                 285
Thr Trp Arg Ser Arg Asp Leu Arg Arg Glu Val Leu Arg Pro Leu Gln
        290                 295                 300
Cys Trp Arg Pro Gly Val Gly Val Gln Gly Arg Arg Gly Gly Thr
305                 310                 315                 320
Pro Gly His His Leu Leu Pro Leu Arg Ser Ser Ser Leu Glu Arg
                    325                 330                 335
Gly Met His Met Pro Thr Ser Pro Thr Phe Leu Glu Gly Asn Thr Val
                340                 345                 350
Val
```

<210> SEQ ID NO 23
<211> LENGTH: 351
<212> TYPE: PRT
<213> ORGANISM: Homo sapiens

<400> SEQUENCE: 23

```
Met Val Ile Met Gly Gln Cys Tyr Tyr Asn Glu Thr Ile Gly Phe Phe
1               5                   10                  15
Tyr Asn Asn Ser Gly Lys Glu Leu Ser Ser His Trp Arg Pro Lys Asp
                20                  25                  30
Val Val Val Val Ala Leu Gly Leu Thr Val Ser Val Leu Val Leu Leu
            35                  40                  45
Thr Asn Leu Leu Val Ile Ala Ala Ile Ala Ser Asn Arg Arg Phe His
        50                  55                  60
Gln Pro Ile Tyr Tyr Leu Leu Gly Asn Leu Ala Ala Ala Asp Leu Phe
65                  70                  75                  80
Ala Gly Val Ala Tyr Leu Phe Leu Met Phe His Thr Gly Pro Arg Thr
                85                  90                  95
Ala Arg Leu Ser Leu Glu Gly Trp Phe Leu Arg Gln Gly Leu Leu Asp
                100                 105                 110
Thr Ser Leu Thr Ala Ser Val Ala Thr Leu Leu Ala Ile Ala Val Glu
            115                 120                 125
Arg His Arg Ser Val Met Ala Val Gln Leu His Ser Arg Leu Pro Arg
        130                 135                 140
Gly Arg Val Val Met Leu Ile Val Gly Val Trp Val Ala Ala Leu Gly
145                 150                 155                 160
Leu Gly Leu Leu Pro Ala His Ser Trp His Cys Leu Cys Ala Leu Asp
                165                 170                 175
Arg Cys Ser Arg Met Ala Pro Leu Leu Ser Arg Ser Tyr Leu Ala Val
                180                 185                 190
Trp Ala Leu Ser Ser Leu Leu Val Phe Leu Leu Met Val Ala Val Tyr
            195                 200                 205
```

```
Thr Arg Ile Phe Phe Tyr Val Arg Arg Arg Val Gln Arg Met Ala Glu
    210                 215                 220
His Val Ser Cys His Pro Arg Tyr Arg Glu Thr Thr Leu Ser Leu Val
225                 230                 235                 240
Lys Thr Val Val Ile Ile Leu Gly Ala Phe Val Cys Trp Thr Pro
                245                 250                 255
Gly Gln Val Val Leu Leu Asp Gly Leu Gly Cys Glu Ser Cys Asn
                260                 265                 270
Val Leu Ala Val Glu Lys Tyr Phe Leu Leu Ala Glu Ala Asn Ser
            275                 280                 285
Leu Val Asn Ala Ala Val Tyr Ser Cys Arg Asp Ala Glu Met Arg Arg
    290                 295                 300
Thr Phe Arg Arg Leu Leu Cys Cys Ala Cys Leu Arg Gln Ser Thr Arg
305                 310                 315                 320
Glu Ser Val His Tyr Thr Ser Ser Ala Gln Gly Gly Ala Ser Thr Arg
                325                 330                 335
Ile Met Leu Pro Glu Asn Gly His Pro Leu Met Asp Ser Thr Leu
            340                 345                 350

<210> SEQ ID NO 24
<211> LENGTH: 1056
<212> TYPE: DNA
<213> ORGANISM: Homo sapiens

<400> SEQUENCE: 24
atggtcatca tgggccagtg ctactacaac gagaccatcg gcttcttcta taacaacagt      60
ggcaaagagc tcagctccca ctggcggccc aaggatgtgg tcgtggtggc actggggctg     120
accgtcagcg tgctggtgct gctgaccaat ctgctggtca tagcagccat cgcctccaac     180
cgccgcttcc accagcccat ctactacctg ctcggcaatc tggccgcggc tgacctcttc     240
gcgggcgtgg cctacctctt cctcatgttc cacactggtc ccgcacagc ccgactttca      300 cttgagggct ggttcctgcg caggcttg ctggacacaa gcctcactgc gtcggtggcc       360
acactgctgg ccatcgccgt ggagcggcac cgcagtgtga tggccgtgca gctgcacagc     420
cgcctgcccc gtggccgcgt ggtcatgctc attgtgggcg tgtgggtggc tgccctgggc     480
ctggggctgc tgcctgccca ctcctggcac tgcctctgtg ccctggaccg ctgctcacgc     540
atggcacccc tgctcagccg ctcctatttg gccgtctggg ctctgtcgag cctgcttgtc     600
ttcctgctca tggtggctgt gtacacccgc attttcttct acgtgcggcg gcgagtgcag     660
cgcatggcag agcatgtcag ctgccacccc cgctaccgag agaccacgct cagcctggtc     720
aagactgttg tcatcatcct gggggcgttc gtggtctgct ggacaccagg ccaggtggta     780
ctgctcctgg atggtttagg ctgtgagtcc tgcaatgtcc tggctgtaga aaagtacttc     840
ctactgctgg ccgaggccaa ctcactggtc aatgctgctg tgtactcttg ccgagatgct     900
gagatgcgcc gcaccttccg ccgccttctc tgctgcgcgt gcctccgcca gtccacccgc     960
gagtctgtcc actatacatc ctctgcccag ggaggtgcca gcactcgcat catgcttccc    1020
gagaacggcc acccactgat ggactccacc ctttag                              1056
```

```

ISOLATED HUMAN EDG-4 RECEPTOR

This is a Continuation of application Ser. No. 09/222,995 filed Dec. 30, 1998 now abandoned, which claims the benefit of U.S. Provisional Application Ser. No. 60/070,185, filed Dec. 30, 1997, U.S. Provisional Application Ser. No. 60/080,610, filed Apr. 3. 1998 and U.S. Provisional Application Ser. No. 60/109,885, filed Nov. 25, 1998. The disclosure of the prior application(s) is hereby incorporated by reference herein in its entirety.

FIELD OF THE INVENTION

The present invention is in the field of molecular biology. More partcularly, the present invention relates to a novel lysolipid receptors a human EDG4 receptor, a method of identifying lysolipid receptors involved in inflammatory response and the lysolipid receptors so identified, and a method of identifying ligands which interact with such lysolipid receptors.

BACKGROUND OF THE INVENTION (a) EDG Receptors

EDG receptors have been grouped with iorphan reeptors because their endogehous ligands are not known (for example see Hla T and Maciag T (1990) Biol. Chem. 265:9308–13; 5,585,476). Recently, however, lysophosphatidic acid (LPA) has been demonstrated to be the endogenous ligand for the EDG-2 receptor (Hecht et al. (1996) J. Cell. Biol. 135 1071–1083; An et al. (1997) Biochem. Biophys. Res. Comm. 213: 619–622).

The EDG receptors are seven transmembrane G protein coupled receptors (T7Gs or GPCRs). GPCRs are so named because of their seven hydrophobic domains of 20–30 amino acids which span the plasma membrane and form a bundle of antiparallel α helices. These transmembrane segments (TMS) are designated by roman numerals I–VII and account for stuctural and functional features of the receptor. In most cases, the bundle of helices forms a binding pocket; however, when the binding site must accommodate more bulky molecules, the extracellular N-terminal segment or one or more of the three extracellular loops participate in binding and in subsequent induction of conformational change in intracellular portions of the receptor. The activated receptor, in turn, interacts with an intracellular G-protiein complex which mediates further intracellular signaling activities such as the production of second messengers such as cyclic AMP (cAMP), phospholipase C, inositol triphosphate, activation of protein kinases, alteration in the expression of specific genes.

When the receptor is activated but the binding of a ligand, the conformation of the receptor changes allowing it to interact with and activate a G protein. The activated G protein cause a molecule of guanosine diphoshate (GDP), that is bound to the surface of the G protein, to be replaced with a molecule of guanosine triphosphate (GTP), which causes another alteration in the conformation of the G protein. With GTP bound to its stufac, the G protein can regulate the activity of an effector. These effectors include enzymes such as adenylyl cyclase and phospholipase C and certain transport protein and ion channels such as calcium ions, potassium ions or sodium ions.

GPCRs are expressed and activated during numerous developmental and disease processes. Identification of a novel GPCR provides the opportunity to diagnose or intervene in such processes. The receptor can be used in screening assays to identify physiological or pharmaceutical molecules which trigger, prolong or inhibit a receptor's activity or differentially modulate distinct intracellular pathways which are controlled by GPCRs. However, for many of the GPCRs (such as the EDG receptors) the biological processes mediated by the receptor are currently unknown. There exists a need therefore for methods to identify the biological processes mediated by these GPCRs and also for methods of identifying other GPCRs that may be involved in these proesses.

Because there are diverse functions of GPCRs, it is not suprising that there are a number of theraeutic drugs that act by modifying the function of GPCRs. Therapeutic drugs which modify the GPCRs are particularly attractive because of the ability to design such drugs with particular specificity so that they turn on or off specific receptors and their signaling pathways.

(b) Lysophospholipids and Inflammation

LPA is a naturally-occurring agonist of the EDG-2 receptor (Hect et al. J Cell Biol 135:1071, 1996). LPA, and many other lysophospholipids, are produced by activated platelets as a consequence of inflammation-related intracellular signal transduction accompanying aggregation and thrombus formation, Similar inflammatory pathways occur in many cell types, and typically lead to production of LL and other lipid mediators within seconds to minutes, and activation of new gene expression within minutes to hours.

A number of lysophospholipids have been studied to determine their biological effects. For example, the lysophospholipd spbingosine-1-phosphate (S1P) appears to play a role in a number of CNS-related biological processes. These include apoptosis, mitogenesis and cytoskeletal reorganization. S1P has been proposed to mediate at least some of the biological function of PDGF and NGF. The former is a growth hormone with potent mitogenic and wound-healing activity. The latter is a neurotrophic factor, which has also been proposed to play a role in neuropathic pain.

In addition, it has been reported that there is activation of NF-κB by S1P in U937 cells; however, the authors assumed that S1P was an intracellular second messenger, and no attempt was made to determine whether this response was receptor-mediated. Furthermore, the functional relevance of NF-κB activation was not tested, e.g. by examining the possible upregulation of inflammatory cytokines, adhesion molecules or other NF-κB-dependent genes. If multiple receptors for S1P exist, the finding of NF-κB activation offers no utility by itself, since one, several, or all of the receptors might respond through NF-κB.

Moreover, direct modulation of NF-κB activation cascades has been proposed as a therapeutic mechanism for inflammation or apoptosis. However, NF-κB plays a vital role in inmate immunity against ubiquitous microbial pathogens and in mobilizing the antigen-specific immune system. Therefore, rather than targeting this irreplaceable defense system, it would be preferred to instead block inappropriate activation of NF-κB by specific inflammatory or apoptotic signaleing events. Accordingly, it is highly desireable to design therapeutic agents which could modulate NF-κB activation and thereby prevent unwanted apoptosis or thereby enhance immune function in immunocompromised hosts via a receptor modulated pathway.

SUMMARY OF INVENTION

It has now been discovered that there are LL/EDG receptors which are involved in an inflammatory response signaling pathway and an apoptotic signaling pathway. In particular, it has been discovered that the EDG-2, EDG-3, EDG-4, EDG-5 and EDG-6 receptors activate NF-κB and/or the production of IL-8. Accordingly, the present invention provides a link between NF-κB activation and edg receptors and hence a means for controlling NF-κB activation and thereby for controlling apoptosis and inflammatory responses.

In an aspect of the present invention, it as been discovered that agonists to the EDG-2, EDG-5 and EDG-6 receptors result in activation/production of NF-κB and/or IL-8. In particular, it has been discovered that LPA will act as an agonist to the EDG-2, EDG-5 and EDG-6 receptors resulting in activation/production of NF-κB and/or IL-8.

In another aspect of the present intention, it has been discovered that agonists to the EDG-3 and EDG-4 receptors result in activation/production of NF-κB and/or IL-8. In particular, it has been discovered that S1P and SPC will act as an agonist to the EDG-3 and EDG-4 receptor resulting in activation/production of NF-κB and/or IL-8.

In another aspect of the present invention there is provided isolated polynucleotides encoding the human EDG-4 receptor. The isolated polynucleotides may be either cDNA or genomic clones.

In particular, the present invention provides an isolated nucleotide sequence selected from the group consisting of:

(a) the nucleotide sequence comprising nucleotides 38–1099 of FIG. 15A;

(b) tab the nucleotide sequence of FIG. 15B;

(c) a nucleotide sequence with at least about 95% sequence identity to (a) or (b) and which hybridizes under stringent conditions to sequences (a) and (b), respectively;

(d) a nucleotide sequence which encodes the amino acid sequence of FIG. 16A for the human EDG-4 receptor; and (e) a nucleotide sequence which encodes the amino acid sequence of FIG. 16B for the human EDG-4 receptor.

There is also provided: expression vectors; host cells; purified amino acid sequences; complementary nucleic acid sequences; biologically active fragments; and hybridization probes, for such nucleotide sequences and their encoded amino acid sequences.

In another aspect of the present invention, there is provided a method of detemining whether a DNA sequence encods edg rceptors that are involved in inflammatory response by measuring the induction NF-κB and/or IL8 upon activation by a suitable ligand.

In another aspect of the present invention, there is provided a method of determining whether a DNA sequence encodes an edifosine receptor that is involved in inflammatory response by measuring the induction of NF-κB and/or IL-8 activation by a sutiable ligand, including edelfosine.

In another aspect of the present invention, there is provided a method of identifying ligands that interact with edg or lysolipid receptors that are involved in inflammatory response. In particular, the present invention provides a method of identifying ligands which interact with edg or lysolipid receptors by measuring the induction or lack of induction of NF-κB and/or IL-8.

In another aspect of the present invention, there is provided a method of modulating or treating an inflammatory process condition in a subject by administering an effective amount of a pharmaceutical composition comprising an agonist or antagonist of an NF-κB and/or IL-8 modulated EDG or lysolipid receptor and a pharmaceutically acceptable excipient, for upregulation or downregulation of the inflammatory process, respectively. In particular, agonists and antagonists of the EDG-2, EDG-3, EDG-4, EDG-5 and/or EDG-6 receptor are applicable.

In another aspect of the present invention, there is provided a method of modulating an immune response in a subject by administering an effective amount of a pharmaceutical composition comprising an agonist or antagonist of an NF-κB and/or IL-8 modulated EDG or lysolipid receptor and a pharmaceutically acceptable excipient, for upregulation or downregulation of the immune response, respectively. In particular, agonists and antagonists of the EDG-2, EDG 3, EDG-4, EDG-5 and/or EDG-6 receptor are applicable.

In another aspect of the present invention, there is provided a method of controlling apoptosis by activating an EDG or lysolipid receptor which receptor activates the induction of NF-κB. In particular, by modulating the EDG-2, EDG-3, EDG-4, EDG-5 and/or EDG-6 receptor via agonists or antagonists there is provided a method of controlling apoptosis.

An EDG receptor herein refers to any receptor with at least 27–30% identity, preferably at least 30–35% identity, more preferably at least 35–40% identity, even more preferably at least 40–45% and most preferably at least 45–50% identity with each other. As is known in the art, the percentage identity of the amino acid sequences of related receptors is generally greater in the same species than in different species.

BRIEF DESCRIPTION OF THE FIGURES

The following figures will now be used to describe the invention in more detail.

FIG. 14 shows a multiple alignment of EST sequences (SEQ ID NOS 13–15, respectively, in order of appearance) representing the 5' end of the open reading frame of human EDG-4 cDNA. Sequences were aligned using the PILEUP program from the Wisconsin Package Version 9.0, Genetics Computer Group (GCG), Madison, Wis. The predicted translation start of human EDG-4, based on similarity to the rat translation start site, begins at nt 45 of the multiple alignment.

FIG. 15A shows human EDG-4 cDNA (SEQ ID NO: 16) and EDG-4 predicted amino acid sequence (SEQ ID NO: 17). The cDNA sequence was derived from clones pC3-hedg4#5 and pC3-hedg4#36 isolated by PCR from human lung fibrobiast cell line WI-38 cDNA library (Origene Technologies Inc.).

FIG. 15B shows human EDG-4 cDNA (SEQ ID NO: 19) of clone pC3-Hedg4#36.

FIG. 16A shows the amino acid sequence (SEQ ID NO: 17) and features of the predicted polypeptide product of human EDG-4 cDNA of FIG. 15A.

FIG. 16B shows the amino acid sequence (SEQ ID NO: 22) of the EDG-4 polypeptide encoded by pC3-hEdg-4#36.

FIG. 17A shows the GAP alignment of the predicted human vs rat EDG-4 polypeptides (SEQ ID NOS 22 and 21, respectively, in order of appearance). The predicted amino acid sequences of two polypeptides were aligned using the GCG GAP program.

FIG. 17B shows the alignment of the amino acid sequences of EDG-4 as derived from the clones pC3-Hedg4#5 and pC3-Hedg4#36 (FIG. 16A) (SEQ ID NO: 17) with pC3-Hedg4#36 (FIG. 16B) (SEQ ID NO: 22) and with rat EDG-4/H218 (SEQ ID NO: 21) using the PILEUP program.

FIG. 21 illustrates the amino acid sequence (SEQ ID NO: 23) for human EDG-6 receptor.

FIG. 22 illustrates the cDNA sequence (SEQ ID NO: 24) for human EDG-6 receptor.

DETAILED DESCRIPTION OF THE INVENTION

The EDG receptors are characterized by structural features common to the G-protein coupled receptor class, including seven transmembrane regions, and by the functional properties of binding lysophospholipids or lysophingolipids selectively. When expressed functionally in a host cell, i.e., in operable linkage with a responsive second messenger system the EDG receptors are capable further of responding to lysophingolipid or binding by signal transduction.

In the present invention it has been discovered that EDG receptors are involved in an inflammatory response signaling pathway and an apoptotic signalling pathway by the activation of NF-κB and production of IL-8.

It has also been discovered that endogenous LL receptors in HeLa cells can be activated to induce NF-κB/IL-8 and that an edelfosine receptor in HeLa cells can be activated to induce NF-κB/IL-8.

Functional assays were developed to identify receptors as NF-κB inducing receptors, in particular, to identify lysolipid (LL) receptors, EDG receptors and edelfosine receptors. In particular, assays were developed to measure NF-κB, IL-8 or IL-6 production.

With respect to the LL receptor(s) and edelfosine receptor(s), an assay was developed to determine the response of HeLa cells to LL (Including S1P and LPA) and edelfosine, respectively, to induce NF-κB/IL-8 activation/production.

Figure 25:
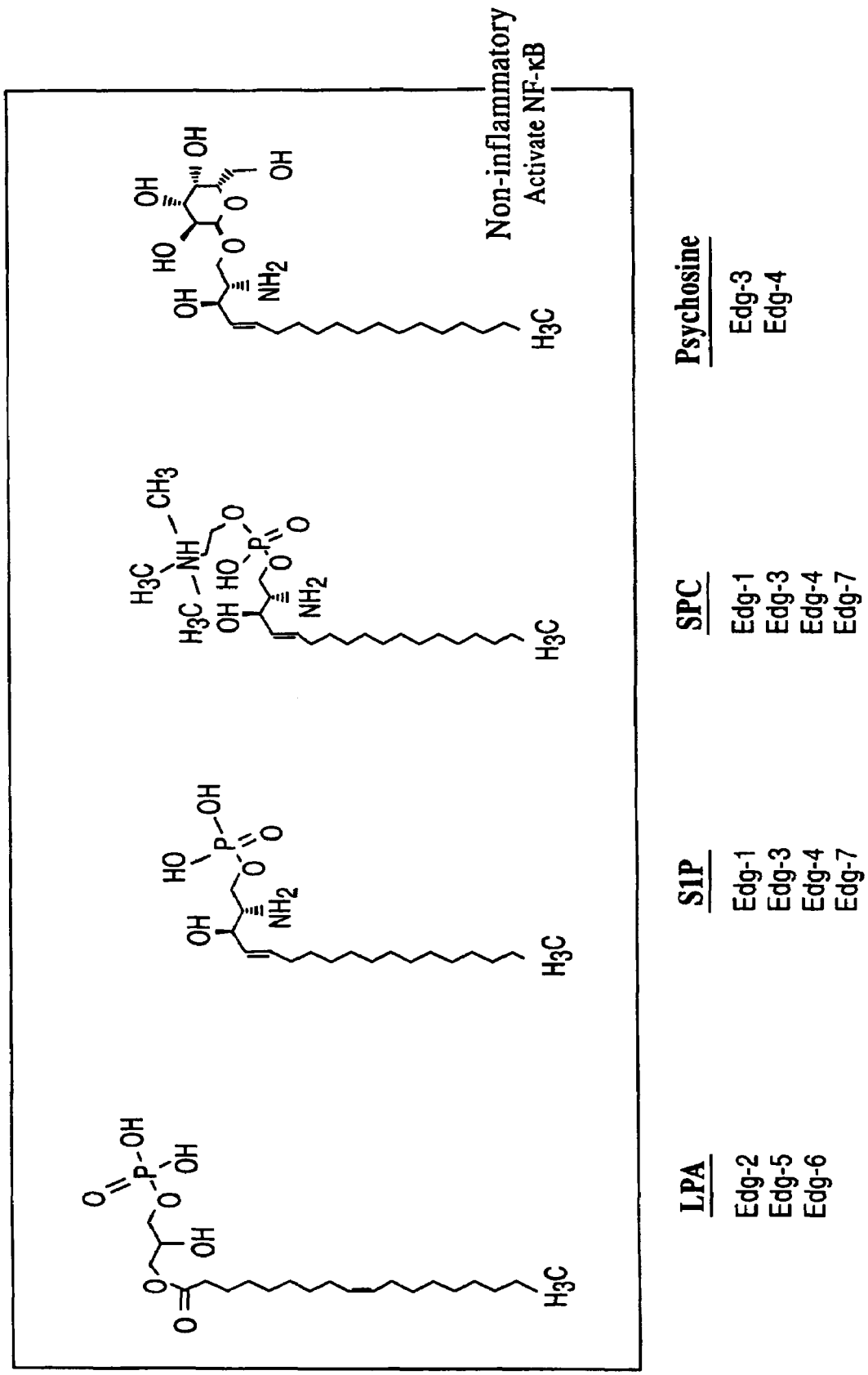
FIG. 25 illustrates edg receptors implicated in the activation of NF-κB.

As exemplified below, 293-EBNA cells were used to transfect EDG receptors. The transfected 293 EBNA cells were then exposed to specific ligands (namely, S1P, SPC and LPA) and NF-κB or IL-8 were measured as an indication of the inflammatory response. Accordingly, using these functional assays, it has now been determined that LPA, S1P and/or SPC bind to EDG-2, EDG-3, EDG-4, EDG-5 and EDG-6 to induce NF-κB and/or IL-8 (See FIG. 25). Since NF-κB and/or IL-8 are products of an inflammatory response pathway and NF-κB is also associated with an anti-apoptotic pathway, EDG-2, EDG3, EDG-4, EDG-5 and EDG-6 are receptors which are linked to these same pathways. Thereby, by modulating these edg receptors or any edg receptors which activate NF-κB, an inflammatory response or apoptosis-modulating signal can be modulated.

The assays described herein are able to identify inflammatory EDG/LL receptors both in heterologous expression and endogenous expression settings, and to aid in their cloning and characterization. Thus, EDG-2, EDG3, EDG-4EDG-5 and EDG-6 were identified herein as inflammatory LL receptors through this approach. Similarly, the determination that edelfosine can provoke a PTX-sensitive IL-8 response in HeLa cells suggests that an edelfosine receptor resides in HeLa cells, which may or may not correspond to an EDG or LL receptor. Isolation of this and other EDG/LL receptors is a straightforward technical exercise, in light of the current disclosure. Given the demostrated clinical effects of edelfosine, a LL-derived anti-neoplastic agent, such isolated receptors and the attendant functional assays offer great scientific, commercial and medical potential.

The non-receptor-dependent actions of LL might be expected to cause cell injury, possibly activating NF-κB without a requirement for a GPCR receptor. Therefore, a parallel assessment of cytotoxicity with functional response was conducted, along with a clear demonstration of time- and concentration-dependence and ligand specificity and an assessement of signal transduction mechanism, in order to validate NF-κB activation as a functional assay for the receptors herein. (See Examples below.)

The invention relates in another respect to polynucleotides, in their isolated form, that encode the human EDG-4 receptor. The activity of EDG-4 receptor can be measured using a variety of appropriate functional assays, some of which are described hereinbelow. More particularly, the EDG-4 receptor is capable of binding with LLs, such as S1P and SPC, for signal transduction to induce NF-κB and IL-8.

As used herein and designated by the upper case abbreviation, EDG, refers to the receptor in either naturally occurring of synthetic form and edg refers to the nucleotide sequence of the receptor. In particular, HEDG-4 refers to the human EDG-4 receptor homolog in either naturally occurring or synthetic form and hedg-4 refers to the nucleotide sequence of the human receptor. The HEDG-4 receptor is activated by S1P and SPC and includes the amino acid sequence of FIG. 16A or 16B and biologically active fragments thereof. More particularly, the HEDG-4 receptors preferably have at least 91% sequence identity with each other, and more preferably at least 95% sequence identity with each other.

Definitions

The following definitions are used herein for the purpose of describing particular terms used in the application. Any terms not specifically defined should be given the meaning commonly understood by one of ordinary skill in the art to which the invention pertains.

As used herein "isolated" means separated from nucleotide sequences that encode other proteins. In the context of polynucleotide libraries, for instance, a hedg-4 receptor-encoding nucleotide sequence is considered "isolated" when it has been selected, and hence removed from association with other nucleotide sequences within the library. Such nucleotide sequences may be in the form of RNA, or in the form of DNA including cDNA, genomic DNA and synthetic DNA.

As used herein "purified" refers to sequences that are removed from their natural environment, and are isolated or separated, and are at least 60% free, preferably 75% free, and most preferably 90% free from other components with which they are naturally associated.

An "oligonucleotide" is a stretch of nucleotide residues, which has a sufficient number of bases to be used as an oligomer, amplimer or probe in a polymerase chain reaction (PCR). Oligonucleotides are prepared from genomic or cDNA sequence and are used to amplify, reveal or confirm the presence of a similar DNA or RNA un a particular cell or tissue. Oligonucleotides or oligomers comprise portions of a DNA sequence having at least about 10 nucleotides and as many as about 35 nucleotides, preferably about 25 nucleotides.

"Probes" may be derived from naturally occurring, recombinant, or chemically synthesized single- or double-stranded nucleic acids or be chemically synthesized. They are useful in detecting the presence of identical or similar sequences.

A "portion" or "fragment" of a nucleotide or nucleic acid sequence comprises all or any part of the sequence having fewer nucleotides than about 6 kb, preferably fewer than about 1 kg. A portion or fragment can be used as a probe. Such probes may be labeled with reporter molecules using nick translation, Klenow fill-in reaction, PCR or other methods well known in the art. To optimize reaction conditions and to eliminate false positives, nucleic acid probes may be used in Southern, Northern or in situ hybridizations to determine whether DNA or RNA encoding HEDG-4 is present in a cell type, tissue, or organ.

"Reporter" molecules are those radionuclides, enzymes, fluorescent, chemiluminescent, or chromogenic agents which associate with, establish the presence of, and may allow quantification of a particular nucleotide or amino acid sequence.

"Recombinant nucleotid variants" encoding HEDG-4 may be synthesized by making use of the "redundancy" in the genetic code. Various codon substitutions, such as the silent changes which produce specific restriction sites or condon usage-specific mutations, may be introduced to optimize cloning into a plasmid or viral vector or expression in a particular prokaryotic or eukaryotic host system, respectively.

"Chimeric" molecules may be constructed by introducing all or part of the nucleotide sequence of this invention into a vector containing additional nucleic acid sequence which might be expected to change any one (or more than one) of the following HEDG-4 characteristics: cellular location, distribution, ligand-binding affinities, interchain effinities, degradation/turnover rate, signaling, etc.

"Biologically Active or Active" refers to those forms, fragments, or domains of any HEDG-4 polypeptide which retain at least some of the biological and/or antigenic activities of any naturally occurring HEDG-4.

"Naturally occurring HEDG-4" refers to a polypeptide produced by cells which have not been genetically engineered and specifically contemplates various polypetides arising from polymorphisms found among human populations, as well as those arising from RNA editing, alternative splicing, or post-translational modifications of the polypeptide including but not limited to acetylation, carboxylation, glycosylation, phosphorylation, lipidation and acylation.

"Derivative" refers to those amino acid sequences and nucleotide sequences which have been chemically modified. Such techniques for polypeptide derivatives include; ubiquitination; labeling (see above); pegylation (derivatization with polyethylene glycol); and chemical insertion or substitution of amino acids such as ornithine which do not normally occur in human proteins. A nucleotide sequence derivative would encode the amino acid which retains its essential biological characteristics of the natural molecule.

"Recombinant polypetide variant" refers to any polypeptide which differs from naturally occurring HEDG-4 by amino acid insertions, deletions and/or substitutions, created using recombinant DNA techniques. Guidance in determining which amino acid residues may be replaced, added or deleted without abolishing activities of interest may be found by comparing the sequence of HEDG-4 with that of related polypeptides and minimizing the number of amino acid sequence changes made in highly conserved regions.

Amino acid "substitutions" are conservative in nature when they result from replacing one amino acid with another having similar structural and/or chemical properties, such as the replacement of a leucine with an isoleucine or valine, an asparate with a glutamate, or a theronine with a serine.

"Insertions" or "deletions" are typically in the range of about 1 to 5 amino acids. The variation allowed may be experimentally determined by producing the peptide synthetcally or by systematically making insertions, deletions, or substitutions of nucleotides in the hedg-4 sequence using recombinant DNA techniques.

A "signal or leader sequence" can be used, when desired, to direct the polypeptide through a membrane of a cell. Such a sequence may be naturally present on the polypetides of the present invention or provided from heterologous sources by recombinant DNA techniques.

An "oligopeptide" is a short stretch of amino acid residues and may be expressed from an oligonucleotide. It may be functionally equivalent to and the same length as (or considerably shorter than) a "fragment", "portion", or "segment" of a polypeptide. Such sequences comprise a stretch of amino acid residues of at least about 5 amino acids and often about 17 or more amino acids, typically at least about 9 to 13 amino acids, and of sufficient length to display biological and/or antigenic activity.

"Inhibitor" is ahy substance which retards or prevents a biochemical, cellular or physiological reaction or response. Common inhibitors include but are not limited to antisense molecules, antibodies, and antagonists.

"Standard" is a quantitative or qualitative measurement for comparison. It is based on a statistically appropriate number of normal samples and is created to use as a basis of comparison when performing diagnostic assays, running clinical trials, or following patient treatment profiles.

"Stringent conditions" is used herein to mean conditions that allow for hybridization of substantially related nucleic acid sequences. Such hybridization conditions are described by Sambrook et al., Molecular Cloning: A Laboratory Manual; 2nd ed., Cold Spring Harbor Press, 1989. Generally, stringency occurs within a range from about 5° C. below the melting temperature of the probe to about 20° C.–25° C. below the melting temperature. As understood by ordinary skilled persons in the art, the stringency conditions may be altered in order to identify or detect identical or related nucleotide sequences. Factors such as the length and nature (DNA, RNA, base composition) of the sequence, nature of the target (DNA, RNA, base composition, presence in solution or immobilization, etc.) and the concentration of the salts and other components (e.g. the presence or absence of formamide, dextran sulfate and/or polyethylene glycol) are consider and the hybridization solution may be varied to generate conditions of either low or high stringency.

"Animal" as used herein may be defined to include human, domestic (cats dogs, etc.), agricultural (cows, horses, sheep, etc.) or test species (mouse, rat, rabit, etc.).

"Nucleotide sequences" as used herein are oligonucleotides, polynucleotides, and fragments or portions thereof, and are DNA or RNA of genomic or synthetic orgin which may be single or double stranded, and represent the sense or complement or antisense strands.

"Sequence Identify" is known in the art, and is a relationship between two or more polypeptide sequences or two or more polynucleotide sequences, as determined by comparing the sequences, particularly, as determined by the match between strings of such sequences. Sequence identify can be readily calculated by known methods (Computational Molecular Biology, Lesk, A. M., ed., Oxford University Press, New York, 1988; Biocomputing; Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity between two sequences, the term is well known to skilled artisans (see, for example, Sequence Analysis in Molecular Biology; Sequence Analysis Prime; and Carillo, H., and Lipman, D., SIAM J. Applied Math., 48: 1073 (1988)). Methods commonly employed to determine identity between sequencews include, but are not limited to those disclosed in Carillo, H., and Lipman, D., SIAM J. Applied Math., 48: 1073 (1988) or, preferably, in Needleman and Wunsch, J. Mol. Biol., 48: 443–445, 1970, wherein the parameters are as set in version 2 of DNASIS (Hitachi Software Engineering Co., San Bruno, Calif.). Computer programs for determinins identify are publicly available. Preferred computer program methods to determine identity between two sequences include, but are not limited to, GCG program package (Devereux, J., et al., Nucleic Acids Research 12(1):387 (1984)), BLASTP, BLASTN, and FASTA (Atschul, S. F. et al., J. Molec. Biol 215:403–410 (1990)). The BLASTX program is publicly available from NCBI (blast@ncbi.nlm.nih.gov) and other sources (BLAST Manual, Altschul, S., et al., NCBI NLM NIH Bethesda, Md. 20894; Altschul, S., et al., J. Mol. Bio. 215:403–410 (1990)). Computational Molecular Biology, Lesk, A. M., ed. Unless specified otherwise in the claims, the percent identity for the purpose of interpreting the claims shall be calculated by the Needleman and Wucnsch algorithm with the parameters set in version 2 of DNASIS.

The EDG receptor family of T7G receptors has been subdivided into 2 subgroups on the basis of sequence similarity and genomic organization (Chun, Contos & Munroe, in press). We have determined that EDG-2, EDG-5 (see U.S. Ser. No. 08/997,803, incorporated herein by reference) and EDG-6 (Genbank Accession AF011466) respond to LPA as an agonist, and share a common intron structure within their coding redions. EDG-1, EDG-3, rat EDG-4/H218 (Accession U10699) and EDG-7 (see co-pending U.S. patent application Ser. No. 60/070,184) have intronless coding regions and respond to S1P and SPC as agonists. The present T7G receptor, HEDG-4, has no intron within the coding region.

One aspect of the present invention is a method for using recombinant HEDG-4 receptors in an assay for screening ligands and potential drug candidates. Although the use of T7G receptors in high-throughout screening is well-known, no such screen has been reported for the HEDG-4 receptor. More specifically, the novel HEDG-4 receptor presented therein can be used to identity and rank the relative potency and efficacy of potential agonists. These compounds may be useful in as much as they would be expected to modulate cellular or physiological responses to HEDG-4 agonists, or to initiate or supplement HEDG-4 signaling in cells were the receptor occurs. Equally, once a quantitative and reliable assays is established, it can readily be applied to identify and rank the relative potency and efficacy of receptor antagonists. This application, without limiting other aspects, of the screening methods described herein is specifically contemplated and incorporated within the scope of this invention.

It was determined that S1P and SPC are agonists for HEDG-4.

Other HEDG-4 ligands are likely to be found among the phospholipid class of compounds. Therefore, in one embodiment, phospholipid molecules could be screened to identify ligands. Particularly, it is believed that potential ligands include fatty acid chains of differing length, such as 16, 17, 18, 19, 20, 22 and 24 carbon units, with or without 1, 2, 3 or 4 unsaturated carbon-carbon bonds.

The nucleotide sequences encoding HEDG-4 (or their complement) have numerous applications in techniques known to those skilled in the art of molecular biology. These techniques include use as hybridization probes, use in the construction of oligomers for PCR, use for chromosome and gene mapping, use in the recombinant production of HEDG-4, and use in generation of antisense DNA or RNA, their chemical analogs and the like. Uses of nucleotides encoding HEDG-4 disclosed herein are exemplary of known techniques and are not intended to limit theri use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of hedg-4 encoding nucleotide sequences may be produced. Some of these will only bear minimal homology to the nucleotide sequence of the known and naturally occurring hedg-4. The invention has specifically comtemplated each and every possible variation of nucleotide sequence that could be made by selecting comginations based on possible codon choices. These combinations are made in accordance with the standard triplet genetic code as applied to the nucleotide sequence of naturally occurring hedg-4, and all such variations are to be considered as being specifically disclosed.

Although the nucleotide sequences which encode HEDG-4, its derivatives or its variants are preferably capable of hybridizing to the nucleotide sequence of the naturally occurring hedg-4 under stringent conditions, it may be advantageous to produce nucleotide sequences encoding HEDG-4 or its derivatives possessing a substantially different condon usage. Condons can be selected to increase the rate at which expression of the peptide occurs in a particular prokaryotic or eukaryotic expression host in accordance with the frequency with which particular condons are utilized by the host. Other reasons for substantially altering the nucleotide sequence encoding HEDG-4 and/or its derivatives without altering the encoded amino acid sequence include the production of RNA transcripts having more desirable properties, such as a greater half-life, than transcripts produced from the naturally occurring sequence.

Human genes often show considerable actual polymorphism; that is , variation in nucleotide sequence among a fraction of the entire human population. In many cases this polymorphism can result in one or more amino acid substitutions. While some of these substitutions show no demonstrable change in function of the protein, others may produce varying degrees of functional effects. In fact, many natural or artifically produced mutations can lead to expressible HEDG proteins. Each of these variants, whether naturally or artificially produced is considered to be equivalent and specifically incorporated into the present invention.

Nucleotide sequences encoding HEDG-4 may be joined to a variety of other nucleotide sequences by means of well established recombinant DNA techniques (Sambrook J et al (1989) Molecular Cloning: A Laboratory Manual, Cold Spring Harbor Laboratory, Cold Spring Harbor N.Y.; or Ausubel FM et al (1989) Current Protocols in Molecular Biology, John Wiley & sons, New York City). Useful nucleotide sequences for joining to hdg-4 include an assortment of cloning vectors such as Plasmids, cosmids, lambda phage derivatives, phagemids, and the like. Vectors of interest include expression vectors, replication vectors, probe generation vectors, sequencing vectors, etc. In general vectors of interest may contain an orgin of replication functional in at least one organism, convenient restriction endonuclease sensitive sites, and selectable markers for one or more host cell systems.

Another aspect of the subject invention is to provide for hedg-4 specific hybridization probes capable of hybridizing with naturally occurring nucleotide sequences encoding HEDG-4. Such probes may also be used for the detection of similar T7G encoding sequences and should preferably contain at least 91% nucleotide identity to hedg-4 sequence and more preferably at least 95% identity. The hybridization probes of the subject invention may be derived from the nucleotide sequence presented in the figures for hedg-4 or from genomic sequences including promoter, enhancers, introns or 3'-untranslated regions of the native gene. Hybridization probes may be labeled by a variety of reporter molecules using techniques well known in the art. Preferably, the hybridization probes incorporate at least 15 nucleotides, and preferably at least 25 nucleotides, of the hedg-4 receptor.

It will be recognized that many deletional or mutational analogs of nucleic acid sequences for HEDG-4 will be effectivehybridization probes for HEDG-4 nucleic acid. Accordingly, the invention relates to nucleic acid sequences that hybridize with such HEDG-4 encoding nucleic acid sequences under strigent conditions.

Stringent conditions will generally allow hybridization of sequence with at least about 70% sequence identity, more preferably at least about 80–85% sequence identity, even more preferably at least about 90% sequence identity, and most preferably with at least about 95% sequence identity Hybridization conditions and probes can be adjusted in well-characterized ways to achieve selective hybridization of human derived probes, Nucleic acid molecules that will hybridize to HEDG-4 encoding nucleic acid under stringent conditions can be identified functionally, using methods outlined above, or by using for example the hybridization rules reviewed in Sambrook et al., Molecular Cloning: A Laboratory Manual, 2nd ed., Cold Spring Harbor Pres;, 1989. Without limitation, examples of the uses for hybridization probes include: histochemical user such as identifying tissues that express HEDG-4; measuring mRNA levels, for instance to identify a sample's tissue type or to identify cells that express abnormal levels of HEDG-4, and detecting polynotphisms in the HEDG-4. RNA hybridization procedures are described in Maniatis et al. Molecular Cloning, a Laboratory Manual (Cold Spring Harbor Press, 1989). PCR as described U.S. Pat. Nos. 4,683,195; 4,800,195; and 4,965,188 provides additional uses for oligonucleotides based upon thee nucleotide sequence which encodes the EDG-4 sequences of the invention. Such probe used PCR may be of recombinant origin, chemically synthesized, or a mixture of both. Oligomers may comprise discrete nucleotide sequences employed under optimized conditions for identification of hedg-4 in specific tissues or diagnostic use. The same two oligomers, a nested set of oligomers, or even a degenerate pool of oligomers may be employed under less stringent conditions for identification of closely related DNA's or RNA's. Rules for designing PCR primers are now established, as reviewed by PCR Protocols, Cold Spring Harbor Press, 1991. Degenerate primers, i.e., preparations of primers that are heterogeneous at given sequence locations, can be designed to amplify nucleic acid sequences that are highly homologous to, but not identical to hedg4. Strategies are now available that allow for only one of the primers to be required to specifically hybridize with a known sequence. See, Froman et al., Proc. Natl. Acad. Sci. USA 85; 8998, 1988 and Loh et al., Science 243: 217, 1989. For example, appropriate nucleic acid primers can be ligated to the nucleic acid sought to be amplified to provide the hybridization partner for one of the primers. In this way, only one of the primers need be based on the sequence of the nucleic acid sought to be amplified, PCR methods of amplifying nucleic acid will utilize at least two primers. One of these primers will be capable of hybridizing to a first strand of the nucleic acid to be amplified and of priming enzyme-driven nutleic acid synthesis in a first direction. The other will be capable of liybridizing the reciprocal sequence of the first strand (if the sequence to be amplified is single stranded, this sequence will initially be hypothetical, but will be synthesized in the first amplificaiton cycle) and of priming nucleic acid synthesis from that strand in the direction opposite the first direction and towards the site of hybridization for the first primer. Conditions for conducting such amplifications, particularly under preferred stringent hybridization conditions, are well known. See for example, PCR Protocols, Cold Spring Habor Press, 1991.

Other means of producing specific hybridization probes for hedg-4 include the cloning of nucleic acid sequences encoding HEDG-4 or HEDG-4 derivatives into vectors for the production of mRNA probes. Such vectors are known in the art, are commercially available and may be used to synthesize RNA probes in vitro by means of the addition of the appropriate RNA polymerase as T7 or SP6 RNA polymerase and the appropriate reporter molecules.

It is possible to produce a DNA sequence, or portions thereof, entirely by synthetic chemistry. After synthesis, the nucleic acid sequence cam be inserted into any of the many available DNA vectors and their respective host cells using techniques which are well known in the art. Moreover, synthetic chemistry may be used to introduce mutations into the nucleotide sequence. Alternately, a portion of sequence in which a mutation is desired cam be synthesized and recombined with longer portion of an existing genomic or recombinant sequence.

The nucleotide sequence for hedg-4 can be used in an assay to detect inflammation or disease associated with abnormal levels of HEDG-4 expression. The cDNA can be labeled by methods known in the art, added to a fluid, cell or tissue sample from a patient, and incubated under hybridizing conditions. After an incubation period, the sample is washed with a compatible fluid which optionally contains a reporter molecule. After the compatible fluid is rinsed off, the reporter molecule is quanitated and compared with a standard as previously defined.

A diagnostic test for aberrant expression of HEDG-4 can accelerate diagnosis s and proper treatment of abnormal conditions of for example the heart, kidney, lung and testis. Specific examples of conditions in which aberrant expression of HEDG-4 may play a role include adult respiratory distress, asthma, rheumatoid arthritis, cardiac ischemia, acute pancreatitis, septic shock, psoriasis, acute cydlosporine nephtotoxicity and early diabetic glomerulopathy, as well as lung damage following exposure to cigarette smoke, asbestos or silica.

Nucleotide sequences encoding hedg-4 may be used to produce a purified oligo—or polypeptide using well known methods of recombinant DNA technology. Goeddel (1990, Gene Expression Technology, Methods and Enzmology, Vol. 185, Academic Press, San Diego Calif.) is one among many publications which teach expression of an isolated nucleotide sequence. The oligopeptide may be expressed in a variety of host cells, either prokaryotic or eukatyotic. Host cells may be from the same species from which the nucleotide sequence was derived or from a different species. Advantages of producing an oligonucleotide by recombinant DNA technology include obtaining adequate amounts of the protein for purification and the availability of simplified purification procedures.

Cells transformed with DNA encoding HEDG-4 may be cultured under conditions suitable for the expression of T7Gs, their extracellular, transmembrane or intracellular domains and recovery of such peptides from cell culture. HEDG-4 (or any of its domains) produced by a recombinant cell may be secreted, expressed on cellular membranes or may be contained intracellularly, depending on the particular genetic construction used. In general, it is more convenient to prepare recombinant proteins in secreted form. Purification steps vary with the production process and the particular protein produced. Often an oligopeptide can be produced from a chimeric nucleotide sequence. This is accomplished by ligating the nucleotides from hedg-4 or desired portion of the polypeptide to a nucleic acid sequence encoding a polypeptide domain which will facilitate protein purification (Kroll D J et al (1993) DNA Cell Biol. 12:441–53)

In addition to recombinant production, fragments of HEDG-4 may be produced by direct peptide synthesis using solid-phase techniques (e.g. Stewart at al (1969) Solid-Phase Peptide Synthesis, W H Freeman Co., San Francisco QA Merrifield J (1963) J Am Chem. Soc. 85:2149–2154). Automated synthesis may be achieved, for example, using Applied Biosystems 431A Peptide Synthesizer (Foster City, Calif.) in accordance with the instructions provided by the manufacturer. Additionally, a particular portion of HEDG-4 may be mutated during direct synthesis and combined with other parts of the peptide using chemical methods.

HEDG-4 for antibody induction does not require biological activity; however, the protein must be antigenic. Peptides used to induce specific antibodies may have an as sequence consisting of at least five amino acids (aa), preferably at least 10 aa. They should mimic a portion of the as sequence of the protein and may contain the entire as sequence of a small naturally occurring molecule such as HEDG-4. An antigenic portion of HEDG-4 may be fused to another protein such as keyhole limpet hemocyanin, and the chimeric molecule used for antibody production.

Antibodies specific for HEDG-4 may be produced by inoculation of an appropriate animal with the polypeptide or an antigenic fragment. An antibody is specific for HEDG-4 it is produced against an epitope of the polypeptide and binds to at least part of the natural or recombinant protein. Antibody production includes not only the stimulation of an immune response by injection into animals, but also analogous processes such as the production of synthetic antibodies, the screening of recombinant immunoglobulin libraries for specific-binding molecules (e.g. Orlandi R et al (1989) PNAS 86:3833–3837, or Huse W D et al (1989) Science 256:1275–1281) or the in vitro stimulation of lymphocyte populations. Current technology (Winter G and Mistein C (1991) Nature 349:293–299) provides for a number of highly specific binding reagents based on the principles of antibody formation. These techniques may be adapted to produce molecules which specifically bind HEDG-4s.

An additional embodiment of the subject invention is the use of HEDG-4 specific antibodies, inhibitors, ligands or their analogs as bioactive agents to treat inflammation or disease including, but not limited to viral, bacterial or fungal infections; allergic responses; mechanical injury associated with trauma; hereditary diseases; lymphoma or carcinoma; or other conditions which activate the genes of kidney, lung, heart lymphoid or tissues of the nervous system.

Bioactive compositions comprising agonists, antagonists, receptors or inhibitors of HEDG-4 may be administered in a suitable therapeutic dose determined by any of several methodologies including clinical studies on mammalian species to determine maximal tolerable dose and on normal human subjects to determine safe dose. Additionally, the bioactive agent may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating problems involving aberrant expression of the EDG-4 gene.

All publications and patent applications mentioned herein are incorporated by reference for the purpose of describing the methodologies, cell lines and vectors, among other things. However, nothing herein is to be construed as an admission that the invention is not entitled to antedate such disclosure, for example, by virtue of prior invention.

The examples below are provided to illustrate the subject invention. These examples are provided by way of illustration and are not included for the purpose of limiting the invention.

EXAMPLE 1

IL-8 Response to S1P in HeLa cells is Concentration and Time Dependent

Figure 1A:
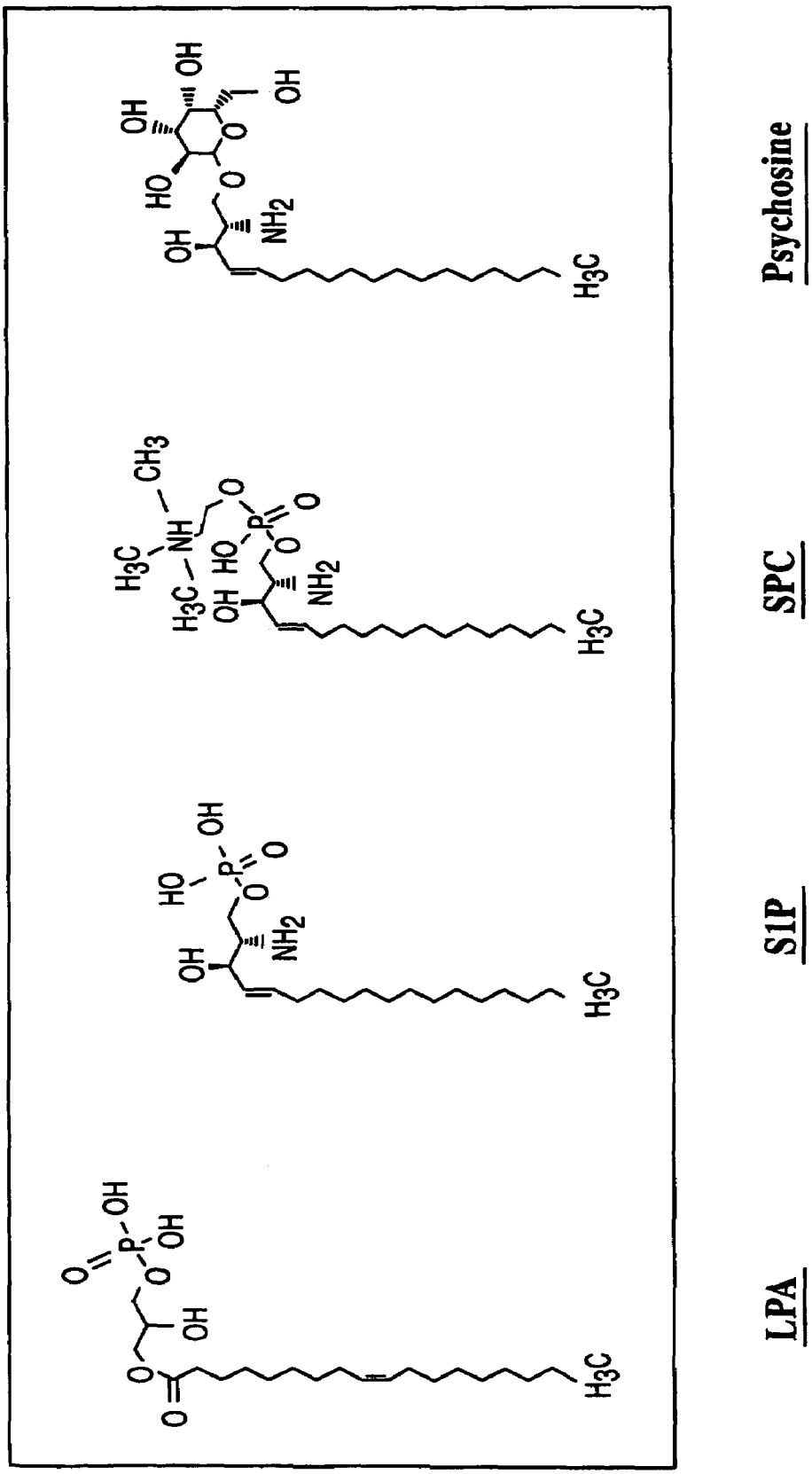
FIG. 1A illustrates the chemical structure of LPA, S1P, SPC and pyschosine.
Figure 1B:
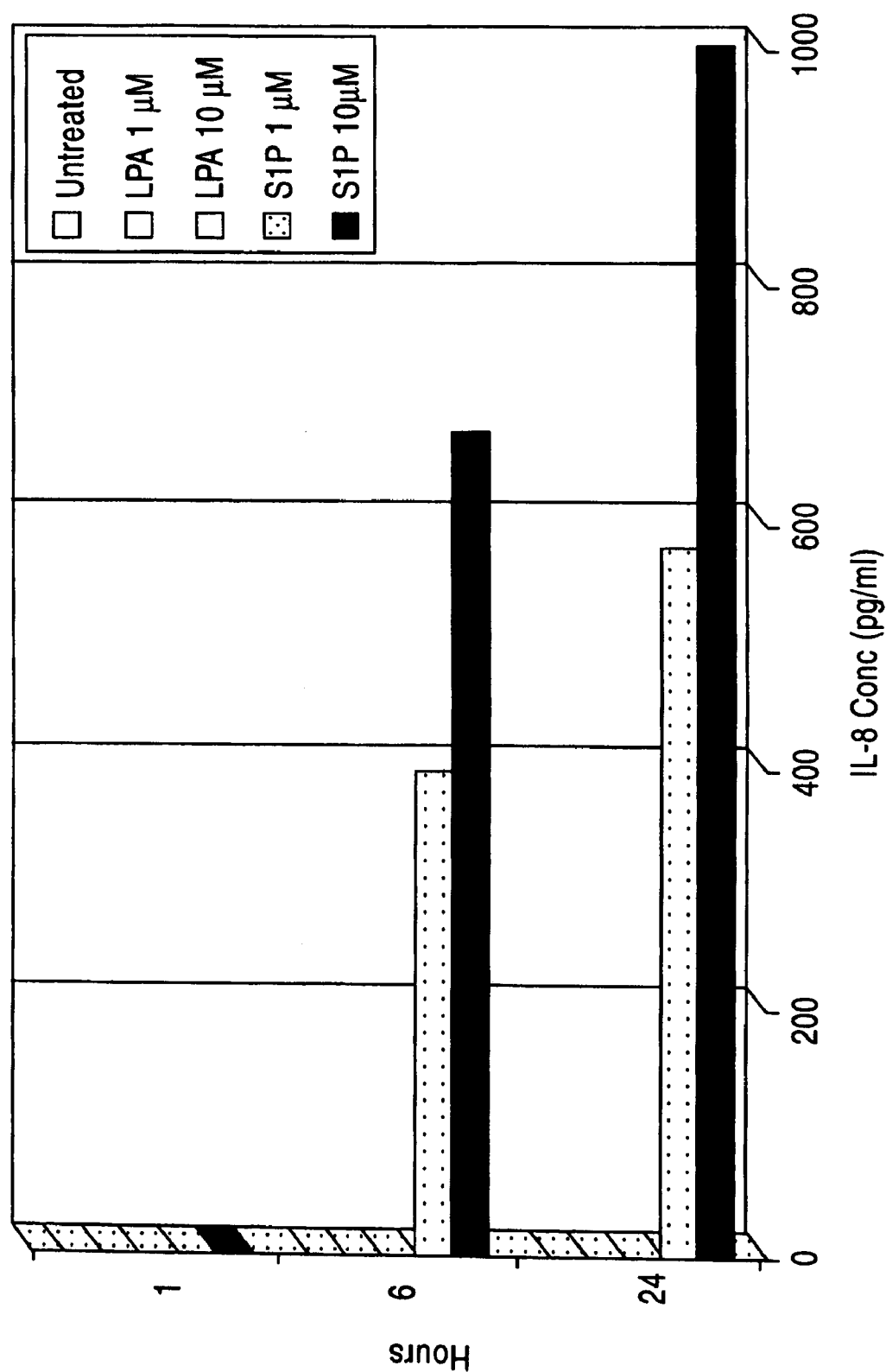
FIG. 1B illustrates the time and concentration-dependent IL-8 response to S1P and LPA in HeLa cells.
Figure 5:
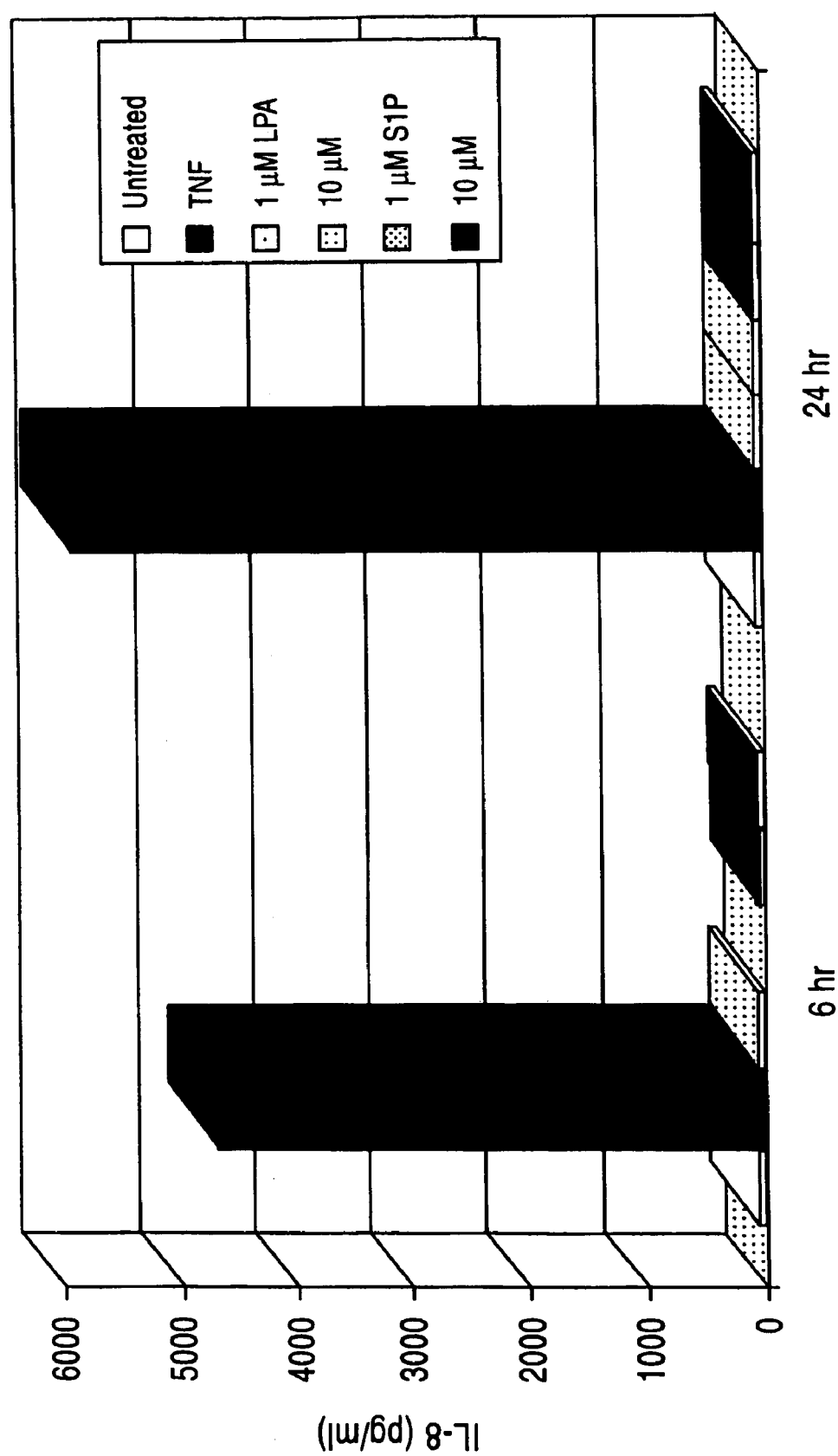
FIG. 5 illustrates the time and concentration-dependent IL-8 response to TNF-α, S1P and LPA in HL-60 cells.

A preliminary survey of cell lines for IL-8 and IL-6 response to S1P identified HeLa cells as a potential responder (FIG. 1B), while HL-60 cells were unresponsive, consistent with the reported lack of S1P receptors in these cells (FIG. 5). IL-8 and IL-6 are potently induced by a variety of proinflammatory agents, including TNF-α, phorbol ester (TPA) and ultraviolet radiation. Induction by these agents is dependent on transcriptional upregulation by NF-κB, although NF-IL6 and AP-1 also play roles in certain experimental models. Because commercially available IL-8 ELISA kits offer a robust and simple measurement with moderately high throughput, we chose to focus on the IL-8 response in the first instance. Later work included the NF-κB reporter gene. However, since the novelty and utility of this invention broadly encompasses inflammatory signaling by edg/LL receptors, we include other receptor-dependent proinflammatory reporters, including, but not limited to NF-κB, NF-IL6 and AP-1 activation are within the scope of the present invention.

Procedure #1 For HeLa Cells:

A. Seeding Cells and Cell Plating Density

Cells: HeLa (adenocarcinoma, human)

Media: DMEM/F12+10% FBS Adherent

1) Cells were seeded at $0.2 \times 10^6$ cells/well in 6-well plates.
2) Confluency of cells after 24–32 hrs was between 60–70%.

B. Overnight Serum-Starvation

1) Media was aspirated (no PBS wash).
2) 1.5 ml 0.5% FBS media was added to each well.

C. Treatments and Collection

1) Made up all required solutions in 0.5% FBS media (control). Handling of LL for use in NF-κB experiments requires that sonication, commonly used to resuspend LPA, not be done; NF-κB may be activated by lipid peroxides created through vigorous frothing.

Solutions:

| | | |
|---|---|---|
| TPA 100 ng/ml | Stock 0.1 mg/ml in DMSO Dilution 1:1000 | Sigma, Cat. P-1585 |
| LPA 10 μM | Stock 10 mM in 0.2% Albumin Bovine in PBS; Dilution 1:1000 | Sigma, Cat. A-0281 |
| LPA 1 μM | Dilute 10 μM 1:10 | |
| S1P 10 μM | Stock 10 mM in methanol Dilution 1:1000 | Sigma, Cat. S-9666 |
| S1P 1 μM | Dilute 10 μM 1:10 | |

Note: All stock solutions are dissolved by pipetting and stored at −20° C.

2) Media was aspirated.
3) 1.5 ml appropriate treatments were added to each well.
4) All plates were placed at 37° C./5% $CO_2$ for either 1, 6, or 24 hours.
5) After the specified time cell supernatants were collected into 1.5 ml eppendorf tubes, spun down at 14000 rpm for 5 minutes and stored at −20° C. for later ELISA determination.

D. Detection of Interleukin-8 (IL-8) using an IL-8 ELISA (Enzyme-Linked ImmunoSorbent Assay).

1) The Quantikine Human IL-8 Immuno Assay Kit was obtained from R&D Systems (Cat. D8050).
2) The kit and all samples were allowed to equlibrate to room temperature prior to use.
3) All reagents were provided in the kit and prepared according to the instructions provided.
4) The assay procedure was followed as recommended in the kit for cell culture supernatant samples.
5) ELISA was performed on 50 μl samples of culture supernatant and duplicate samples were measured for each well. Each treatment was performed on triplicate wells.
6) Plates were read on UV max kinetic microplate reader (Molecular Devices), set to 450 nm and correction set to 575 nm, using Wsoftmax sotware version 2.34.

Results: This experiment showed a time- and concentration-dependent IL-8 response to S1P, but not LPA, in HeLa cells (see FIG. 1B).

EXAMPLE 2

S1P and SPC Both Induce a Concentration-dependent, PTX-sensitive IL-8 Response in HeLa Cells S1P and SPC both show PTX-sensitive functional responses in certain cell types. However, in some cell types S1P shows 10-fold or higher potency than SPC, while in other cell types S1P and SPC are roughly equipotent. If the IL-8 response to S1P and SPC is receptor-mediated, we might expect to see PTX-sensitivity with both ligands and possibly, an equal or reduced potency with SPC.

Procedure #2 For HeLa Cells:

A. Seeding Cells and Cell Plating Density

| | |
|---|---|
| Cells: HeLa (adenocarcinoma, human) | Media: DMEM/F12 + 10% FBS adherent cells |

1) Cells were seeded at $2.5 \times 10^4$ cells/well in 24-well plates.
2) Confluency of cells after 24–32 hrs was between 60–70%.

B. Overnight Serum-Starvation and PTX Pre-Treatment
1) Media was aspirated (no PBS wash).
2) 0.5 ml 0.5% FBS media was added to all wells not requiring PTX pre-treatment.
3) For well requiring PTX; 0.5 ml 0.5% FBS media containing 50 ng/ml PTX (1 volume PTX (RBI Cat. P140): 1 volume DTT, incubate 37° C. for 30 minutes then dilute to 50 ng/ml) was added.

C. Treatments and Collection
1) Made up all required solutions in 0.5% FBS media (control).

Solutions:

S1P 3, 10, 30, 100, 300, 1000, 3000, 10000 nM
SPC 10 μM Stock 10 mM in methanol Sigma, Cat. S-4257 Dilution 1:1000
SPC 1, 3, 10, 30, 100, 300, 1000, and 3000 nM
2) Media was aspirated.
3) 0.5 ml appropriate treatments were added.
4) All plates were placed at 37° C./5% $CO_2$ for 6 hours.
5) After the specified time cell supernantants were collected into 1.5 ml eppendorf tubes, spun down at 14000 rpm for 5 minutes and stored at −20° C. for later ELISA determination.

D. Refer to Procedure #1 For HeLa Cells (D).

Figure 2A:
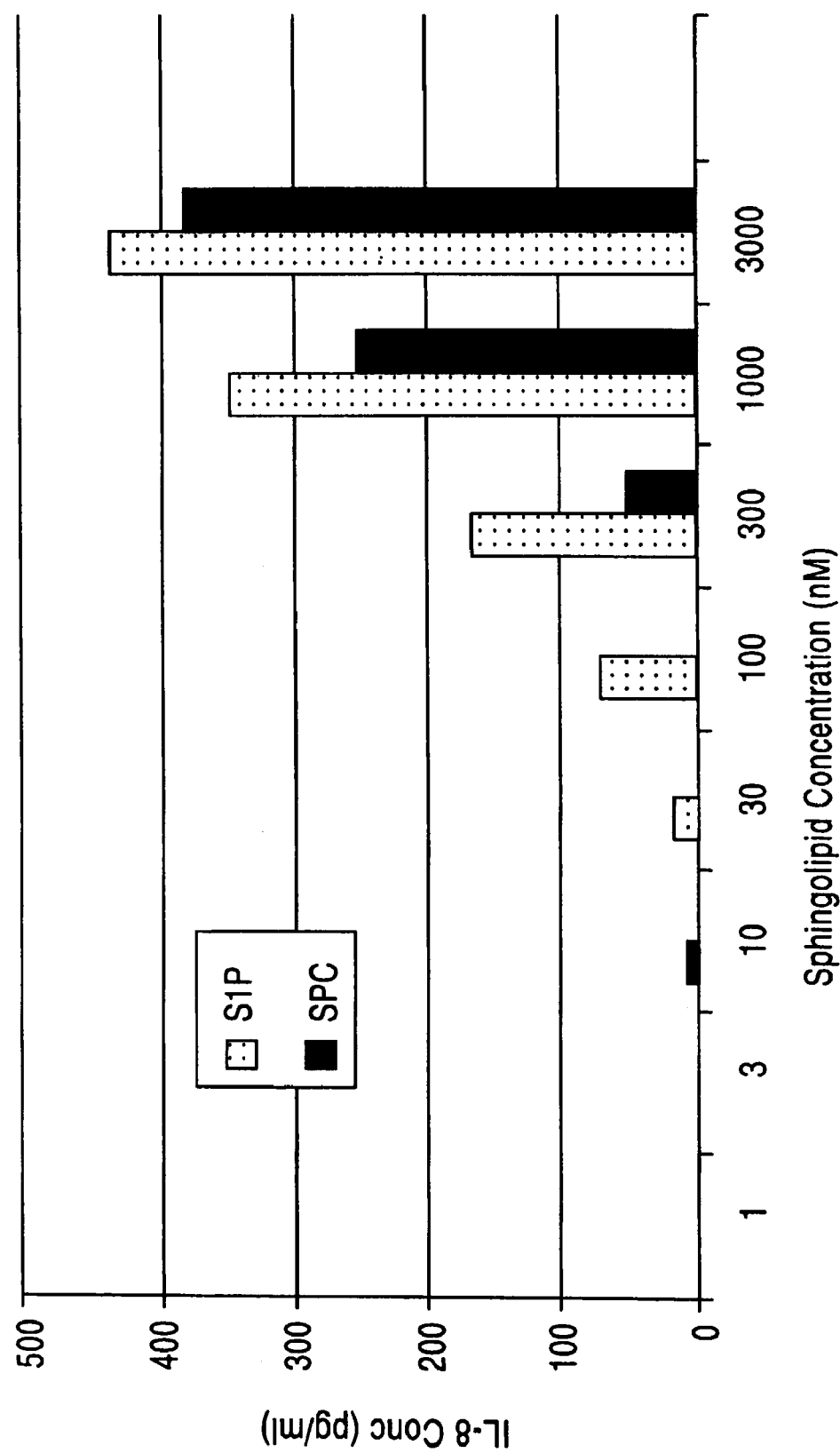
FIG. 2A illustrates the concentration dependent IL-8 response to S1P and SPC HeLa cells.
Figure 2B:
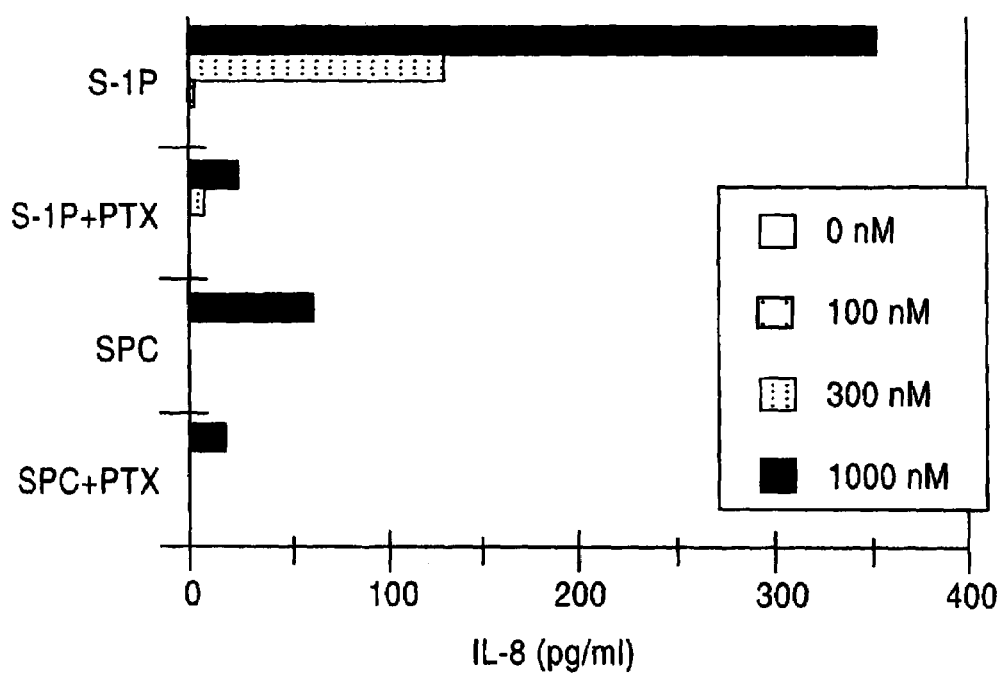
FIG. 2B issustrates the concentration-dependent IL-8 response to S1P and SPC in HeLa cells and the PTX-sensitivity of this response.

Results: The experiment demonstrated unequivocally that both S1P and SPC can induce IL-8 in HeLa cells in a concentration-dependent manner (FIG. 2A), and that these responses are PTX-sensitive, as expected of a $G_i$-coupled receptor (see FIG. 2B).

EXAMPLE 3

Effect of PTX on IL-8 Response to S1P and TNF-α in HeLa cells

Effects of PTX toxin reflet a requirement fo the $G_{i/o}$ family of heterotrimeric G proteins, which play critical roles in the multiple actions of GPCRs. It is possible, however, that the PTX inhibition of S1P induced IL-8 response reflects an indirect effect on downstream signal transduction events, rather than an effecton the G proteins directly coupled to a GPCR for S1P. If a general block of IL-8 production is produced by PTX in HeLa cells, then IL-8 production by TNF-α should also be inhibited. TNF-α induces IL-8 through its own receptor, which is not a GPCR and does not require $G_{i/o}$ for signaling. On the other hand, if the IL-8 response to TNF-α is unaffected ,then the blockade by PTX is specific to S1P but not TNF-α signaling pathways.

Procedure #3 For HeLa Cells:

Follow Procedure 190 2 for HeLa Cells with the following Exceptions:
1) Solutions required in section C are as follows:

S1P 5 μM

| TNF-α 50 ng/ml | Stock 10 μg/ml in 0.1% Albumin Bovine (Albumin: Sigma; Cat. A-0281) in PBS Dilute 1:200 | R&D, Cat. 210-TA |

Figure 3:
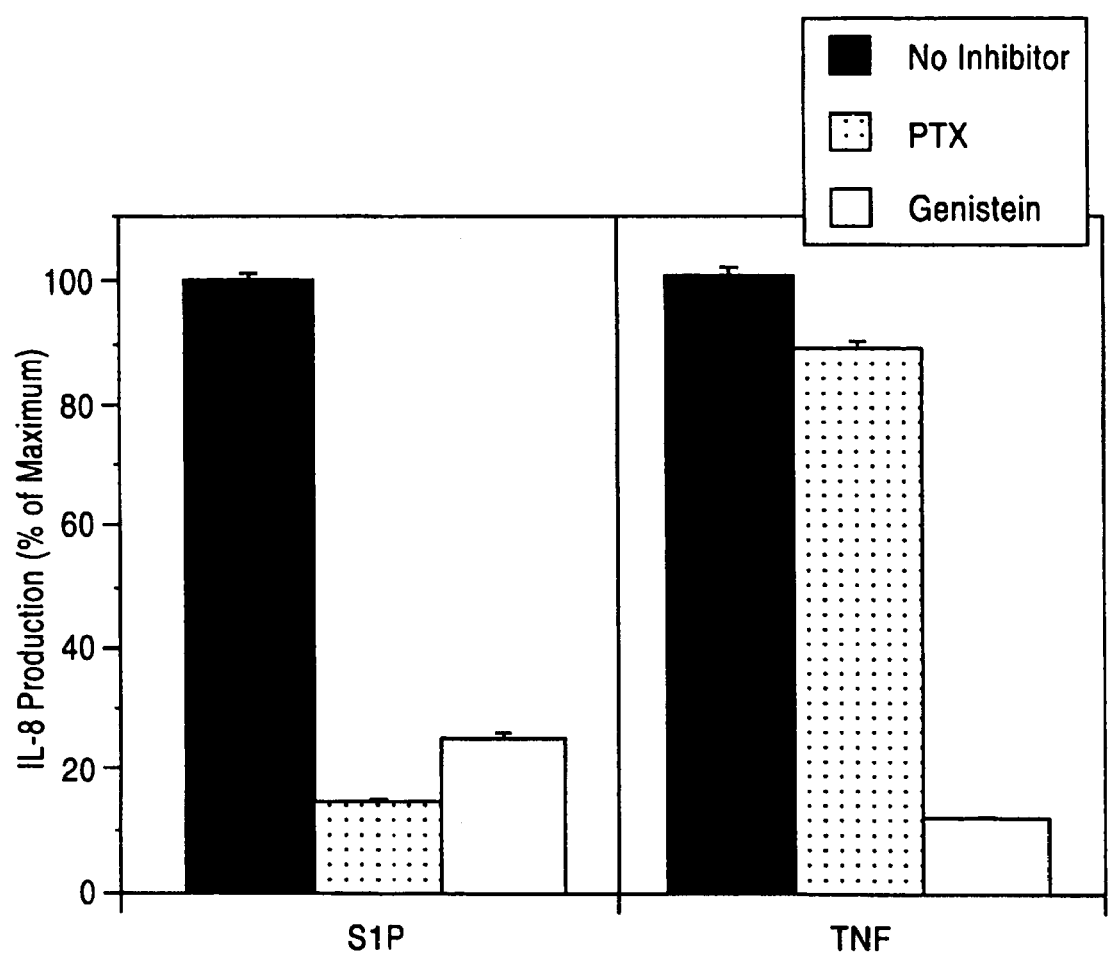
FIG. 3 illustrates the IL-8 response to S1P and TNF-α in HeLa cells and the PTX- and genistein sensitivity of this response.

Results: The results clearly showed that while PTX potently blocked the IL-8 response to S1P, the response to TNF-α was not significantly affected (see FIG. 3). Thus $G_{i/o}$ pathways are required for S1P signaling that leads to the IL-8 response in HeLa cells.

EXAMPLE 4A

IL-8 Response to S1P in HeLa Cells is Ligand-selective and not a general LL response S1P shares a detergent-like structute with many other LL. (See FIG. 1A) Thus, non-specific activation of NF-κB by cell injury or membrane actions of S1P should be produced by many other LL as well. Additionally, any general non-selective LL receptor expressed in HeLa should be activated interchangeably by several different LL. Alternatively, ligand-selective activation of NF-κB argues for a receptor-mediated mechanism amenable to future drug discovery.

Procedure 190 4 For HeLa Cells:

Follow Procedure 190 2 For HeLa Cells with the following Exceptions:
1) No PTX Pre-Treatment is required in section B.
2) Solutions required in section C are as follows:

| LPC | Stock 10 mM in methanol | Sigma, Cat. L-1381 |
| LPE | Stock 10 mM in chloroform | Sigma, Cat. L-4754 |
| LPG | Stock 10 mM in methanol | Sigma, Cat. L-4525 |
| LPI | Stock 10 mM in 1% Albumin Bovine in PBS | Sigma, Cat. L-7635 |
| LPS | Stock 10 mM in 0.2% Albumin Bovine in PBS | Sigma, Cat. L-5772 |
| Lyso-PAF | Stock 10 mM in 1% Albumin Bovine in PBS | Sigma, Cat. L-7890 |
| Lysosulfatide | Stock 10 mM in DMSO | Sigma, Cat. L-3640 |
| Sphingosine | Stock 10 mM in methanol | Sigma, Cat. S-6136 |
| Sphingomyelin (SM) | Stock 10 mM in methanol | Sigma, Cat. S-7004 |

Concentrations for LPC, LPE, LPG, LPS, sphingosine and SM used were 10, 50, 100, 1000, and 5000 nM. Concentrations for LPI, lyso-PAF and lysosulfatide used were 0.3 and 3 μM.

Figure 4A:
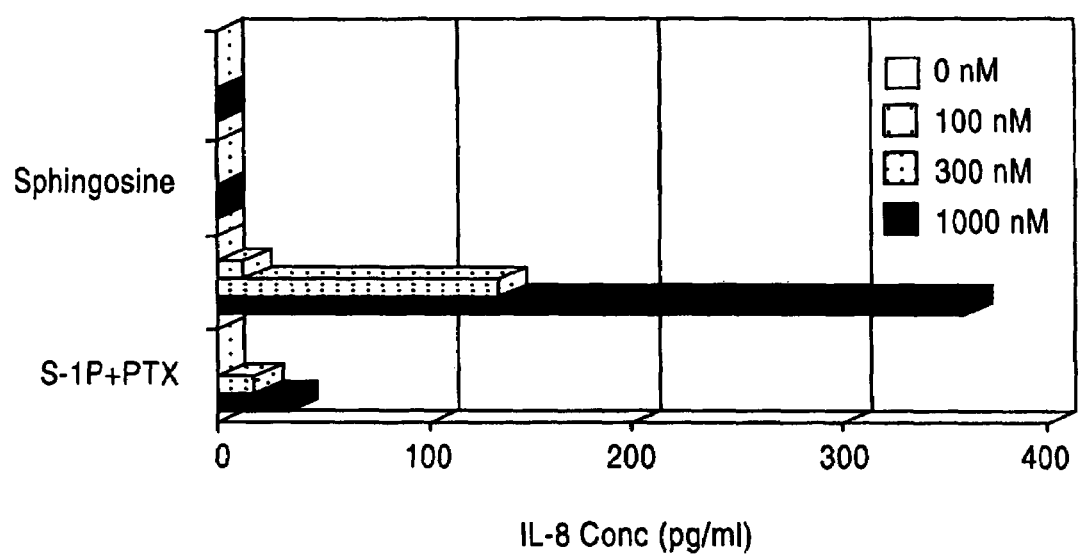
FIG. 4A illustrates the concentration-dependent IL-8 response to S1P, sphingosine and sphigomyelin in HeLa cells.

Results: Only S1P and SPC significantly induced IL-8 production, strongly suggesting that a ligand-selective receptor mediated the PTX-sensitive IL-8 response pathway. While sphingosine is shown together with S1P as examples of the ligand-selectively of the IL-8 response, a similar lack of response was observed in HeLa cells with all other compounds listed above, but not shown on the graph (see FIG. 4A).

EXAMPLE 4B

IL-8 Response to S1P, LPA and Other Lysolipids in Primary Cultured Human Umbilical Vein Endothelial Cells (HUVBC)

While HeLa cells from the basis of and experimentally homogenous assay system, these cells have been carried continuously in culture for many years. Moreover, they are a transformed (i.e. Neoplastic) cell line, and as such, carry many chromosomal and genetic abnormalities. As will be readily apparent to one skilled in cell and molecule biology, findings in HeLa cells should be confirmed in a nontransformed cell line, preferably primary cultured human cells. We chose HUVEC, a commonly available human primary cell culture. Since these cells are derived from the endothelium lining the umbilical vein, they share many characteristics and response pathways with endothelial cells found elsewhere in the human body. More particularly, HUVEC cells have been used for the study of NF-κB activation by GPCRs (Ishizuka T, et al Stimulation with thromboxane A2 (TXA2) receptor agonist enhances ICAM-1 VCAM1 or ELAM-1 expression by human vascular endothelial cells. Clin Exp Immunol. 1998 Jun; 112 (3):464–470; Munoz C, et al Pyrrolidine dithlocarbamate inhibits the production of interleukin-6, interleukin-8, and granulocyte macrophage colony-stimulating factor by human endothelial in response to inflammatory mediators: modulation of NF-κB and AP-1 transcription factors activity. Blood. 1996 Nov 1;88(9);3482–3490.). Among the documented consequences of NF-κB activation in this cell type are the production of cytokines such as IL-8, and GM-CSF. In addition, cell adhesion molecules such as VCAM-1, ELAM-1 and ICAM-1 are upregulated, which play distinct roles in the attachment and extravasation of peripheral blood leukocytes at sites from injury or inflammation. The following experiment was conducted to look for IL-8 production in cultured HUVEC exposed to S1P, LPA or other lysolipids.

Plating, Pretreatment and Treatment of HUVEC

Figure 4B:
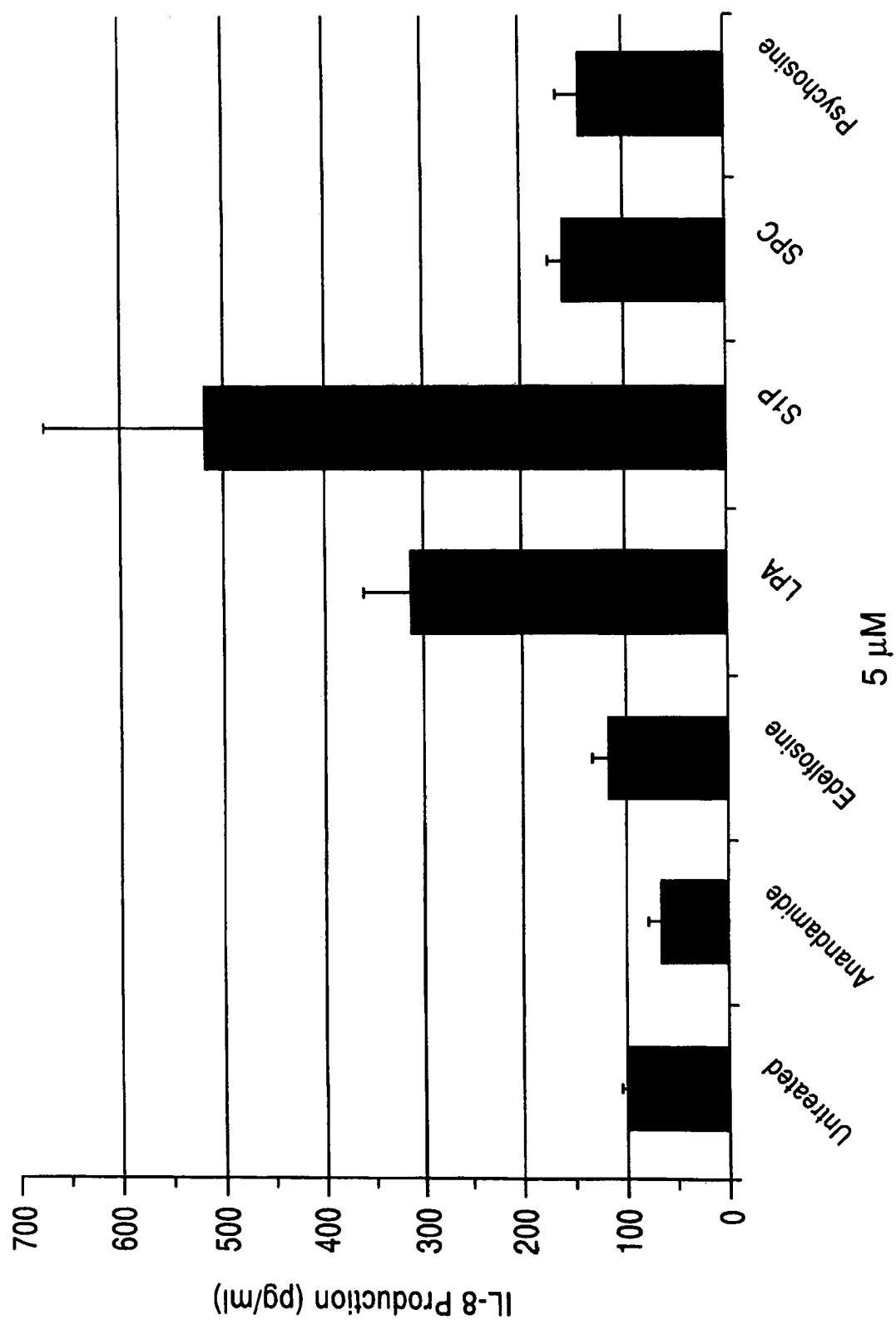
FIG. 4B illustrates the IL-8 response to lysolipids in primary cultured Human Umbilical Vein Endothelial Cells (HUVEC).

Procedures were Followed as Detailed Above in "Procedure 190 1 for HeLa Cells" with the Following Exceptions:

Cells: HUVEC (Clonetics, Cat. CC-2519) were passaged according to supplier's instructions and used at passage 3. Cells were plated at 20,000 cells/well into 24-well plates. The next day, cells were serum-starved overnight in EBM medium (Clonetics) with 0.5% FBS, and then treated in EBM without FBS for 6 hr with the following lysolipids:

1) Control (no lysolipids)
2) Anadamide
3) Edelfosine
4) LPA
5) S1P
6) SPC
7) Psychosine Supernatants were collected and IL-8 levels were determined using ELISA as described previously, Results: After 6 hr of treatment with 5 μM S1P, IL-8 levels were increased approximately 5-fold over untreated controls, as shown in FIG. 4B. LPA induced a 3-fold IL-8 increase at this concentration. Marginal increases were seen after SPC and psychosine treatment, while no responses was seen with anandamide or edefosine. Therefore, IL-8 production was responsive to S1P in primary cultured human endothelial cells, similar to results seen in HeLa cells. In addition, LPA induced IL-8 production in HUVEC, but not HeLa cells, suggesting that inflammatory receptors for LPA may be expressed in the former cell type. As shown below in FIG. 23, three cloned edge receptors respond to LPA as an agonist, and all three appear to transduce NF-κB activation in an agonist-dependent manner.

EXAMPLE 5

Lack of IL-8 Response to S1P in HL-60 Cells

HL-60 cells have been reported not to possess S1P receptors. One contradictory report has been published, but in that work, 10 μM concentration of S1P was used, 10–1000 times higher than other studies of S1P receptors. Nonetheless, HL-60 cells were examined for IL-8 response to S1P. As a control, IL-8 release from HL-60 cells was tested after treatment with TNF-α, which acts through a non-GPCR cell-surface receptor.

Procedure for HL-60 Cells:

A. Seeding Cells and Cell Plating Density
Cells: HL-60 (promyelocytic, human) suspension cells
Media: RPMI 1640 medium with 2 mM L-glutamine adjusted to contain 4.5 g/L glucose, 10 mM HEPES, and 1.0 mM sodium pyruvate+10% FBS
1) Cells were plated at a density of $0.2\times10^6$ cells/ml.
2) Density of cells after 48–56 hrs was approximately $1\times10^6$ cells/ml.

B. Overnight Pre-Treatments
1) Cells were spun down at 1000 rpm for 5 minutes.
2) Cell pellets were resuspended in 0.5% FBS media at a density of approximately $1\times10^6$ cells/ml.

C. Treatments and Collection
1) Made up all required solutions in 0.5% FBS media (control).
TNF-α 10 ng/ml
LPA 10 and 1 μM
S1P 10 and 1 μM
2) 1.4 ml appropriate treatments were added to each well of a 6-well plate.
3) Cells were spun down at 1000 rpm for 5 minutes.
4) Cells were resuspended in 0.5% media to give a density of approximately $1\times10^6$ cell/100 μl.
5) 100 μl cell suspension was added to each well.
6) All plates wee placed at 37° C./5% $CO_2$ for either 1, 6, or 24 hours.
7) After the specified time cell supernatants were collected into 1.5 ml eppendorf tubes, spun down at 14000 rpm for 5 minutes and stored at −20° C.:

D. Refer to Procedure #1 For HeLa Cells (D).

Results: Although H60 cells were capable of responding at 6 or 24 hr to TNF-α by releasing IL-8, no such release occured in response to S1P or LPA at concentrations up to 3 μM (see FIG. 5). This concentration is 100 times higher than the lowest concentration that reliably induces IL8 production in HeLa cells, Thus, the IL-8 response to S1P is expressed in some, but not all cell types.

EXAMPLE 6

HeLa Cell IL-8 Response to S1P Idiot due to Cytotoxicity

For LL, demonstration of signaling at concentrations well below those that cause cytotoxicity is important. For this purpose, an experiment was conducted to measure cytotoxicity in parallel with IL-8 response. A stringent measure of cytotoxicity was applied, in that IL-8 responses were measured after 6 hr of S1P treatment, whereupon the medium was replaced with normal medium and viable cells were counted at 24 hr. Therefore, IL-8 production had to be robust to be observed at 6 hr, while even slight of delayed toxicity would be seen as a loss of viability at 24 hr.

Procedure #5 For HeLa Cells:

Follow Procedure 190 2 For HeLa Cells With the Following Exceptions:
1) No PTX Pre-Treatment is required in section B.
2) Solutions required in section C are as follows:
S1P 0.3, 1, 3, 10, and 30 µM.
3) Cytotoxicity determination was added to section C; after step 5, 0.5 ml of 5% PBS/media was added to all the wells and placed at 37° C./5% $CO_2$ overnight.
4) Number of viable cells were counted after 24 hours of the initial treatments.

Figures 6A, 6B:
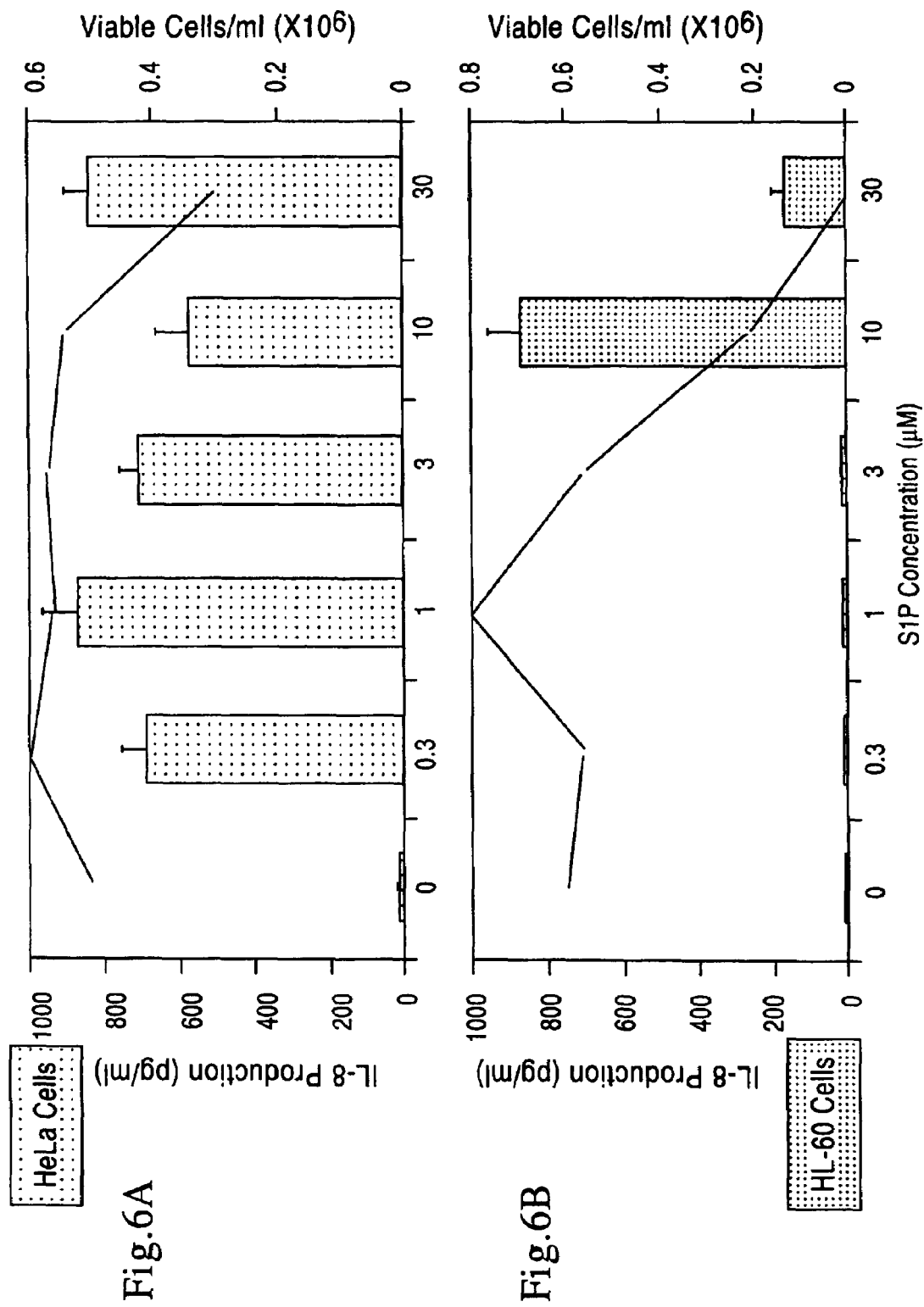
FIG. 6 illustrates the concentration-dependent IL-8 response to S1P in HeLa and HL-60 cells, as well as the cell viability at each S1P concentration level.

Results: No loss of HeLa viability was seen 24 hr after treatment with S1P concentrations up to 10 µM. In contrast, IL-8 production was seen even at 0.3 µM S1P, where levels were already near plateau values (see FIG. 6). In repeated experiments, the lowest S1P concentration that reliably induces IL-8 is about 30 nM, more than 100-fold below the cytotoxic threshold. HL-60 cells, on the other hand, show toxicity beginning at 10 µM S1P, but fail to produce IL-8 below the cytotoxic threshold. Thus, the IL-8 response to S1P does not reflect a non-specific cellular response to injury or impending death.

EXAMPLE 7

Effect of Suramin on IL-8 Response to S1P in HeLa Cells

Suramin is a non-selective inhibitor of extracellular site of action both for LPA and S1P. The IL-8 response was tested to determine if it could be blocked at this extracellular site.

Procedure #6 For HeLa Cells:

Follow Procedure 190 2 For HeLa Cells with the following Exceptions:
1) No PTX Pre-Treatment is required in section B.
2) Solutions required in section C are as follows:

| 3) Suramin 1 mg/ml | Stock 100 mg/ml in distilled water Dilute 1:100 | Calbiochem, Cat. 574625 |
|---|---|---|
| S1P 1 µM | | |
| S1P 1 µM + suramin 1 mg/ml | | |

4) A 30 minute pre-treatment at 37° C./5% $CO_2$ of 0.5 ml of 1 mg/ml suramin was done to all wells except control and S1P 1 µM before step 3 of section C.

Figure 7:
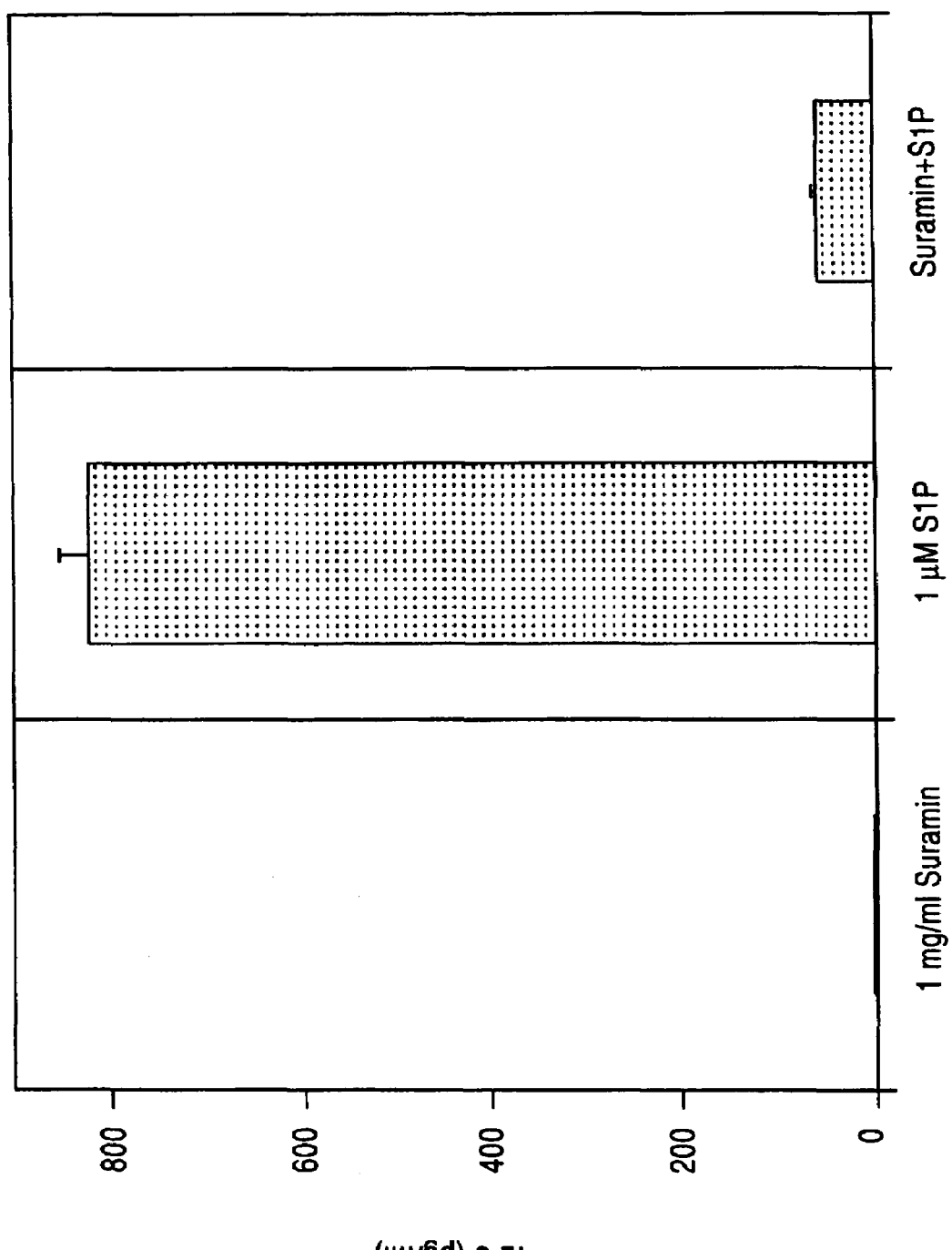
FIG. 7 illustrates the effect of suramin on the IL-8 response to S1P in HeLa cells.

Results: Suramin was extremely effective in blunting the IL-8 response to S1P (see FIG. 7). Therefore, the most likely site of S1P action is at an extracellular receptor.

EXAMPLE 8

Effect of NDGA and NAC on IL-8 Response to S1P in HeLa Cells

NF-κB and IL-8 production can be induced by many different inflammatory agents. Nearly all these diverse agents initiate signal transduction pathways that ultimately converge on destruction of the intracellular repressor IκB, which holds NF-κB function in check in resting cells. However, the upstream pathways used to target IκB differ depending on the nature of the inducer. While inflammatory cytokines and TPA use intracellular reactive oxygen species (ROS) as a second messenger, TNF-α and IL-1 usually do not. The ROS pathway and subsequent NF-κB activation can be inhibited by NDGA, NAC and certain other antioxidants. Therefore, the sensivity of the IL-8 response induced by S1P to these antioxidants was evaluated.

Procedure #7 For HeLa Cells:

Follow Procedure #2 For HeLa Cells with the Following Exceptions:
1) No PTX Pre-Treatment is required in section B.
2) Solutions required in section C are as follows:

| 3) NDGA 40 µM | Stock 10 mM in ethanol Dilute 1:250 | Sigma, Cat. N-5023 |
|---|---|---|
| NAC 30 mM | Stock 0.3 M in PBS, pH to 7.4 Dilute 1:10 | Calbiochem, Cat. 106425 |
| S1P 1 µM | | |
| S1P 1 µM + NDGA 40 µM | | |
| S1P 1 µM + NDGA 10 µM | | |
| S1P 1 µM + NAC 30 mM | | |

4) A 30 minute pre-treatment at 37° C./5% $CO_2$ of 0.5 ml of either NDGA or NAC was done to all wells except control and S1P 1 µM before step 3 of section C.

Figure 8:
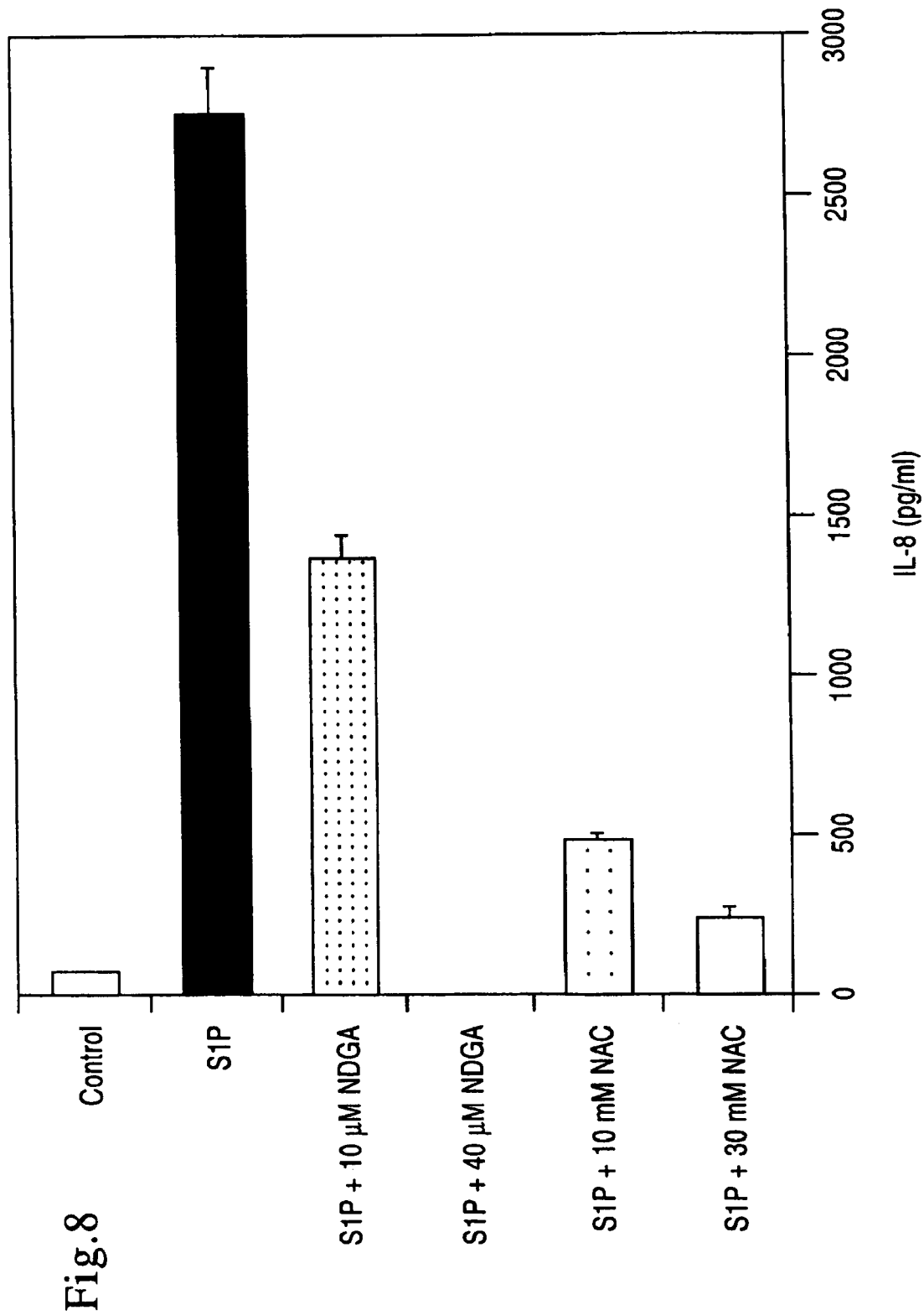
FIG. 8 illustrates the effect the antioxidants NDGA and NAC on the IL-8 tesponse to S1P in HeLa cells.

Results: The IL-8 response to S1P was significantly inhibited by both antioxidants (see FIG. 8). As noted in the literature the lipophilic antioxidant NDGA, was more potent that the hydrophilic NAC. However, some toxicity of NDGA was seen at 40 µM, a concentration that completely inhibited the IL-8 response to S1P. Nevertheless, these structurally unrelated antiosxidants both inhibited the IL-8 response to S1P, suggesting a cytokine-like pathway mediates S1P signal transduction.

EXAMPLE 9

Suramin and PTX-Sensitive IL-8 Response to Edelfosine, an Alkyl Ether Lysophospholipid, in HeLa Cells Edelfosine is an alkyl ether lysophospholipid with potent and selective antitumor activity. In spite of numerous studies highlighting changes in gene expression and signal transduction provoked by eldelfosine, conflicting data have been reported on its mechanism of action. Edelfosine inhibits protein kinase C, and thus may have intracellular sites of action. Edelfosine also can inhibit NF-κB in at least some cell types. Most important, edelfosine spares normal bone marrow cells at concentrations which kill tumor cells. The mechanism by which this discrimination is effected is unclear. However, given the structural similarity to LPA, the possibility that edelfosine might act on an edge family or LL receptor was considered. Therefore an IL-8 response to edelfosine in HeLa cells in the presence or absence of PTX or suramine was tested.

Procedure #8 For HeLa Cells:

Follow Procedure #2 For HeLa Cells with the Following Exceptions:

1) Solutions required in section C are as follows:

Suramin 1 mg/ml

| | | |
|---|---|---|
| ET-18-OCH$_3$ 10 µM | Stock 10 mM in ethanol Dilute 1:1000 | Calbiochem, Cat. 341207 |
| ET-18-OCH$_3$ 1 µM | Dilute 1:10 | |
| ET-18-OCH$_3$ 3 µM | | |
| ET-18-OCH$_3$ 3 µM + suramin 1 mg/ml | | |

2) A 30 minute pre-treatment at 37° C./5% $CO_2$ of 0.5 ml of suramin was done to all well except control, any PTX and ET-18-OCH$_3$ wells before step 3 of section C.

Figure 9:
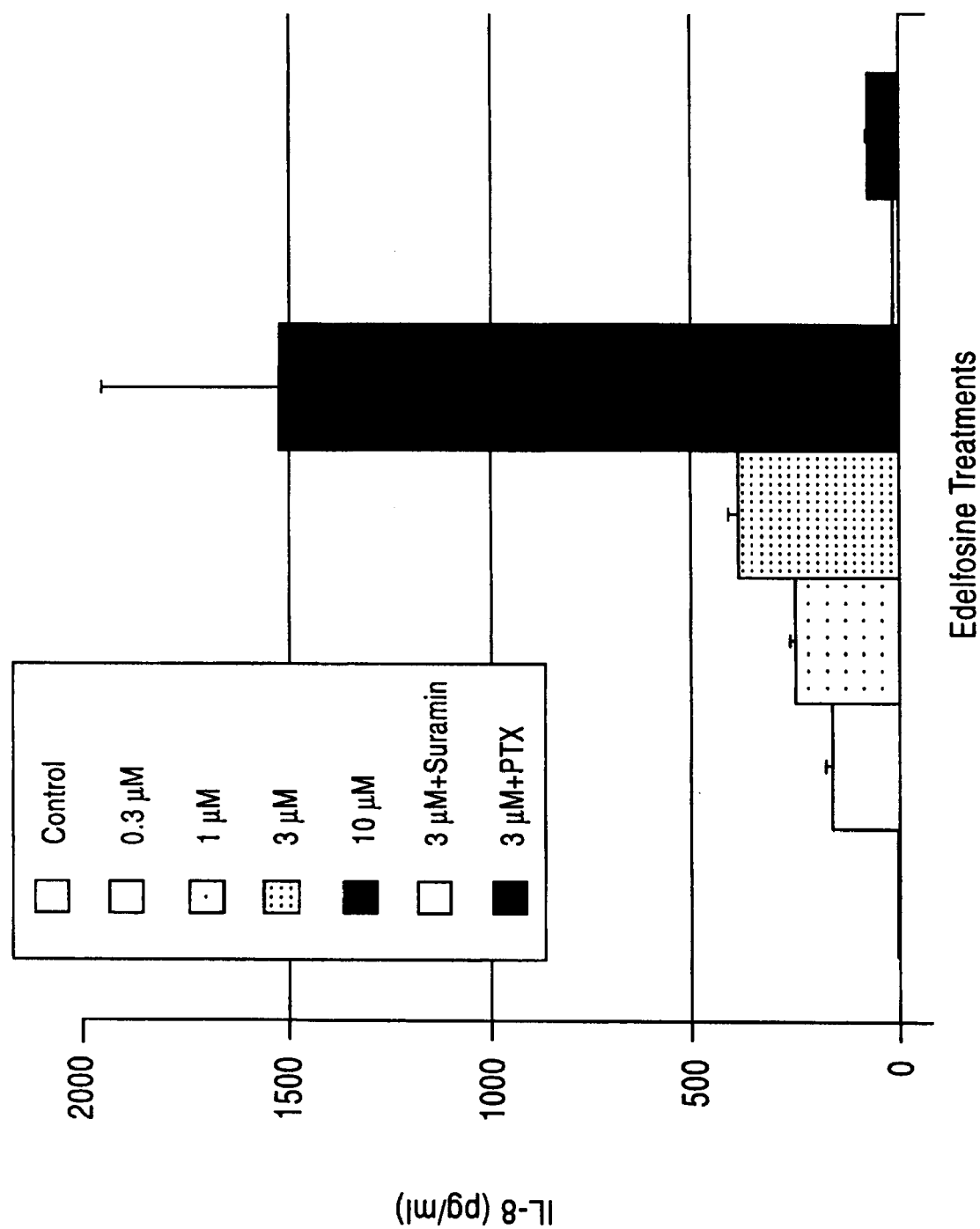
FIG. 9 illustrates the IL-8 response to edelfosine HeLa cells and the PTX- and suramin sensitivity of this response.

Results: Edelfosine, like S1P, induced an IL-8 response in HeLa cells at non-cytotoxic concentrations (see FIG. 9). Moreover, this response was potently inhibited by PTX and suramin, suggesting that a $G_{i/o}$-coupled cell-surface receptor may mediate the induction of IL-8 edelfosine. This receptor may be and edge or LL GPCR, although interaction with a previously identified PAF receptor cannot yet be ruled out. This finding contradicted edelfosine's inhibition of NF-κB previously reported in a different cell type. The present invention offers the means to identify and characterize the HeLa cell receptor for edelfosine. Expression of this receptor can then be compared in cells which differ in this cytotoxcity and NF-κB responses to edelfosine.

EXAMPLE 10A

Heterologous Expression of EDG-4/H218 in COS-1 Cells Reconstitutes the IL-8 Response to S1P We used a cAMP inhibition assay to show the presence of functional S1P receptors in Swiss 3T3, mouse neuronal B-103 and hamster CHO Pro5 cells. By comparing the cAMP responses of these cells to the expression profile of the 7 identified edg receptors, we speculated that both EDG-3 and EDG-4 are likely to be S1P receptors. However, although COS and HEK-293 cells both express abundant RNA for EDG-3, neither cell line shows an IL-8 response to S1P. This suggested that EDG-4 might selectively mediate the IL-8 response to S1P. Unfortunately, EDG-4 previously could not be measured in HeLa, COS-1 or other primate cells, since it has not yet been cloned from these species. The present invention remedies this situation by providing the sequence of the cloned HEDG-4. However, by transient transfection with a eukaryotic expression vector expressing full-length rat edg-4 cDNA it could be determined if this edg receptor can reconstitute the IL-8 response to S1P in COS-1 cells. The experiment included NF-κB reporter DNA to test for induction of the CAT reporter gene in parallel with the IL 8 response.

A. DEAE/Dextran Cell Suspension Transient Transfection.

Transfection was don as described in Anal Biochem 218:460 (1994).

a) Solutions:
RSC: 49 ml RPMI 1640 (Gibco; Cat. 21870-076)+1 ml Fetal calf serum +50 µl of 100 mM choloroquine (Sigma; Cat. C6628)
DEA/RSC: 18.4 ml RSC+1.6 ml of 10 mg/ml DEAE/Dextran (Promega; Cat. E112A).

b) Transfection Procedure:
1) 6 ml RSC was added to 4–50 ml tubes. The following amounts of DNA were addeded:

| | DNA (µg)/tube | | | |
|---|---|---|---|---|
| Tube | 1 | 2 | 3 | 4 |
| pcDNA3 | 5 | 5 | — | — |
| pC3-redg4 (rat edg-4) | — | — | 5 | 5 |
| 6xNFκB-tk-CAT5 | 5 | 2 | 5 | 2 |
| pBluescript | — | 3 | — | 3 |

The tubes were incubated at 37° C. until DEAE/RSC solution was made.
2) 6 ml of DEAE/RSC solution was added to each tube and incubated at 37° C. for 2 min.
3) 1.5 ml COS-1 cell suspension (5.5×10$^6$ cells total ) in RSC was added to each tube and incubated for 105 min in 37° C. incubator. Tubes were mixed every 20 min.
4) Following incubnation, tubes were spun for 5 min, cell pellets were washed with DMEM/F12+10% FBS once and then resuspended in 10 ml media. Cells were plated in 24-well plates at 0.2×10$^6$ cells/well.

B. Treatment

After 2 days (~40 hrs), cells were serum-starved (0.5% FBS media) with or without PTX (50 ng/ml) for at least 6 hrs and treated overnight with 0.5% FBS media, S1P (5 µm) in 0.5% FBS media or TPA (100 ng/ml) in 0.5% FBS media. 500 µl treatment volume was used. Supernatants were microfuged at 14,000 rpm for 10 min, transferred to new eppendorf tubes and stored at −20 C. for future IL-8 ELISA determination.

C. IL-8 ELISA (Enzyme-Linked ImmunoSorbent Assay).

The procedure as outlined in Procedure for HeLa Cells (D) was followed using 50 µl of sample per ELISA determination in duplicate.

Figure 10A:
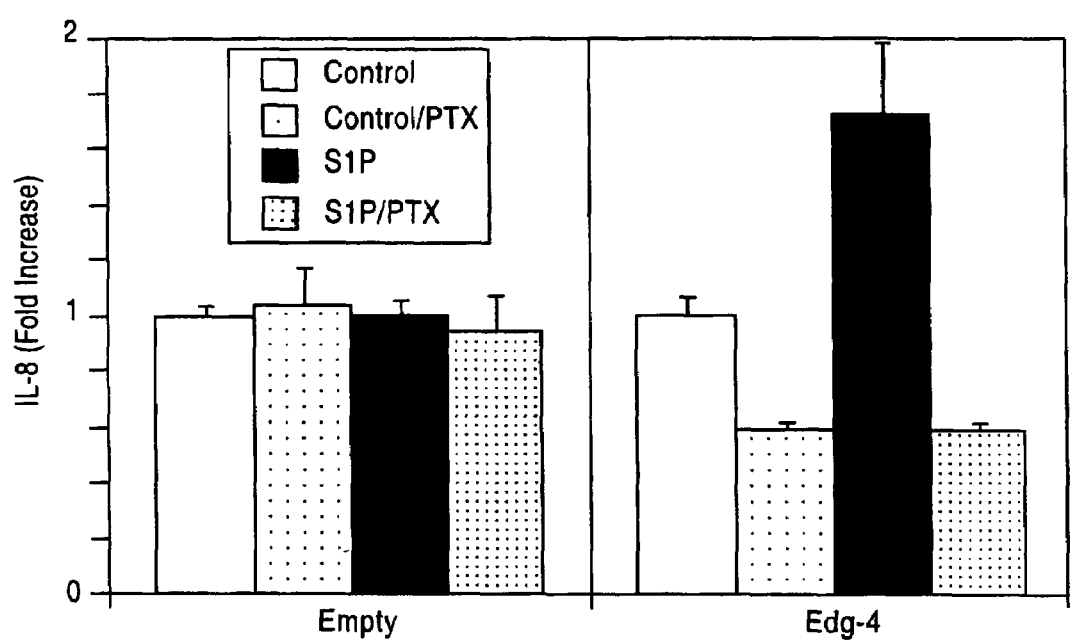
FIG. 10A illustrates the IL-8 response to S1P in 293-EBNA cells transfected with rat EDG-4 expression plasmid and the PTX sensitivity of this response.

Results: COS-1 cell transfected with the EDG-4 expression plasmid showed a 2-fold increase in IL-8 release when treated with 5 µm S1P as compared to untreated cells (see FIG. 10A.). No IL-8 to S1P was seen in control cells transfected with the empty expression vector pcDNA3. Moreover, the IL-8 response to S1P in EDG-4 transfected cells was pertussis toxin sensitive, since control and EDG-4 transfected cells showed similarly low levels of IL-8 in the presence of PTX. As expected, PTX did not inhibit the IL-8 response to TPA, which is not mediated by a GPCR. Despite the presence of abundantly expressed endogenous EDG-3 RNA, COS-1 cells do not show an IL-8 response to S1P. However, heterologous expression of rat EDG-4 reconstitutes a PTX-sensitive IL-8 response to S1P, similar to the endogenous receptor expressed in HeLa cells. Therefore, the functional assay described herein critically depends on the expression of specific edg and/or LL receptors which are expressed endogenously in HeLa cells, and which can be heterologously expressed in the form of EDG-4, and perhaps other related GPCRs.

EXAMPLE 10B

Expression of Endogenous Edg Receptors in 293-EBNA Cells

Figure 10B:
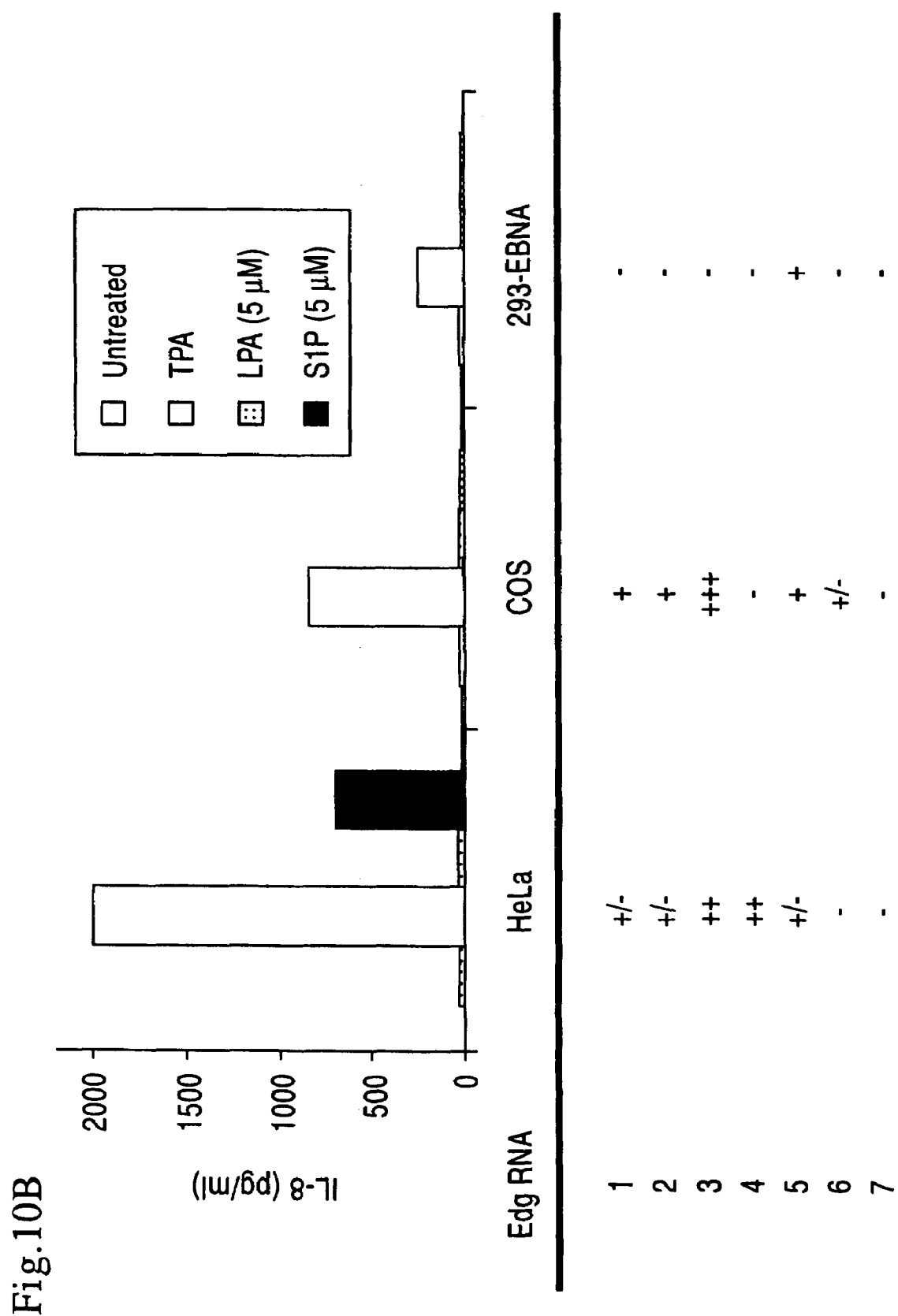
FIG. 10B illustrates the expression of endogenous edg receptors in HeLa, COS and 293-EBNA cells.

To determine the more appropriate cells for transfection with the edg cDNA receptors, a Northern Blot experiment was conducted for HeLa, COS and 293-EBNA cells. As can be seen from FIG. 10B, the Northern blot shows that 293EBNA cells has no visible expression of any of the edg receptors other than possible EDG-5. In conjunction with the Northern Blot experiment, each of these cells, HeLa, COS and 293-EBNA were exposed to TPA, LPA, and S cells showed no IL-8 production for LPA and S1P and the measured for IL-8 production. The 293-EBNA cells showed no IL-8 production for LPA and S1P indicating that there is no expression any EDG receptor.

EXAMPLE 11

Heterologous Expression Studies Using Lucifease Assay

To improve on the 2-fold CAT reporter gene induction observed in the previous experiment, 2 changes were made. First, the NF-κB response element was reconstructed in a new reporter construct (p4Luc) suitable for stable maintenance as an episome in primate cells. Second, transient transfection was carried out in 293-EBNA cells (Invitrogen; Cat. R620-07), and EBNA-1 expressing derivative of HED-293. The p4-Luc reporter used the backbone of pREP4 (Invitrogen; Cat. V004-50), which contains the EBV orgin of replicaiton ($EBV_{ori}$), as well as the EBNA-1 viral antigen required to maintain $EBV_{ori}$ containing plasmids as stable episoms in primate cells, and a prokayotic selection marker. A dominant eukaryotic selection marker for zeocin resistance was substituted for expression in pREP4. The promoter of pREP4 was then excised and replaced with a multi-cloning site for introduction of promoter/enhancer inserts. The NF-κB inser of the previous CAT reporter was subcloned into this site and all cloning junctions were sequenced to verify the structure of the plasmid, called NF-κB-tk-p4Luc.

Assay #1

Monolayer Transient Transfection Protocol for 293-EBNA

Day 1:
1) 150 mm plates of 293-EBNA obtained from Invitrogen (Cat. R620-07) with a confluency of 18 80% were used for transfection.
2) 6.6 μg NF-κB-tk-p4Luc reporter DNA and 6.6 μg of pC3-redg4 (expressing rat EDG-4), or pcDNA3 DNA was diluted in 500 μl OPTI-MEM (Gibco; Cat. 31985-062)
3) 96.8 μl Lipofectamine (Gibco; Cat. 18324-020) was diluted in 500 μl of OPTI-MEM.
4) The 2 solutions were mixed gently and the tube was incubated for 30 min at room temperature.
5) The 293-EBNA plates were washed once with PBS and 13 ml OPTI-MEM was added to each plate,
6) 6 ml OPTI-UMM was added to each transfection tube and this was added to a plate of 293EBNA cells. The plates were left for 4 hrs at 37° C. in a 5% $CO_2$ incubator.
7) After 4 his, the media was removed and replaced with frest 10% FBS media.

Day 2:
1) Transfected cells were washed, typsinized with 1× tryspin, resuspended in 10 ml media and counted.
2) $0.02 \times 10^6$ cells were plated per well of a 96-well Blackview plate coated with polyD-lysine. No cells were plated in the outside wells of the 96-well plate. Two 96-well plates were seeded for each transfection.

Day 3:
1) Cells were washed with PBS and 140 μl serum-free media (SFM) added to each well. Plates were incubated in 37° C. incubator for 6 hrs.
2) After 6 hrs, media was removed and cells treated with compounds diluted in 0.5% FBS media (140 μl added to each well).

The Following Treatments Were Used:

pcDNA3:
Untreated, LPA 10 μM, LPA 5 μM, S1P 10 μM, S1P 2 μM, SPC 3 μM, SPC 1 μM, edelfosine 1 μM, edelfosine 500 nM, LPC 1 μM, LPC 500 μM, 20% FBS (Gibco; Cat. 10437-028), TPA (50 ng/ml), TPA (25 ng/ml).

pC3-EDG4:
Untreated, LPA 10 μM, LPA 5 μM, S1P 10 μM, S1P, 2 1μM, SPC 3 μM, S1P 1 μM, edelfosine 1 μM, edelfosine 500 nM, LPC 1 μM, LPC 500 nM, 20% FBS, TPA (50 ng ng/ml).
3) Cells were treated for 24 hrs.

Day 4

Luciferase Assay
1) Luclite kit (Packard; Cat. 6016911) was used for luciferase assay. All reagents were brought to room temperature before use.
2) Supernatant was transferred to a new 96-well plate and stored at −20 C. for rupture IL-8 measurement.
3) 50 μl 0.5 M HEPES pH 7.8 buffer (1 mM $MgCl_2$ 1 mM $CaCl_2$) was addeded to all wells of 96-well plate. Black adhesive backing (polyfitronics) was aligned to the bottom of the viewplate.
4) Luclite substrate was made up by adding 10 ml substate diluent to 1 vial lyophilized substrate. Reconstituted substrate was kept under a dark container. 50 μl substrate was added to each well.
5) A clear adhesive plate sealer was adjusted on to the viewplate and sealer rubbed over the plate with a Kimwipe. The plate was shaken on a plate shaker at 500 rpm for 5 seconds right side up and then upside down. A stop plate was placed on top of the blackview plate to keep it in the dark.
6) Plates were incubated at room temperature for 30 min.
7) After incubation, plates were counted in a 12 detector Packard Top Count on a program without dark delay.

Figure 11B:
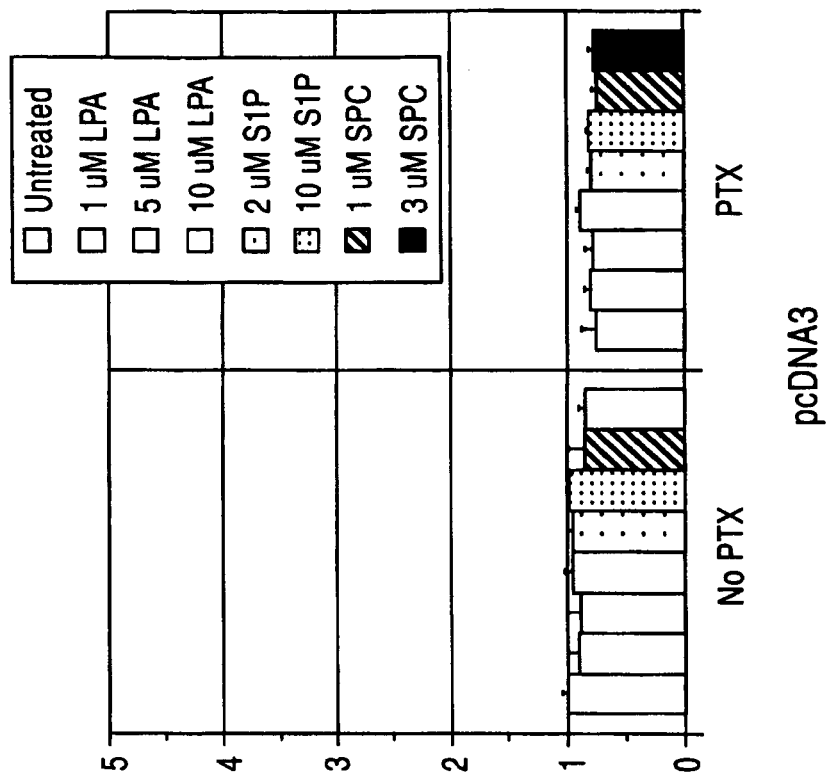
FIG. 11 illustrates the NF-κB reporter response to S1P, LPA and SPC in 293-EBNA cells cotransfected with and edg4 expression plasmid and a NF-κB-tk-p4Luciferase reporter plasmid.
Figure 11A:
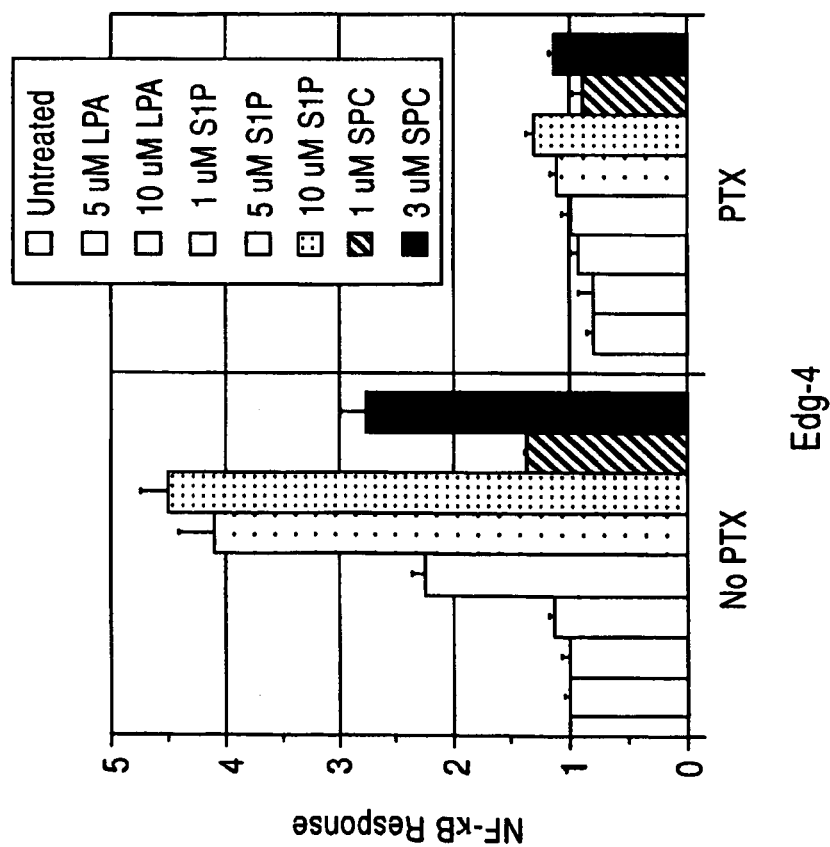

Results: 293-EBNA cells cotransfected with pC3-redg4 and the NF-κB-tk-p4Luc reporter showed a 4–4.5-fold increase in luciferase activity when the cells were treated with 5 μM or 10 μM S1P (see FIG. 11). EDG 4 expressing cells treated with 1 μM S1P showed a 2-fold increase in lucifrease activity. Pretreatment with PTX inhibited the response to S1P at all concentrations. No increase in luciferase activity was seen in cells cotransfected with the (empty expression vector pcDNA3 and the liciferase reporter, and no change in luciferase activity was seen with PTX pretreatment in these cells. SPC also induced the reporter gene in EDG-4 expressing cells, but not cells, and this response was also PTX-sensitive. The potency of SPC was apparently low than at of S1P, though tis was not rigorously assessed, TPA strongly induced the NFκB reporter, and PTX did not affect this induction, as expected.

No induction of the reporter was seen with any of the other ligands assayed, either in pC3-redg4 or pcDNA3-transfected cells.

These results strongly support the assignment EDG-4 as a PTX sensitive S1P receptor which signals via NF-κB and inflammatory gene expression. Furthermore, the results provide a definitive validation of the receptor-dependent functional assays, which comprise one aspect of the present invention.

The isolated receptor, which is endogenously expressed in HeLa cells, also constitutes one embodiment of the current invention. Numerous methods well-known to those skilled in molecular biology and expression cloning are available to isolate the edg or LL GPCR which fulfills the criteria we have established herein. These include the screening of a HeLa cDNA library (Invitrogen; Cat. A550-26) with degenerate or specific oligonucleotides derived from EDG-4, the EDG-1/EDG-3/EDG4 subfamily, to or the broader edg family including EDG-1 and EDG-2 1 paralogs, as well as screening by hybridization with rat EDG4 coding region DNA. Expression cloning should also easily identify an edg/LL receptor cDNA, cloned in a suitable expression vector, which confers on 293-EBNA cells the capacity to produce IL8 or induce a NF-κB reporter it response to S1P, SPC and/or LPA in a PTX-sensitive manner.

Assay#2

The IL-8/NF-κB response met all the criteria of a receptor-dependent, robust and reproducible functional assay of EDG/LL receptors. This assay was applied to various cloned EDG receptors for responsiveness to natural LL, a well as complex mixtures such as fetal bovine serum. In this way, agonist ligands for the orphan EDG receptors are identified, and EDG receptors which are capable of inflammatory responses are identified.

Transient Transfection protocol for 293-EBNA

Day 1:

The above protocol for assay 1 was followed except for the following changes:
1) 100 mm plates of 293-EBNA with a confluency of ~80% were used for transfection.
2) 3 µg NFκB-tk-p4Luc reporter DNA and 3 µg pC3-hedg1, pC3-hedg 3, pC3-redg4, pC3-hedg5 or pcDNA3 DNA was diluted in 240 µl OPTI-MEM (Gibco; Cat. 31985-062)
3) 22 µl lipofectamine (Gibco; Cat. 1 8324-020) was diluted in 240 µl OPTI-MEM.
    4) The 293-EBNA plates were washed once with PBS and 7 ml OPTI-MEM was added to each plate.
5) DNA/lipofectamine mixture was added to each plate of 293-EBNA cells. The plates were left for 4 hrs at 37° C. in a 5% $CO_2$ incubator.

Day 2:

1) $0.01 \times 10^6$ cells were plated per well of 96-well Blackview plate coated with polyD-lysine. No cells were plated in the outside wells of the 96-well plate.

Day 3:

The following treatments were used for all transections:
    Untreated, S1P 3 µM, LPA 3 µM, psychosine 3 µM (Sigma; Cat. P-9256, Stock 10 mM in methanol), SPC 3 µM, LPC 1 µM, sphingosinue 3 µM, 20% FBS , TPA (20 ng/ml), edelfosine 1 µM, lysosulfatide 3 µM.

Figure 12:
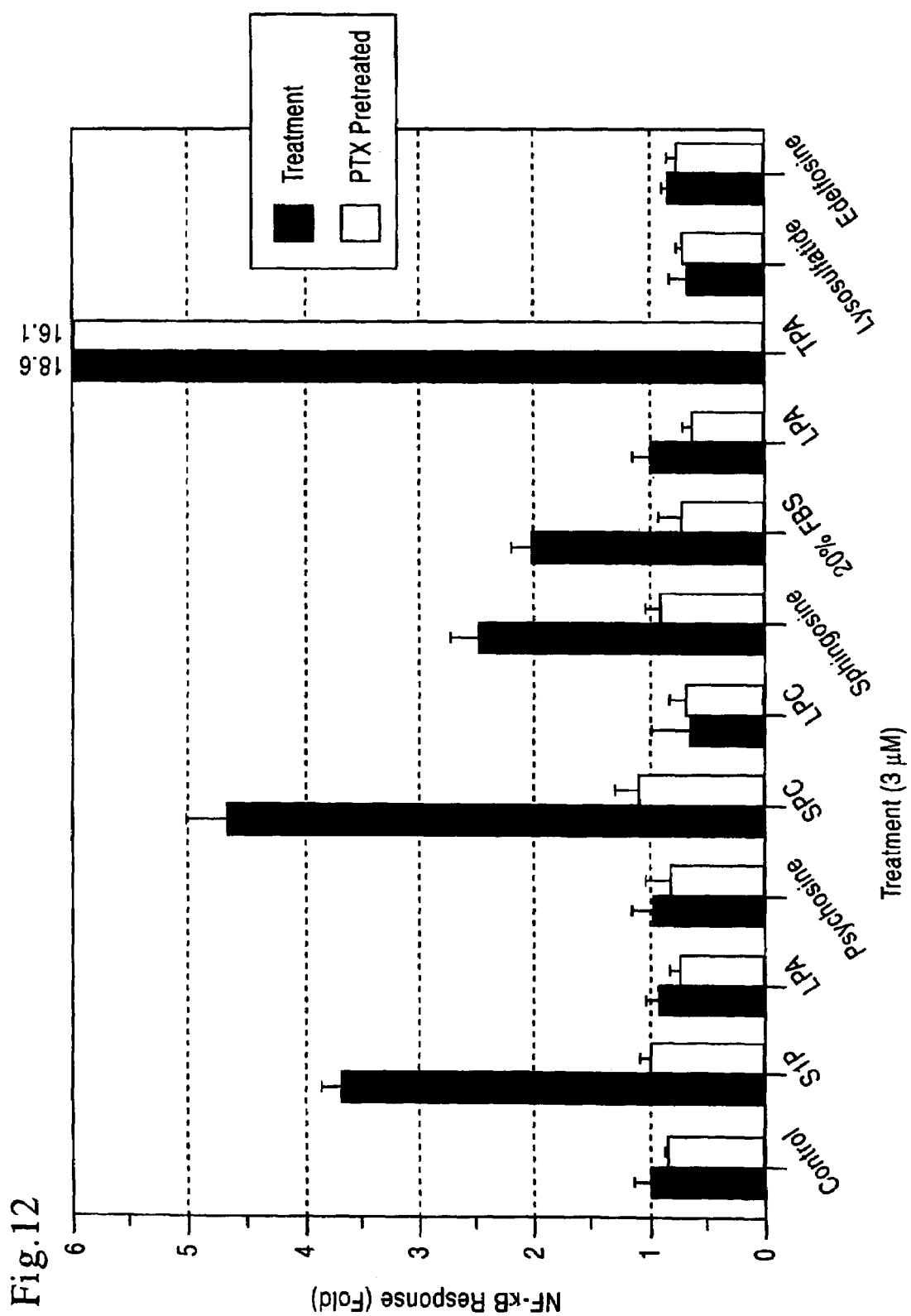
FIG. 12 illustrates the NF-κB reporter response to S1P, LPA, pyschosine, SPC, LPC, sphingosine, 20% FBS, TPA, lysosulfatide and edelfosine in 293-EBNA cells cotransfected with an EDG-4 expression plasmid and an NF-κB-tk-p4Luciferase reporter plasmid, as well as the PTX sensitivity of this response.

Results: 293-EBNA cells transfected with the pC3-redg4 construct showed a 3.5-fold increase in luciferase activity when the cells were treated with 3 µM S1P (see FIG. 12), in this experiment 3 µM SPC showed a 4fold increase in luciferase activity. As seen previously, PTX efficiently inhibited the response to S1P and SPC. No response to S1P or SPC was seen in pcDNA3-transfected 293-EBNA cells, confirming previous results. This demonstrates that the luciferase response to S-1P and SPC is critically dependent on the heterologous express ion of EDG-4 in the 293-EBN-4 cells.

Cells transfected with rat EDG-4 or human EDG-5 and treated with 20% FBS also showed ~2-fold increase in luciferase activity and PTX efficiently inhibited this response. No such response was seen to 20% FBS in pcDNA3-transfected cells, and PTX had no effect on the luciferase expression of the control cells in the presence or absence of 20% FBS. S1P is present in FBS as a result of release from clotted platelets, and can account for the increase in luciferase observed in EDGA expressing cells treated with 20% serum. We conclude that 20% serum contains 1 or more agonists for EDG-5, which may consist of LPA or related LL. Moreover, EDG-5 like) EDG-4, is capable of responding through proinflammatory NF-κB signaling pathways.

These results, in addition to confirming the previous experiment, support a broad application of this robust and reproducible functional assay in screening for agonists and antagonist of edg and LL receptors. With a positive receptor-induced readout such as IL-8 production or the NF-κB reporter gene, experiments can be carried out on transiently transfected cells, allowing for rapid and flexible screening of a target edg/LL receptor. This contrasts with an inhibition assay such as the $G_i$-mediated inhibition of cAMP production by forskolin. In the latter type of assay, stable cell lines are necessary so that the decrease will not be masked by the uninhibited response of untransfected cells.

Additionally, this approach can identify agonists for orphan edg/LL receptors, provided the receptors respond through the inflammatory pathways described herein. Even where the natural agonist of an edg receptor is unknown, screening for agonists is possible with these robust and reproducible readouts. Using this approach, agonists can be identified for heterologously (or endogenously) expressed edg/LL receptors whether applied as chemically pure substances, ligand clips, or in biological preparations such as serum. It is a tractable proposition to purify, isolate, characterize and synthesize the active LL from serum with this reliable bioassay in hand.

Assay#3

NF-κB activates gene expression by binding to specific DNA sequences found in the promoters of genes regulated by this inflammation-related transcription factor. A different sequence, the serum response element (SRE) is found in the promoters of genes which are upregulated by the addition of serum to serum-starved cells. Both LPA and S1P are found in micromolar concentrations in serum, and have been shown to mediate a significant part of the SRE upregulation caused by serum. Since SRE activation reflects different and distinct pathways from those leading to NF-κB activation, EDG-4 and the closely related EDG-1 and EDG-3 receptors were tested for induction of a SRE reporter gene by S1P or SPC, The SRE reporter was identical to the NF-κB reporter, except that the NF-κB binding sites were replaced with 2 SRE sites. The new report was called 2XSREtk-p4Luc-zeo.

Transient Transfection Protocol for 293-EBNA (Assay 31)

Day 1.

The protocol described in Example 11 for Assay 1 was allowed except for the following changes:

1) 100 mm plates of 293-EBNA ith a confluency of ~80% were used for transfection,
2) SRE Cotransfection: 0.5 µg of 2XSREtk-p4Luc-zeo reporter DNA and 3.5 µg pcDNA3, EDG-1, EDG-3 pC3-hE3P2, different from the clone used in Assay 2 of Example 11) or the newly cloned human EDG-4 (pC3-hedg4#36); NF-κB Cotransfection: 2 µg 6XNFκBtk-p4LUc-zeo reporter DNA and 2.0 µg pcDNA3, EDG-1, EDG-3 (pC3-hE3HP2), or EDG-4 (pC3-hedg4#36). Expression plasmid and reporter plasmid DNA samples were combined and diluted in 750 µl of DMEM/F12 (serum free media) and 20 µl Plus Reagent (Lipofectamine Plus Kit, Life Technologies Cat. 109640-13), and incubated at room temperature for 15 min.
3) 30 µl Lipofectamine Reagent (Lipofectamine Plus Kit) was diluted in 750 µl DMEM/F12. The diluted Lipofectamine was then combined with the DNA/Plus mixture and incubated at room temperature for 15 min.
4) The 293-EBNA plates were washed once with PBS and 5 ml DMEM/F12 was added to each plate.
5) DNA/Plus/Lipofectamine mixture was added to each plate of 293-EBNA cells. The plates were left for 3 hr at 37° C. in a 5% $CO_2$ incubator.
6) The transfection medium was replaced with serum-free DMEM/F12 for cells transfected with 2XSREtk-p4Luc-zeo reporter DNA and with DMEM/F12 plus 10% FBS for cells transfected with 6XNFκBtk-p4Luc-zeo reporter DNA.

Day 2.
2) Transfected cells were harvested by trypsinization and 50,000 cells per well were plated in 96-well Blackview plates coated with poly D-lysine Becton Dickinson Labware, Cat. 40640). No cells were plated in the outside wells of the 96-well plate.

Day 3.
1) Media for cells transfected with 6XNF-κBtk-p4Luc-zeo reporter DNA was replaced with DMEM/F12 plus 0.5% FBS.

Day 4.
1) Media was removed and cells treated with compounds diluted in DMEM/F12 media. The following treatments were used for all transfections:
Untreated: serum-free medium alone, S1P (3 µM), SPC (3 µM).
2) The cells were treated for 6 hours.
3) Luciferase assay was performed.

Figure 13B:
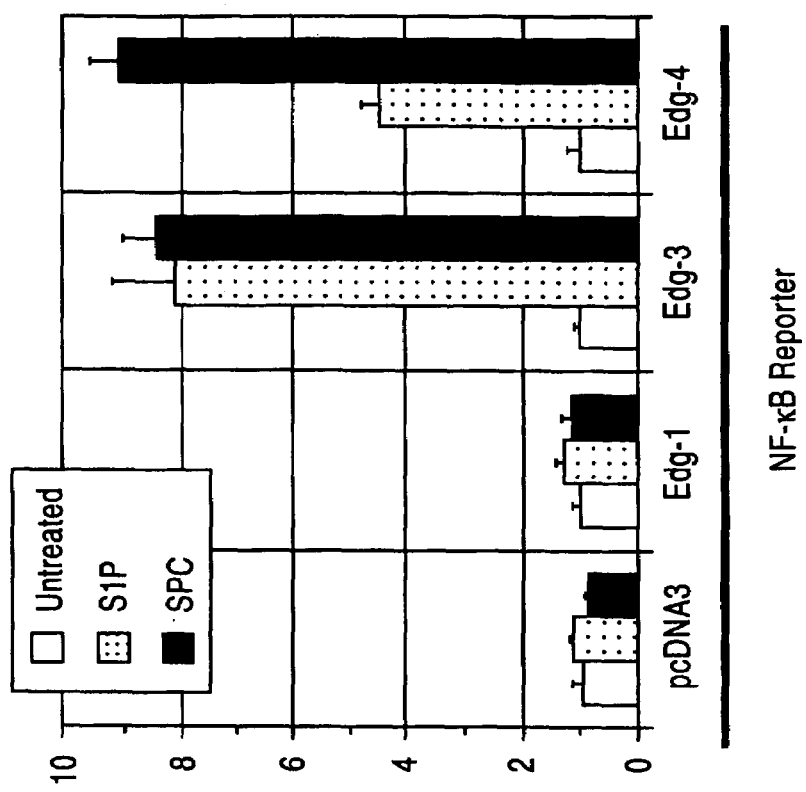
FIG. 13 illustrates the EDG-1, EDG-3 and EDG-4 receptor response to S1P or SPC using (A) the SRE reporter gene assay or (B) the NF-κB-tk-p4Lucifrase reporter assay.
Figure 13A:
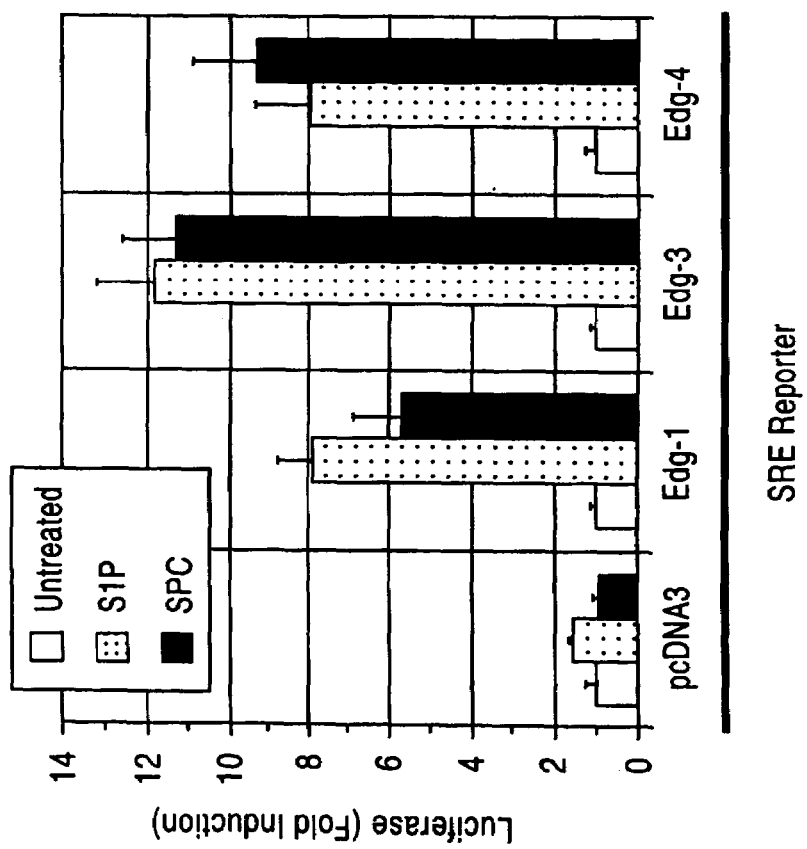

Cotransfection of EDG-1 and 2XSREtk-p4Luc-zeo reporter resulted in a 8-fold increase in luciferase activity after treatment with 3 µM S1P, and a 6-fold increase after treatment with 3 µM SPC (FIG. 13A). In contrast, no increase in luciferase activity was seen in S1P- or SPC-treated cells cotransfected with EDG-1 and the 6XNFκBtk-p4Luc-zeo reporter (FIG. 13B). Thus, although the EDG-1 receptor is fully functional, and recognizes S1P and SPC as agonists, the NP-κB reporter was not induced. This result confirms the finding that EDG-1 is a non-inflammatory subtype of S1P/SPC receptor.

Although the original human EDG-3 clone did not produce a NF-κB response to S1P or SPC, a different human EDG-3 clone, derived from human pancreas (pC3-E3HP2), was cotransfected with the SRE reporter and this clone showed a robust 12-fold response to 3 µM S1P and 11-fold response to 3 µM SPC (FIG. 13A). A control cotransfection of the empty expression vector pcDNA3 with the SRE reporter showed a small but reproducible response to S1P (about 1.5-fold) but not SPC (FIG. 13A). The robust SRE response of the pancreas EDG-3 clone confirms our hypothesis that both EDG-1 and EDG-3, in addition to the closely related EDG-4, function as S1P/SPC receptor subtypes. Moreover, a similar induction of the NF-κB reporter gene (about 8-fold) was seen both in S1P and in SPC-treated cell, compared to untreated controls, after cortransfection with EDG-3 (FIG. 13). No such induction was seen in the cells cotransfected with pcDNA3 and the NF-κB reporter gene (FIG. 13B), indicating that the NF-κB response to S1P and SPC in EDG-3 transfected cells was not due to endogenous receptors. Therefore, EDG-3 (but not EDG-1) must be considered to be another edg/lysolipid receptor subtype which can mount an inflammatory response to S1P and other lysosphingolipids, Like EDG-1 and EDG-3, human EDG-4 (See Examples 12, 13 and 14 for identification and cloning of HEDG 4) also responded through the SRE reporter gene, showing a 8-fold response to S1P and a 9-fold response to SPC, relative to untreated control cells (FIG. 13A). As we had previously observed with the rat EDG-4 expression construct tested in Example 11, human EDG-4 also mediated a robust NF-κB response, showing a 4.5- and 9-fold induction of the reporter gene to S1P and SPC, respectively (FIG. 13B). Therefore, induction of inflammatory gene expression pathways is a conserved feature of EDG-4 in humans and rats, and likely reflects a fundamental biological aspect of receptor function.

Together, these results suggest that the SRE response is a shared feature of many different edg/lysolipid receptors, and can be used to verify the response of intact functional receptors to their cognate agonist(s), on the other hand, the NF-κB response is shared by a subset of edg/lysolipid receptors which are specialized to mobilize inflammatory gene expression and immune system recruitment. Since EDG-1, EDG-3, EDG-4 and EDG7 are all S1P SPC receptors, their varying and even overlapping tissue distribution and inducibility frustrate the meaningful design, screening and therapeutic testing of anti-inflammatory S1P analogs unless the subtype specificity of inflammatory signaling is appreciated. This complexity highlights the value and utility of the recombinant inflammatory lysolipid receptors and the functional assays specified herein.

EXAMPLE 12

Identification of Human Expressed Sequence Tags (ESTs) Homologous to Rat H218 (EDG-4)

A BLAST search of the complete GenBank database was conducted with the sequence of an oligonucleotide RE4-181F[3'-GAGAAGGTTCAGGAACACTACAATTA-CACCAA GGA-3'](SEQ ID NO:1), based on the sequence of rat EDG-4. The search identified a human EST (GenBank accession AA804628), which was 88% identical to the corresponding region of rat EDG-4 cDNA (GenBank accession U10699). A subsequent TBLASTN search of the EST database using the predicted polypeptide product of the rat EDG-4 cDNA (according to accession number U10699) revealed 2 other matching EST's (accession AA827835 and AA834537) in addition to the original human EST. The 3 EST's encompassed the predicted translation start site of human EDG-4 (based on similarity to rat EDG-4), overlapped each other extensively, and together spanned some 109 codons of the N-terminal portion of the human EDG-4 polypeptide (FIG. 14). The predicted fragment of the human EDG-4 polypeptide showed 90.1% identity and 93.3% similarity to the equivalent fragment of rat EDG-4, suggesting the human polypeptide is an ortholog of the rat EDG-4 gene product, rather than a closely related gene product. A BLAST search was then conducted with the complete sequence of rat EDG-4 cDNA (accession number U10699) against the EST database. In addition to the previously identified EST's, 2 EST's apparently derived from the 3'-untranslated region of human EDG-4 cDNA adjacent to the poly(A) tail were found (AA767046 and N93714). Of the 5 human EST's identified in total, only N93714 was present in the public database before Feb. 19, 1998. This EST was derived from the 3' end of a 1421 by cDNA insert which contained no coding region. The closet match recorded in the DBEST database entry (accession 500502) was a cGMP phosphodiesterase. The 5' end of the clone had been sequenced and given the GenBank accession W21101; however, similarity to other cDNAs was obscured by the presence of an Alu sequence.

EXAMPLE 13

Survey of Potential cDNA Sources Using 5' End and 3' End Diagnostic PCR

To evaluate possible sources of human EDG-4 cDNA from HeLa cells (which express the inflammatory S1P/SPC receptor) and lung (a predominant site of EDG-4 expression in rat) for the presence of the desired cDNA fragments, diagnostic PCR primers were designed from the cluster of 5' end EST's (AA804628, AA834537 and AA827835) and 3' end EST's (N93714 and AA767046):

```
5' end primers:
                                              (SEQ. ID NO:2)
HE4-DF1 [5'-ATTATACCAAGGAGACGCTGGAAAC-3']

(SEQ. ID NO:3)
HE4-DR1 [5'-AGAGAGCAAGGTATTGGCTACGAAG-3']

3' end primers:
                                              (SEQ. ID NO:4)
HE4-DF2 [5'-TCCTCTCCTCGTCACATTTCCC-3']

(SEQ. ID NO:5)
HE4-DR2 [5'-GCATTCACAAGAAATTACTCTGAGGC-3']
```

Template sources: 1) cDNA library from WI-38 lung fibroblasts (Origene Technologies Inc., Cat. DLH-102); 2) cDNA library from human lung (Clontech, Cat. 7114-1); 3) cDNA library from HeLa cells Invitrogen, Cat. A550–26); 4) First strand cDNA prepared in-house from HeLa cell total RNA. Each template was amplified with each pair of primers using the Expand™ PCR system from Boehringer Mannheim (Cat. 1681-842).

Each reaction contained the following reagents:

| | |
|---|---|
| 2 µl | 10x PCR Buffer 3 |
| 0.4 µl | 25 mM dNTP mix |
| 0.6 µl | Primer HE4-DF1 or HE4-DF2 (10 µM) |
| 0.6 µl | Primer HE4-DR1 or HE4-DR2 (10 µM) |
| 0.3 µl | Expand ™ enzyme (3 units) |
| 15.1 µl | water |
| 1 µl | cDNA template |
| PCR conditions: | |
| Incubate: | 94° C. for 2 min |
| 30 cycles: | 94° C. for 40 sec |
| | 55° C. for 1 min |
| | 68° C. for 40 sec |
| Incubate: | 68° C. for 8 min |
| Hold: | 4° C. |

The expected ~200 bp 5' PCR product was successfully amplified from WI-38 lung cDNA (Origene), and from the first stand cDNA prepared in-house from HeLa cells. The ~200 bp 3' PCR product was successfully amplified from human lung libraries (Origene and Clontech) and HeLa cDNA library (Invitrogen), but not from the random hexamer-primed HeLa first strand cDNA. Thus, the WI-38 human lung fibroblast cDNA library (Origene) appeared to be the most likely source of full length human EDG-4 cDNA clones. More important, the successful amplification of a fragment of human EDG-4 cDNA from HeLa provides a concrete demonstration of EDG-4 expression in this S1P/SPC-responsive cell line, and directly supports the claim of composition of matter on EDG-4 and inflammatory S1P/SPC receptors isolated from HeLa cells. Together with full-length sequence information presented below, full-length cloning and expression of the inflammatory EDG-4 receptor from HeLa cells is reduced to a simple technical exercise for one skilled in the art.

EXAMPLE 14

Cloning of the Complete Coding Region of Human edg-4 cDNA

Two new primers were designed to amplify the complete coding region and most of the 3'-untranslated region. The primers were based on the EST sequences spanning the translation start site, and the EST sequences representing putative 3'-untranslated sequences of human edg-4. Provided that these primers bind appropriately to a common template (ie. human edg-4 cDNA), a ~2.4 kb PCR fragment should be amplified, containing the complete coding region. These primers were used in a PCR reaction with the WI-38 human lung fibroblast cDNA library (Origene) follows:

```
                                              (SEQ. ID NO:6)
HE4-DF3 [5'-GAGCCCCACCATGGGCAGCTTGTACT-3']

(SEQ. ID NO:7)
HE4-DR2 [5'-GCATTCACAAGAAATTACTCTGAGGC-3']
```

Each reaction contained the following reagents:

| | |
|---|---|
| 5 µl | 10x PCR Buffer 3 |
| 1.0 µl | 25 mM dNTP mix |
| 1.5 µl | Primer HE4-DF3 (10 µM) |
| 1.5 µl | Primer HE4-DR2 (10 µM) |
| 0.75 µl | Expand ™ enzyme (2 units) |
| 39.25 µl | water |
| 1 µl | cDNA template (250 ng or 500 ng of DNA) |
| PCR conditions: | |
| Incubate: | 94° C. for 2 min |
| 10 cycles: | 94° C. for 40 sec |
| | 60° C. for 40 sec |
| | 68° C. for 5 min |
| 25 cycles: | 94° C. for 40 sec |
| | 60° C. for 40 sec |
| | 68° C. for 3 min |
| Incubate: | 68° C. for 8 min |
| Hold: | 4° C. |

Amplified reactions from 250 ng (tube 227-45) and 500 ng (227-50) of cDNA template each contained 3 PCR products 2 kb or larger. The PCR reaction and the DNA fragments from the gel were purified using QLAquick PCR purification kit (Qiagen Cat. 28106) and QLAquick gel extraction kit (Qiagen, Cat. 28704), respectively, Diagnostic PCR reactions were carried out on each of the 3 PCR products, and all 3 yielded the expected diagnostic PCR products using both the 5' end and 3' end primer pairs. Because they differed in size (~2 kb, 2.2 and 2.4 kb) and yet amplified with primers from the translation start and the 3'-untranslated region, all 3 may represent different alternatively spliced edg-4 transcripts.

The 3 PCR products were used as templates to reamplify human edg-4 with primers containing restriction sites suitable for cloning into an expression vecter. Two different 3'-end primers were selected with longer (HE4-DR3) or shorter (HE4-DR4) 3'-untranslated regions. The following PCR primers and PCR conditions were used:

```
                                           (SEQ. ID NO:8)
HE4-DF4 [5'-TTTAAAAAGCTTCCCACCATGGGCAGCTTGTACT-3']

(SEQ. ID NO:9)
HE4-DR3 [5'-TATATATCTAGACATTCACAAGAAATTACTCTGAGGC-
                                           3']

(SEQ. ID NO:10)
HE4-DR4 [5'-TATATATCTAGAGGAAATGTGACGAGGAGAGG-3']
```

Each reaction contained the following reagents:

| | |
|---|---|
| 5 µl | 10x PCR Buffer 3 |
| 1.0 µl | 25 mM dNTP mix |
| 1.5 µl | Primer HE4-DF4 (10 µM) |
| 1.5 µl | Primer HE4-DR3 or HE4-DR4 (10 µM) |
| 0.75 µ | Expand ™ enzyme (5 units) |
| 39.25 µl | water |
| 1 µl | DNA |
| PCR conditions: | |
| Incubate: | 94° C. for 2 min |
| 28 cycles: | 94° C. for 40 sec |
| | 60° C. for 40 sec |
| | 68° C. for 3.5 min |
| Incubate: | 68° C. for 8 min |
| Hold: | 4° C. |

The amplified fragments were purified using QLAquick PCR purification kit (Qiagen Cat. No.28106). The DNAs were resticted with HinDIII and XbaI, purified using QLAquick PCR purificaion kit (Qiagen Cat. No.28106) and QLAquick gel extraction kit (Qiagen, cat. no. 28704) and subcloned into HinDIII and XbaI-restricted pcDNA3 (Invitrogen; discontinued). Sequencing was carried out using fluorescent dye-labeled dideoxy terminators and an Perkin-Elmer/ABI 377 automated sequencing apparatus, with primers designed from vector sequences flanking the edg-4 insert, or from known rat or human edg-4 sequence. The human edg-4 sequence was compiled and assembled using the Lasergene DNAStar component SeqMan. Comparisons to rat edg-4 were carried out with the Wisconsin Group's GCG modules FRAMESEARCH, GAP, FASTA and BLAST.

A 1,170 bp span of the ~2.4 kb human edg-4 cDNA insert was sequenced extensively. The cDNA sequence as derived from clones pC3-hedg4#5 and pC3-hedg4#36 is presented in FIG. 15A. This region included 37 bp of putative 5'-untranslated region, a 1059 bp open reading frame (excluding the stop codon) corresponding to the complete human edg-4 coding region, and 74 bp of 3'-untranslated region adjacent to the coding region. This cDNA sequence showed 82.1% identity to the rat edg-4 cDNA sequence of GenBank entry U10699 over a 1129 bp region spanning the complete open reading frames of the rat and human edg-4 polypeptides, respectively.

The predicted human edg-4 translation product (FIG. 16A) showed 90.1% identity and 92.3% similarity to the rat EDG-4 polypeptide, consistent with its identification as the human ortholog of rat EDG-4. An alignment of the rat and human EDG-4 amino acid sequences is shown in FIG. 17A. The human EDG-4 polypeptide sequence has features typical of a G protein-coupled receptor, including 7 putative transmembrane domains, multiple potential intracellular phosphorylation sites and a single potential extracellular N-glycosylation site. The locations of these features are indicated in FIG. 16A.

FIGS. 15B and 16B illustrate the cDNA sequence and amino acid sequence, respectively, of the HEDG-4 receptor of clone pC3-hEdg4#36. FIG. 17B shows the alignment of the amino acid sequences of FIGS. 16A, 16B and the rat EDG-4.

EXAMPLE 15A

S1P Activation and Functional Response of the Cloned Human EDG-4 Receptor

Figure 18A:
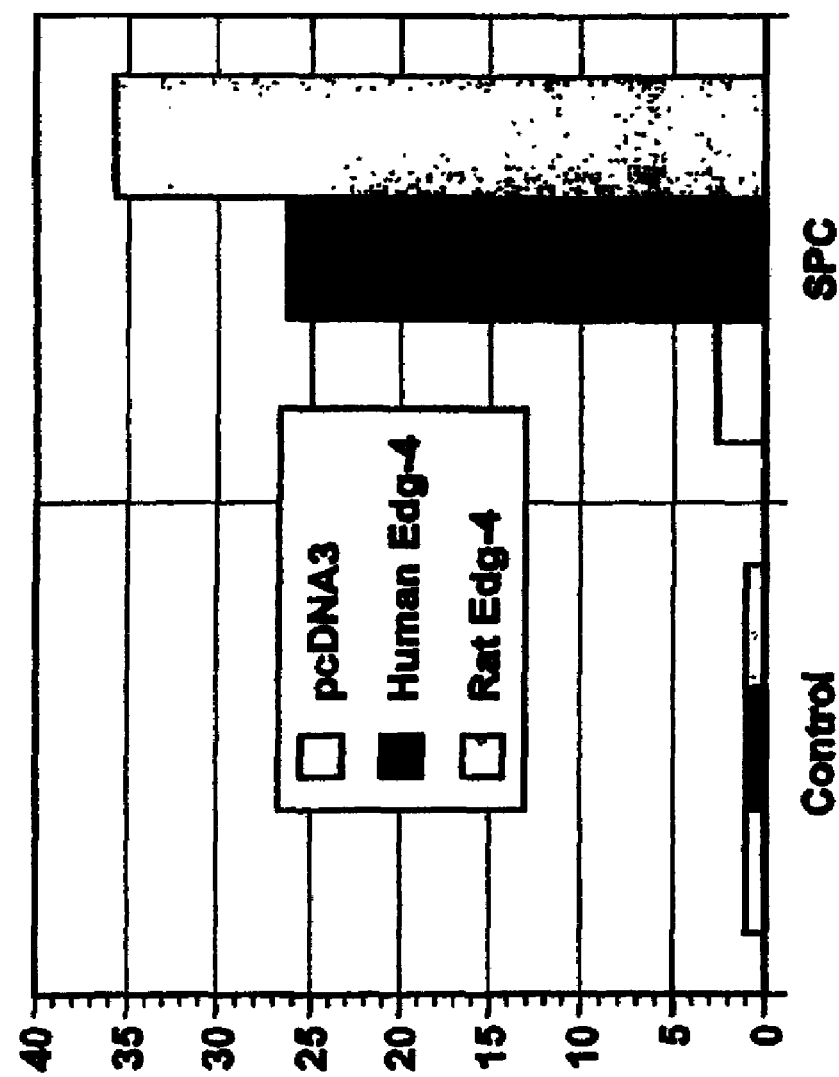
FIG. 18A illustrates the SRE reporter response to SPC in 293-EBNA cells cotransfected with a human or rat edg4 expression plasmid and an SRE reporter plasmid.

To determine whether the newly identified human EDG-4 gene product, like its rat counterpart, can respond to SPC via activation of a serum response element (SRE) reporter gene, the expression clone pC3-hedg4#36 was transfected into 293-EBNA cells together with a luciferase reporter bearing 2 copies of a consensus binding sequence for serum response factor. Transfection was accomplished using the Lipofectamine Plus kit (Life Technologies, Cat. 10964-013), using the manufacturer's recommended conditions. Optimal SRE induction was seen when cells were seeded so as to become 100% confluent at the time of treatment, 72–96 hr after transfection. The cells were serum-starved in medium with 0% to 0.15% serum for the last 72 hr before treatment, then treated in serum-free medium for 6 hr with 3 µM SPC, or with serum-free medium alone. Under these conditions, a control cotransfection with empty expression vector pcDNA3 gave about 2.5-fold induction of the SRE reporter, suggesting that a low level of S1P/SPC receptor was expressed endogenously the 293-EBNA cells. Human EDG-4 expression, in contrast yielded a 26.3-fold induction of the SRE reporter gene by 3 µM SPC (FIG. 18A). Similarly, rat edg-4 cotransfection with the SRE reporter gave a 35.6-fold induction of luciferase activity with 3 µM SPC. Thus, the human edg-4 cDNA encodes a functional S1P/SPC receptor, whose expression can be readily detected in 293-EBNA cells.

EXAMPLE 15B

Determination of Relative Potency and Efficacy of Human EDG-4 Receptor Agonists

One aspect of the present invention is a method for using recombinant human EDG-4 receptors in drug screening programs. Although the use of GPCRs in high-throughput screening is well known, no such screen has been reported for any edg receptor. More specifically, the novel human EDG-4 receptor presented herein can be used to identify and rank the relative potency and efficacy of potential agonists. These compounds may be useful inasmuch as they would be expected to trigger the survival-related signal transduction pathways associated with NF-κB induction. Equally, once a quantitative and reliable assay is established, it can readily be applied to identify and rank the relative potency and efficacy of receptor antagonists. This application, without limiting other aspects, of the screening methods described herein is specifically contemplated and incorporated within the scope of this invention.

Figure 18B:
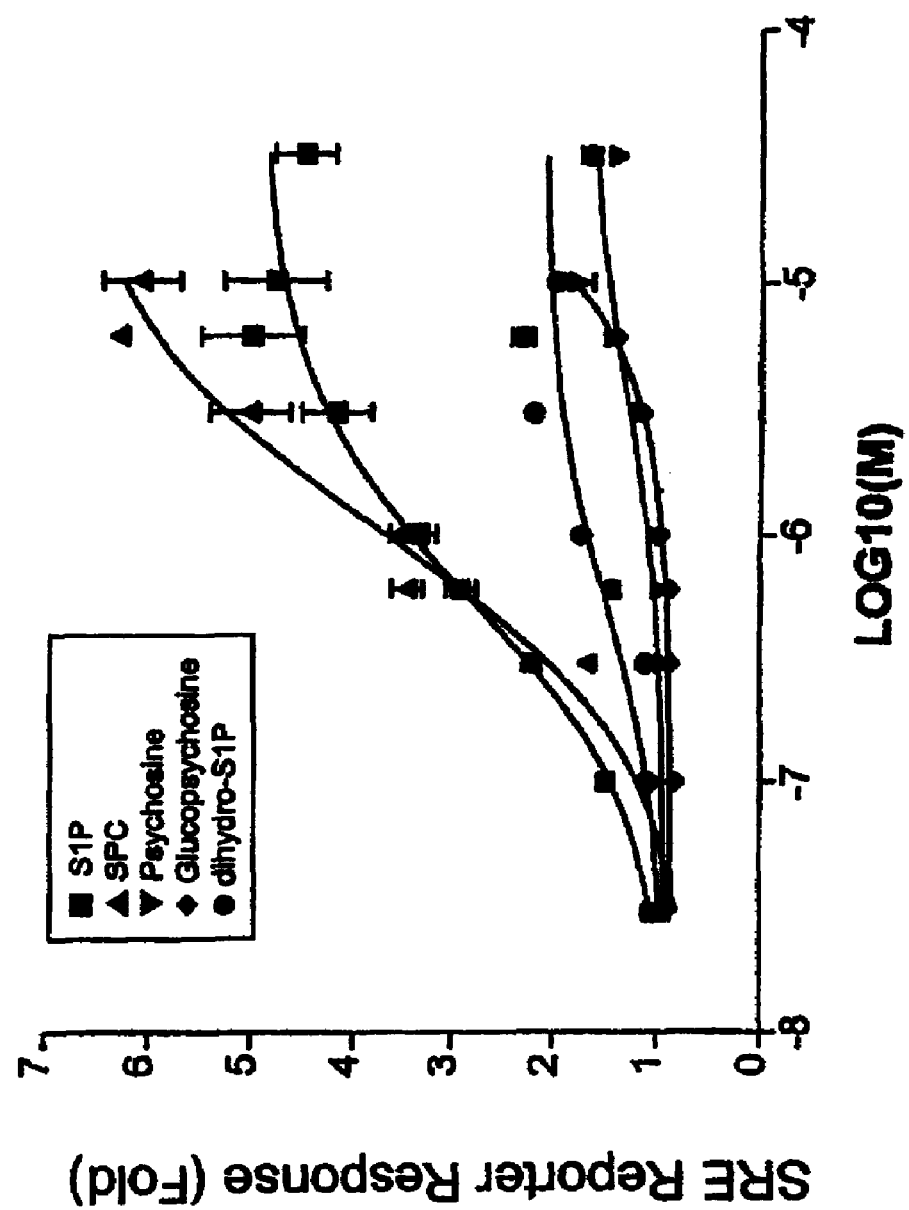
FIG. 18B illustrates the concentration-dependence of SRE response to S1P analogs in EDG-4 transfected cells.

Transfection of EDG-4, expression, pretreatment and treatment of 293-EBNA cells expressing recombinant human EDG-4 was carried out essentially as described in "Example 11. Heterologous Expression studies using Luciferas Assay." Various concentrations of S1P, SPC, psychosine, glucopsychosine or dihydrosphingosine 1-phosphate (dihydro-S1P) were applied in triplicate to cells in 96-well plates, and luciferase levels were measured after 6 h treatment. Results were tabulated in Microsoft Excel, and analyzed with GraphPad Prism sotfware. $EC_{50}$ values were determined using a fixed Hill-slope equation, unless variable slope significantly improved the fit to the data. The luciferase response was expressed as fold response, after subtracting any endogenous response in pcDNA3-transfected cells at a given concentration of compound. The experiment was repeated three times with similar results, and a representative experiment is shown in FIG. 18B.

Results: Table 2 summarizes the relative potency and efficacy of the compounds tested.

| Compound | $EC_{50}$ (µM) | Rank | Max. Fold | $E_{Max}$ (Percent) | Rank |
|---|---|---|---|---|---|
| S1P | 0.32 | 1 | 5.60 | 86.7 | 2 |
| SPC | 0.88 | 3 | 5.77 | 100 | 1 |
| Psychosine[a] | >10 | 4 | 1.78 | 30.9 | 5 |
| Glucopsychosin[a] | >10 | 4 | 1.81 | 31.4 | 4 |
| Dihydro-S1P | 0.53 | 2 | 2.84 | 49.2 | 3 |

[a]Cytotoxicity was seen at 10 µM or higher concentrations, preventing quantitative determination of $EC_{50}$ or $E_{Max}$ Results: From the results obtained here, it can be concluded that EDG-4 responds to both S1P and SPC as full agonists with similar potency and efficacy. In contrast, dihydro-S1P was a partial agonist under these assay conditions, despite an apparent potency similar to S1P and SPC. Thus, while the addition of a choline substituent to the phosphate headgroup did not greatly affect activity, the unsaturated carbon-carbon bond appears to play a role for full agonist activity. Psychosine and glucopsychosine both showed poor potency and efficacy, as well as cytotoxicity at higher concentrations. Nonetheless, these compounds did activate the receptor (since pcDNA3 activity was set to 1.0 at each concentration).

Published literature supports the existence of multiple receptors for S1P, and the identity of at least some of these with SPC receptor subtypes.

EXAMPLE 16

Role of Inflammatory Lysolipid Receptors in Nerve Growth Factor-mediated Inflammation and Neurotrophic Signal Transduction The use of sphingosine 1-phosphate (S1P) in suppressing programmed cell death is known (Cuvillier et al., 1996; Spiegel, 1998). However, since S1P was presumed to act as an intracellular second messenger, no receptor-based data were presented. Our own work shows that the G protein-coupled receptors (GPCRs) EDG-1 (Hla & Maciag, 1990), EDG-3 (Yamaguchi et al., 1996), EDG-4 (referred to in published literature as AGR16 [Okazaki et al., 1993] or H218 [MacLennan et al., 1994]) and HEDG4 as cloned herein, and EDG-7 (Munroe et al., unpublished; corresponding U.S. Ser. No. 60/070,185, incorporated herein by reference) respond to S1P and sphingosylphosphorylcholine (SPC) as an agonist. However, as shown in the previous examples and in Example 18 below, only two of the four S1P/SPC receptors signal through activation of NF-κB: EDG-3 and EDG-4. S1P has multiple biological activities including mitogenesis, neurite retraction, inhibition of cell motility, suppression of apoptosis and as we have found, inflammatory gene expression. Therefore, successful therapeutic use of S1P or its analogs hinges on recognizing which receptors are expressed and what their function(s) are in tissues exposed to the agent.

Direct modulation of NF-κB activation cascades has been proposed as a therapeutic mechanism for inflammation or apoptosis. However, NF-κB plays a vital role in innate immunity against ubiquitous microbial pathogens and in mobilizing the antigen-specific immune system. Therefore, rather than targeting this irreplaceable defense system, it would be preferred to instead block inappropriate activation of NF-κB through inflammatory S1P/SPC receptors, in situations where their agonists and/or receptor signaling are excessive or inappropriate. Alternatively, where NF-κB could prevent unwanted apoptosis or could enhance immune function in immunocompromised hosts, agonists of these receptors would be desirable, especially with favorable medicinal chemistry properties and selective pharmacology.

Because the sphingosine-phosphorylating enzyme sphingosine kinase (Edsall et al., 1997) and NF-κB (Rius et al., 1997) have both been shown to play critical roles in the neurotrophic action of NGF in the well-defined PC12 neuroblastoma model, we can surmise that the anti-apoptotic signaling pathway of NGF depends on both S1P and NF-κB. EDG-4 has been shown to be expressed in PC12 cells before, during and after NGF treatment (MacLennan et al., 1994). In CNS, the highest levels of edg-4 RNA are detected during embryogenesis. Immunohistochemical localization of CNS EDG-4 protein labels cell bodies and axons of young, differentiating neurons, consistent with the proposed role in neurotrophic function (MacLennan et al., 1997).

Since EDG-4 responds to S1P/SPC by activating NF-κB, it can be predicted that a causal link between S1P production (Edsall et al., 1997) and NF-κB activity (Rius et al., 1997) exists in PC12 cells. EDG-3, if expressed, could play a similar role. Although many steps in NGF signaling have been described, no report exists which links S1P to NF-κB in this system. In U937 cells, a single report does show that S1P treatment resulted in NF-κB activation (Shatrov et al., 1997). However, the authors did not show whether inflammatory gene expression such as IL-8 or IL-6 resulted, nor did they realize that a cell-surface receptor could be involved. Instead they assumed that S1P is an intracellular second messenger, as indeed did U.S. Pat. No. 5,712,262 (Cuvillier et al., 1996; Spiegel, 1998). We have now provided a molecular explanation of the link between these signaling steps. S1P acts on an inflammatory receptor subtype such as EDG-4 or EDG-3. This in turn leads to the activation of the $G_{i/o}$, heterotrimeric protein complex, triggering downstream events that depend on tyrosine kinase(s) and reactive oxygen species. Finally, NF-κB is activated, resulting in anti-apoptotic gene expression.

Two receptors exist for NGF on PC12 cells and many other neuronal and non-neuronal cell types. One of these, TrkA, is a high-affinity NGF receptor which signals through a classical dimeric transmembrane tyosine kinase receptor mechanism. The other, p75$^{NGFR}$, is a low affinity receptor for NGF and several other neurotrophins, belongs to the "death receptor" gene family including TNFR, Fas/CD95 and CD28, and signals through a sphingomyelinase pathway using ceramide and/or sphingosine as key pro-apoptotic intermediates. In fact, p75$^{NGFR}$ expression in the absence of TrkA causes NGF to induce apoptosis, rather than survival of PC12 cells. TrkA co-expression with p75$^{NGFR}$ is required for NGF to display neurotrophic activity in PC12 cells; expression of TrkA alone is without effect on apoptosis.

Without wishing to be bound by theory, it appears that TrkA confers neurotrophic activity on NGF as follows. Sphingosine kinase (SK) is an enzyme that converts the pro-apoptotic sphingosine into S1P. S1P has been shown to actively suppress programmed cell death induced by death receptor ligands or ceramide (Cuvillier et al., 1996; Spiegel, 1998). SK is induced by NGF in PC12 cells that co-express TrkA and p75$^{NGFR}$, but not when the tyrosine kinase activity of TrkA is inhibited with K252a (Edsall et al., 1997). Therefore, it appears that the induction of sphingosine kinase converts a p75$^{NGFR}$ death signal (ceramide/sphingosine) into a survival signal (S1P). Given the presence of EDG-4 (and perhaps EDG-3) in PC12 cells, the production of S1P via sphingosine kinase would be expected to lead to activation of the GPCR, thereby activating NF-κB. NF-κB, in turn, already known to be essential for neurotrophic responses to NGF (Rius et al., 1997). Thus, inflammatory S1P receptors play a pivotal role in directly linking these two essential steps in NGF neurotrophic signaling.

Like p75$^{NGFR}$, several other death receptors have been shown to induce apoptosis and/or NF-κB activation, depending on the cell type and costimulus applied. The involvement of sphingomyelinase, ceramide/sphingosine and sphingosine kinase in the signaling cascade has also been shown repeatedly with TNFR, Fas/CD95 and other family members. Another parallel with the NGF system is the observation that some cell types that express a given death receptor survive their ligands while other do not. Again, protein kinase C is implicated in survival pathways. There is even direct evidence that S1P plays a similar role in survival for Fas/CD95 and inflammatory gene expression for TNFR. Therefore, one can predict a widespread role for inflammatory lysosphingolipid/edg receptors in modulating the apoptotic/inflammatory potential of death receptor ligands. If true, these GPCRs may play a fundamental role in cell survival, differentiation, and inflammation. Therefore, methods for isolating such receptors, and for identifying ligands at modulate these activities constitute aspects of the invention described herein.

The ligands for other GPCRs known to activate NF-κB are generally peptides or small molecules produced in a very limited range of cell types. However, the sphingolipids and sphingomyelinase which are ubiquitously distributed can be used to generate ligands for the edg receptors. Therefore, potentially every cell type can make ligands for these receptors. Moreover, ceramide and/or sphingosine are synthesized as an integral part of the death receptor signaling pathways, so that survival may require as little as a single additional metabolic conversion to S1P, provided the appropriate S1P receptors are present. While TrkA provides the signal to induce SK in PC12 cells, other inducers of protein kinase C have also been shown to induce SK expression. One of these is the potent tumor promoter phorbol ester. Thus, other costimulators may dramatically change or even reverse the outcome of death receptor signaling through the inflammatory S1P/SPC receptors.

Screening of individual S1P/SPC receptors will permit the identification and optimization of selective ligands for use in modulating apoptosis and inflammation. For example, SPC shows greater activity than S1P acting on EDG-4, whereas the 2 compounds have similar activity on the EDG-3 receptor. While anti-apoptotic compounds directed at these targets are difficult to identify without the receptor assays, selective pro-apoptotic compounds are even harder to target, since many enzyme inhibitors can trigger apoptotic pathways. Furthermore, since it now appears that edg receptor-induced NF-κB is one mechanism by which S1P suppresses apoptosis, inflammatory gene expression is also expected to occur. A further implication is the potential for immune stimulation with EDG-3 or EDG-4 agonists, including S1P and SPC. Antagonists, on the other hand, could be used to treat transplant rejection or autoimmune diseases, in which both inflammatory responses and insufficient apoptosis of auto/alloreactive T cells play a role.

EXAMPLE 17

Three Inflammatory Subtypes of Lysophosphatidic Acid (LPA) Receptor

LPA, like S1P, is abundant in serum, but not plasma. Moreover, LPA is produced as a consequence of phospholipase $A_2$ with or without the contribution of phospholipase D (depending on the phospholipid substrate). Our results showing IL-8 production in HUVEC exposed to 5 μM LPA further suggest that inflammatory responses could be mediated by some, or all, LPA receptors. To date we have identified three subtypes of edg receptors that respond to LPA as an agonist. These are EDG-2, EDG-6 and EDG-5 (referred to also as $LP_{A1}$, $LP_{A2}$ and $LP_{A3}$, respectively (Chun, J, Contos, JJA and Munroe, DG. 1998. A growing family of receptor genes for lysophophatidid acid (LPA) and other lyso-phospholipids. Cell Biochem Biophys (in press)). The EDG-5 receptor is set out in co-pending U.S. application Ser. No. 08/997,803 to MUNROE et al., incorporated herein to reference and the amino acid sequence and cDNA sequence for the EDG-6 receptor is set out in FIGS. 21 and 22, respectively. To determine whether these receptors might mediate inflammatory responses, each was cotransfected separately with SRE, NF-κB or AP-1 reporter genes. The AP-1 reporter contained approximately 1 kb of the human collagenase II promoter, and the first 50 bp of the 5'-untranslated region of the collagenase II transcription unit (Angel P, et al. 1987. Phorbol ester-inducible genes contain a common cis element recognized by a TPA-modulated trans-acting factor. Cell 49:729–739), a region whose inducible expression has been shown to be controlled by AP-1. This transcription factor, like NF-κB has been implicated in inflammatory and neoplastic signal transduction, though the gene targets of its action are largely distinct from those of NF-κB (Adcock I M. 1997. Transcription factors as activators of gene transcription; AP-1 and NF-κB. Monaldi Arch Chest Dis 52:178–186. Review).

293-EBNA cells were grown, lipofected in monolayer cultures, and pretreated as described above for Example 11, assay #1, except that NF-κB and AP-1 reporter-transfected cells were preteated for 6 hr in medium containing 0.5% PBS, then treated overnight in the same medium with or without 10 μM LPA.

Figure 23:
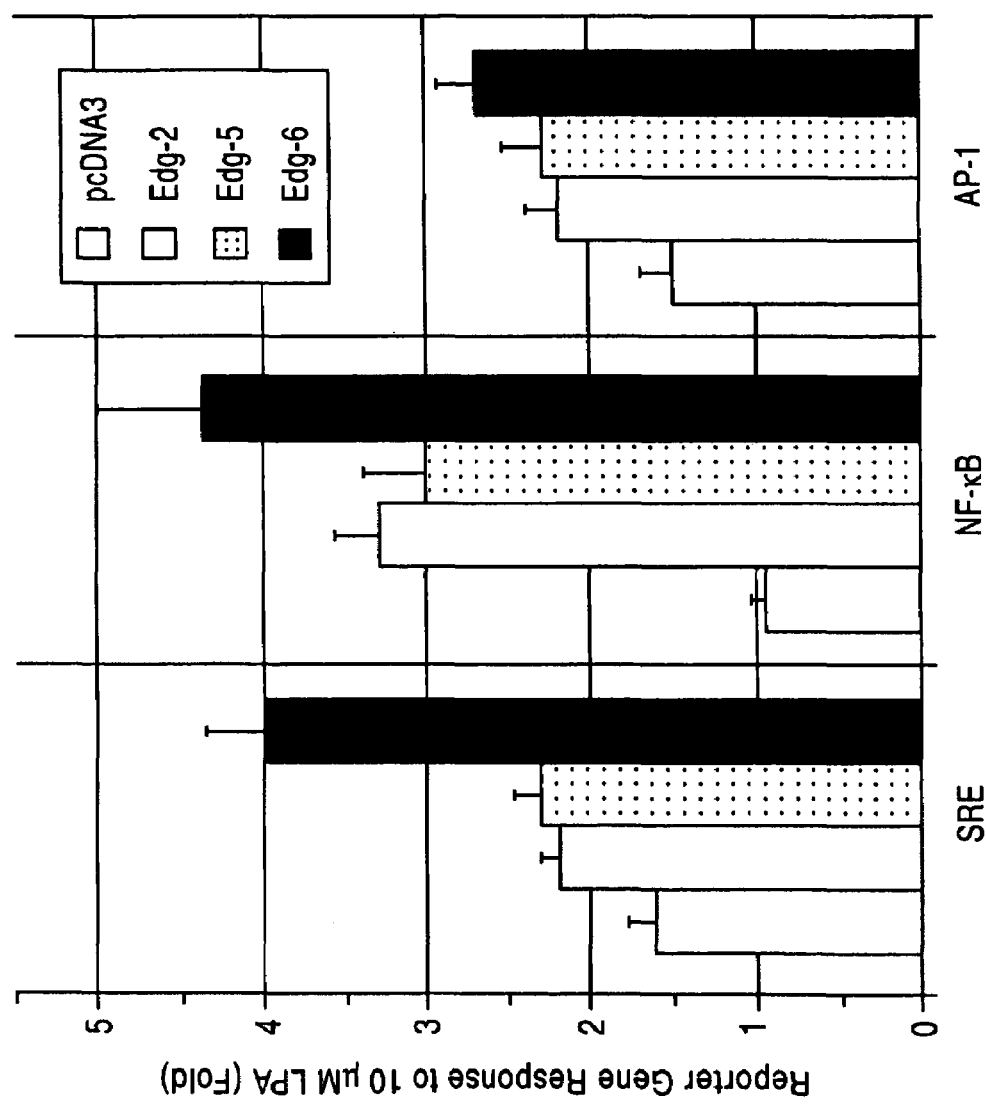
FIG. 23 illustrates that the three LPA receptor subtypes signal through NF-B and AP-1 genes.

Results: As shown in FIG. 23, all three receptors robustly activated the NF-κB reporter (about 3–4-fold) in the presence of 10 μM LPA, while no response to LPA was seen when the NF-κB reporter was cotransfected with the empty expression vector pcDNA3. With the SRE and AP-1 reporter genes, some endogenous response to LPA was seen (about 1.5-fold vs untreated control cells). However, EDG-6 strongly induced both reporters, while EDG-2 and EDG-5 caused greater than 2-fold induction of the SRE and AP-1 reporters with LPA. Therefore, all three LPA receptors tested here are capable of inducing inflammatory gene transcription through NF-κB, and perhaps, AP-1 as well. As mentioned, these two inflammatory transcription factors respond to different signaling pathways by inducing distinct gene sets. However, some genes are powerfully and synergistically activated by both factors acting in concert (Stein B, et al. 1993. Cross-coupling of the NF-κB p65 and Fos/Jun transcription factors produces potentiated biological function. EBMO J 12:3879–3891). Thus, the LPA receptors EDG-2, EDG-5 and EDG-6 are likely to respond to LPA or other lysolipid agonists by activating one or both sets of gene targets controlled by NF-κB and AP-1. Since phospholipase action and NF-κB/AP-1 activation are common features of many diseases with an inflammatory or immune component, it is also possible that edg/LPA receptors exacerbate a pre-existing disease or injury through their inflammatory responses to lysolipids. Therefore, antagonists of one or more of these inflammatory receptors could be useful in treating such diseases. Without limiting the intended scope of the inventions disclosed, examples include rheumatoid arthritis, stroke, neurotrauma, Alzheimer's disease, ALS, asthma, endotoxic shook, atherosclerosis and many other diseases. Besides inflammation, activation of NF-κB is likely to promote survival in the face of pro-apoptotic signals, for example, those initiated by the TNF receptors or other "death receptors". (Van Antwerp D J, et al. 1998. Inhibition of TNF-induced apoptosis by NF-κB. Review. Trends Cell Biol 8:107–111) This may explain the observed reduction in efficacy of chemotherapy-induced apoptosis in LPA-treated ovarian cancer cells. (Frankel A, et al. 1996. Peptide and lipid growth factors decrease cis-diamminedichloroplatinum-induced cell death in human ovarian cancer cells. Clin Cancer Res 2:1307–1313) With the present disclosure, antagonists of inflammatory LPA receptors may be discovered and optimized to reduce or delay the emergence of cancer cell populations immune to the apoptosis-inducing effects of chemotherapeutics. Such therapies may also be used to treat autoimmunity or other diseases where excessive or inappropriate cell survival occurs. Alternatively, agonists of inflammatory LPA receptors may be neuroprotective, or promote revival of other cell types in diseases where inappropriate or excessive cell death occurs. Examples include HIV/AIDS, myelodysplasia, endotoxic shock, cirrhosis of the liver, to name a few.

EXAMPLE 18

Calcium Microfluorimetry as a Real-time Readout of EDG Receptor Functional Responses Reporter gene assays, while very useful, produce an endpoint assay result, and therefore cannot give information about transient, reversible or desensitizing responses initiated by EDG receptors. Calcium microfluorimetry is one example of an alternative approach that does allow such information to be gathered. Since $Ca^{2+}$ responses to S1P or LPA have been observed in cells that endogenously express their receptors (Tomquist K, et al. 1997. Sphingosine 1-phosphate mobilizes sequestered calcium, activates calcium entry, and stimulates deoxyribonucleic acid synthesis in thyroid FRTL-5 cells. Endocrinology 138:4049–4057; Holtsberg F W, et al. 1997. Lysophosphatidic acid induces a sustained elevation of neuronal intracellular calcium. J Neurochem. 69:68–75) we tested 293-EBNA cells transiently transfected with different EDG receptors for functional responses via calcium microfluorimetry.

Transfections were carried out with EDG receptors in 293-EBNA cells as described above, except that no reporter gene vector was included in the DNA mix. Two days after transfection, cells were harvested by trypsinization and plated at a density of 200,000 cells onto poly-D-lysine-coated coverslips in 100 μl of medium containing 0.5% FBS. After briefly allowing cell attachment to take place, 2 ml of medium without FBS was added and the cells were incubated overnight. The next day, cells were loaded with 5 μM fura-2 AM ester (Molecular Probes) for 60 min at RT, then washed and used for calcium microfluorimetry. S1P was prepared as a 10 mM stock in 100% ethanol and diluted to a final concentration of 2 μM in ACSF; PMA was used at a final concentration of 25 ng/ml. Treatments were applied using a gravity-fed perfusion apparatus. Fluorescence emission was continuously monitored and recorded with PTI 2.060a software and analyzed with Sigma Plot software. Intracellular calcium concentrations were calculated by interpolation on a ratiometric fluorescence curve generated from fura-2 fluorescence in a calcium dilution series.

Figure 19:
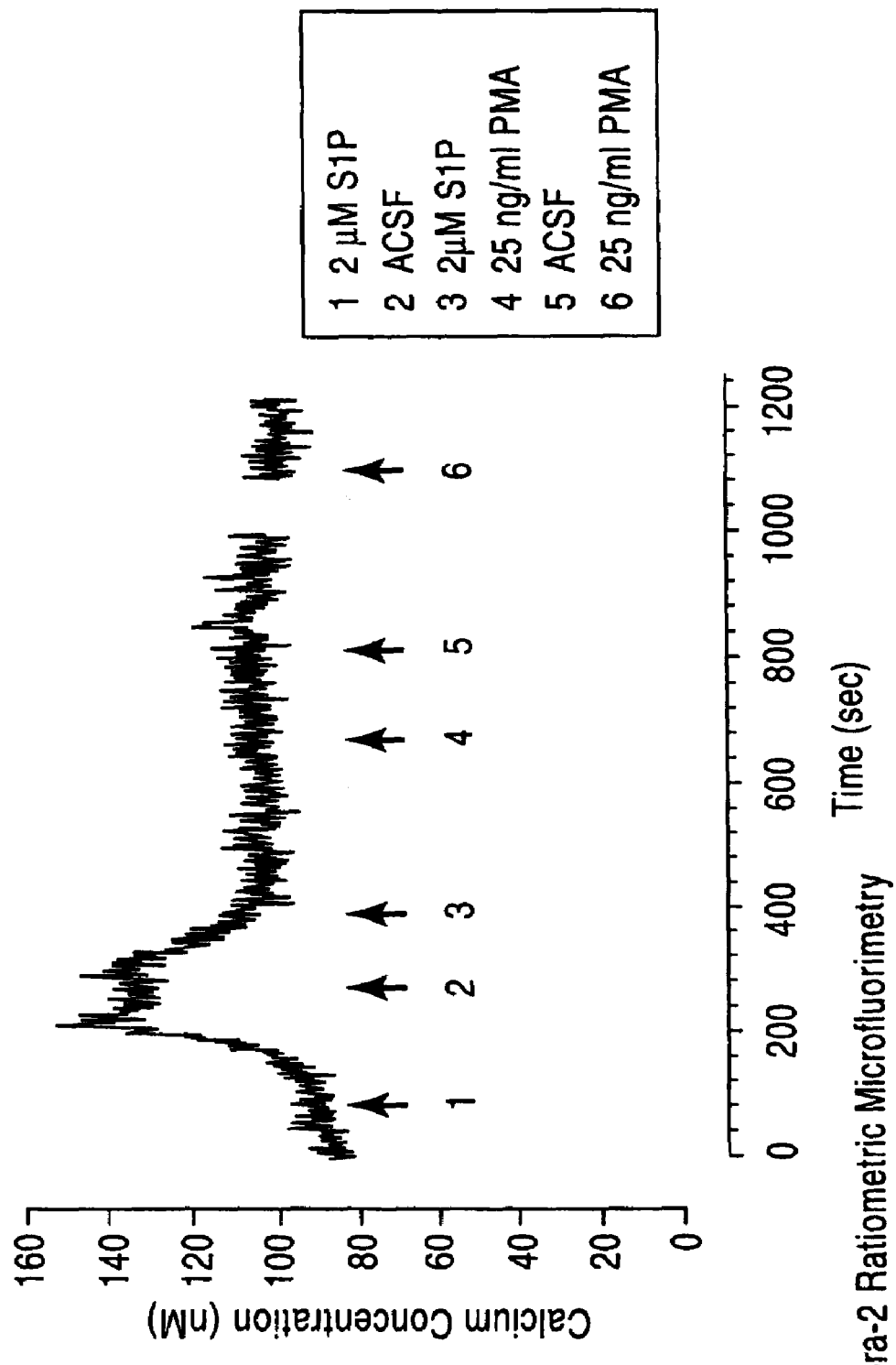
FIG. 19 illustrates the intracellular calcium response to S1P in cells transfected with the empty expression vector pcDNA3.
Figure 20:
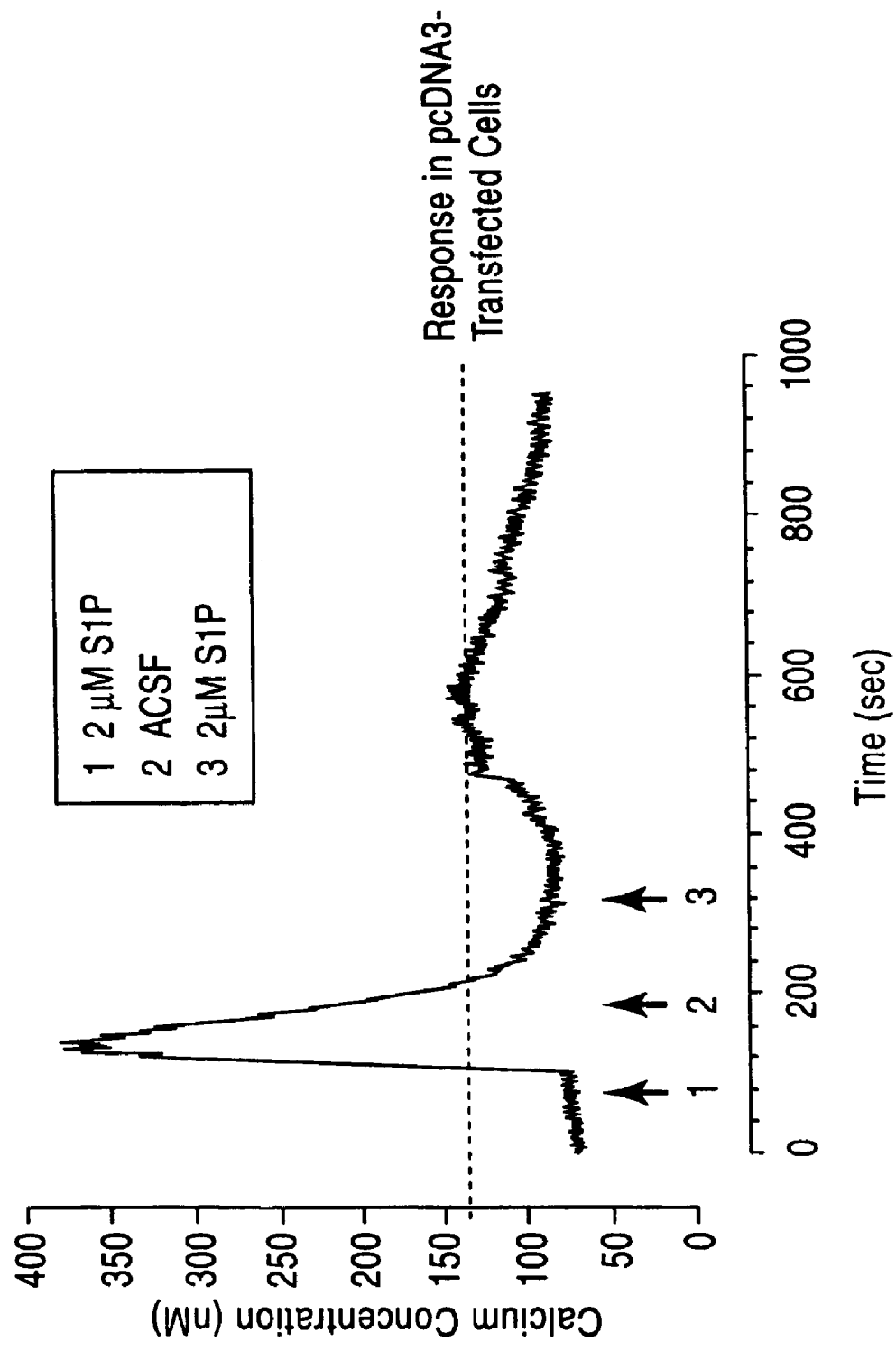
FIG. 20 illustrates the intracellular calcium response to S1P in cells transfected with human EDG-3 expression vector.

Results: FIG. 19 shows the response of control cells transfected with pcDNA3 and treated with 2 μM S1P. A small increase in intracellular calcium concentration was observed with 2 μM S1P, and this response completely desensitized the response to a second application of S1P. FIG. 20 shows the calcium response to S1P in EDG-3 transfected cells. In contrast to the approximately 60 nM change in intracellular calcium in pcDNA3-transfected cells, a 300 nM increase was observed in EDG-3 transfected cells treated with 2 μM S1P. A second application of S1P elicited a small response, though desensitization clearly occurred. The Table below shows a qualitative analysis of preliminary data we have obtained from cells expressing each EDG receptor, after addition of the appropriate agonist at a 2 or 10 μM concentration.

TABLE

Qualititative calcium response of EDG-transfected cells to receptor agonists.

| Receptor | Agonist | Concentration | Response |
|---|---|---|---|
| EDG-1 | S1P | 2 and 10M | None within 20 min |
| EDG-2 | LPA | 10M | ++ |
| EDG-3 | S1P | 2 and 10M | +++ |
| EDG-4 | S1P | 2 and 10M | +++ |
| EDG-5 | LPA | 2 and 10M | +++ |
| EDG-6 | LPA | 2 and 10M | +++ |
| EDG-7 | S1P | 2 and 10M | None within 20 min |

While further experiments are required to quantitatively assess the capacity of these receptor subtypes to elevate intracellular calcium, initial results strongly suggest a correlation of calcium signaling with induction of inflammatory response pathways. Supporting this conclusion, EDG-1 and EDG-7 both respond through the SRE reporter to S1P, yet fail to signal through NF-κB reporters or increases in intracellular calcium. The fact that only two of the four identified S1P receptors signal through NF-κB indicates that effective anti-inflammatory or survival-modulating therapeutics can best be developed using the inventions disclosed herein, which specifically measure the relevant receptor subtypes and pathways as indicators of therapeutic efficacy.

Therefore, NF-κB reporter genes, other endpoint assays that measure inflammatory signal transduction or gene expression, and real-time functional assays that monitor inflammatory signaling by edg/LL receptors are specifically encompassed within the scope of the present invention.

EXAMPLE 19

Construction and Functional Testing of a Human EDG-4 Fusion Protein with Jellyfish Green Fluorescent Protein (GFP)

Chimeric proteins may be used to study the structure, function, mechanism of activation or biological role of a protein. In the case of edg receptors, little is known of their intracellular trafficking, post-translational processing, or physical interaction with other proteins. The green fluorescent protein (GFP) from *Aequorea victoria* has been used as a tool for the direct visualization of various fusion proteins in living cells, since no fixation or substrate addition is required to obtain fluorescence. Numerous examples exist of different proteins that retain function after fusion to GFP, including at least some GPCRs. (Kallal L, et al. 1998. Visualization of agonist-induced sequestration and down-regulation of a green fluorescent protein-tagged beta2-adrenergic receptor. J Biol Chem 273:322–328) To address questions of EDG-4 trafficking and protein-protein interactions, we constructed a GFP fusion with human EDG-4 cDNA and tested for a functional response to S1P using the SRE reporter gene as a readout.

A pair of primers was designed from two ends of reading frame of human edg-4 cDNA sequence to engineer the edg-4 open reading frame into a vector designed for GFP fusion protein expression, with the GFP tag carboxy-terminal to the full-length EDG-4 polypeptide:

5'-End Primer: Contains Site for Kpn I enzyme and optimized (Kozak) translation initiation sequence:

HE4-ATG KpnF: [5'-TTTAAAGGTACCGCCAC-CATGGGCAGCTTGTAC-3'](SEQ. ID NO:11)

3'-End Primer: Contains site for XbaI enzyme, and lacks naturally-occurring edg-4 stop codon:

HE4-xba/1096R: [5'-TATATATCTAGAGACCACCGTGT-TGCCCTCCAG-3'](SEQ. ID NO:12)

pc3-hedg4#36 plasmid DNA was amplified with the above pair of primers under the following conditions of PCR amplification, using the Expand™ PCR system from Boehringer Mannheim (Cat. 1681–842).

The reaction contained the following reagents:

| | |
|---|---|
| 5 µl of 10x PCR Buffer 3 | |
| 1.0 µl of 25 mM dNTP mix | |
| 1.5 µl of Primer HE4-ATG KpnF (10 pmol/l) | |
| 1.5 µl of Primer HE4-xba/1096R (10 pmol/l) | |
| 0.75 µl of Enzyme (2 units) | |
| 39.25 µl water | |
| 1 µl DNA | |
| PCR conditions: | |
| Incubate: | 94° C. for 2 min |
| 10 cycles: | 94° C. for 1 min |
| | 50° C. for 1 min |
| | 68° C. for 2 min |
| 20 cycles: | 94° C. for 1 min |
| | 68° C. for 3 min |
| Incubate: | 68° C. for 8 min |
| Hold: | 4° C. |

The amplified reaction (designated as sample 80727-3) was purified using QLAquick PCR purification kit (Qiagen Cat.28106). The DNA was restricted with KpnI and Xba I enzymes, and subcloned into Kpn I and XbaI restricted pcDNA3.1/CT-GFP (Invitrogen, Cat. K4820-01). Three positive clones i.e. E4-GFP#8-3, E4-GFP#15-3, E4-GFP#17-3 were identified, sequenced to confirm the expected insert and cloning junction, and tested by lipofection into 293-EBNA cells as described above for hum edg-4 cDNA.

Figure 24:
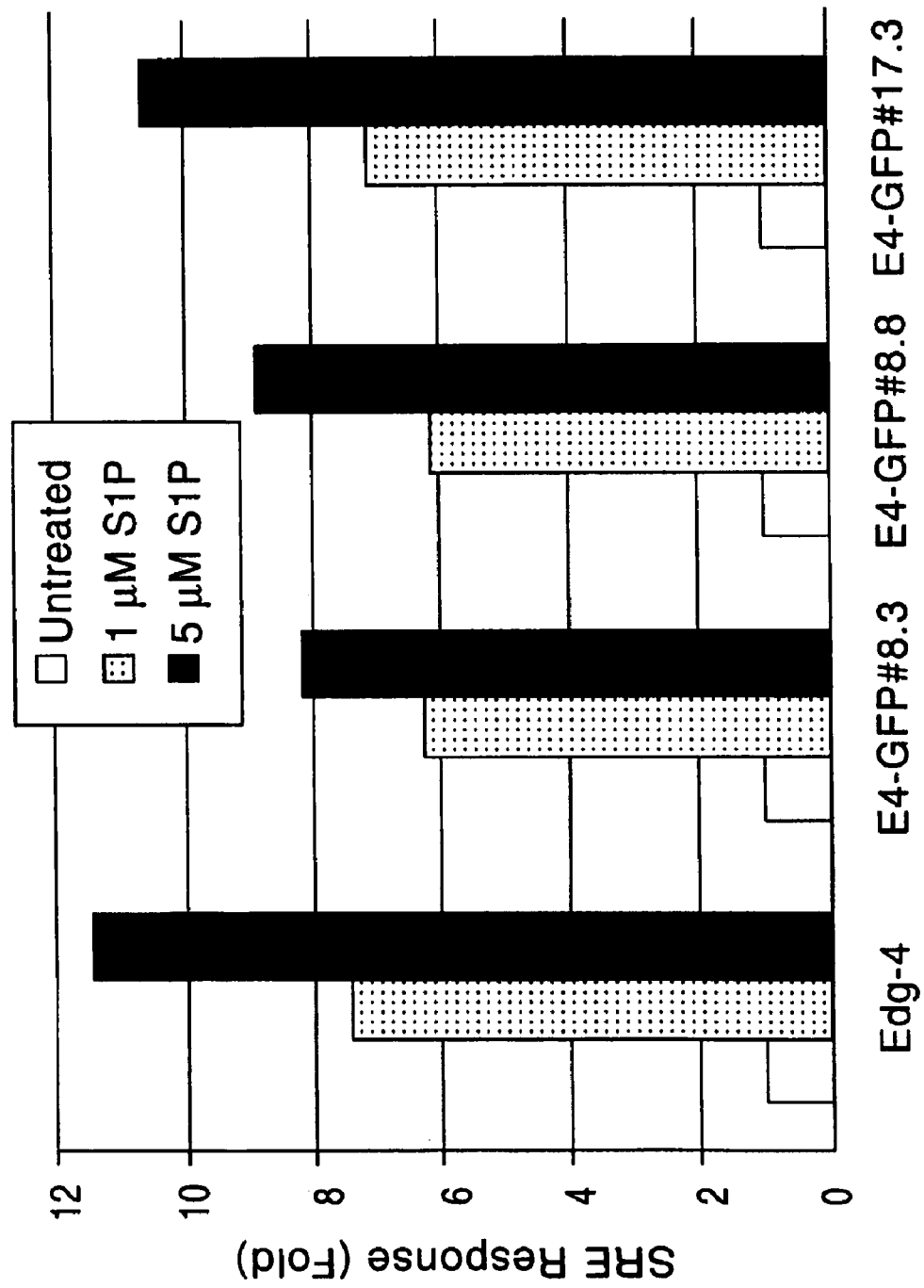
FIG. 24 illustrates the SRE Response for a human EDG-4 fusion protein with Jellyfish Green Fluorescent Protein (GFP).

Results: Cells were observed under fluorescence microscopy using a fluorescein filter set. Cells expressing the EDG-4/GFP fusion protein were easily identified due to their bright green fluorescence. In untreated, serum-starved cells most of the fluorescence was peripherally located, apparently at the plasma membrane. However, 72 hr after transfection, high levels of the GFP fusion protein accumulated in discrete clusters which might be "capped" on the cell surface or, alternatively, internalized in vesicles. A control transfection with a nonfusion GFP constrtuct revealed only a diffuse cytoplasic localization of GFP fluorescence. Importantly, the EDG-4/GFP receptors could be directly visualized in living cells without special fixing or development. Thus, trafficking and interaction of EDG-4/GFP with various organelles may be followed in living cells before, during and after addition of agonists and/or pharmacological treatments. Such localization would only be meaningful, of course, if the receptors bind ligands and activate signal transduction pathways normally. Results of SRE reporter gene cotransfection and response to 1 or 5 μM S1P are shown in FIG. 24. All clones of EDG4/GFP did not differ significantly from the EDG-4 parent expression vector in SRE response to S1P. Thus, despite the fairly large fusion domain presented by GFP, apparently normal ligand-responsiveness and intracellular signaling was retained. Visualization and quantitation of fusion receptor internalization offers an alternative means of assessing functional activation of EDG-4 receptor, for example, in pharmacological evaluation of partial agonists EDG-4.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments.

REFERENCES

An, S, Bleu, T, Huang, W, Hallmark, O G, Coughlin, S R and Goetzl, E J. 1997. Identfication of cDNAs encoding two G protein-coupled receptors for lysosphingolipids. FEBS Lett 417:279–282.

Carter, B D, Kaltschmidt, C, Kaltschmidt, B, Offehauser, N, Bohm-Matthaei, R. Baeuerle, P and Barde, Y-A. 1996. Selective activation of NF-κB by nerve growth factor through the neurotrophin receptor p75. Science 272: 542–545.

Cuvillier, O, Pirianov, G, Kleuser, B, Vanek, P G, Coso, O A, Gutkind, J S and Spiegel, S. 1996. Suppression of programmed cell death by sphingosine-1-phosphate. Nature 381: 800–803.

Cuvillier, O, Rosenthal, D S, Smulson, M E and Spiegel, S. 1998. Sphingosine 1-phosphate inhibits activation of caspases that cleave poly(ADF-ribose) polymerase and lamins during Fas- and ceramide-mediated apoptosis in Jurkat T lymphocytes. J Biol Chem 273: 2910–2916.

Edsall, L C, Pirianov, G O and Spiegel, S. 1997. Involvement of sphingosine 1-phosphate in nerve growth factor-mediated neuronal survival and differention. J Neurosci 17: 6952–6960.

Hla, T and Maciag, T. 1990. An abundant transcript induced in differentiating human endothelial cells encodes a polypeptide with structural similarites to C-protein-coupled receptors. J Biol Chem 265: 9308–9313.

Lee, M-J, Van Brocklyn, J R, Thangada, S, Liu, C H, Hand, A R Menzeleev, R, Spiegel, S and Hla T. Sphingosine-1-phosphate as a ligand for the G protein-coupled receptor EDG-1. Science 279: 1552–1555.

MacLennan, A J, 1996. Molecular cloning and expression of G-protein coupled receptors. U.S. Pat. No. 5,585,476. Issued Dec. 17, 1996.

MacLennan, A J, Browe, C S, Gaskin, A A, Lado, D C and Shaw, G. 1994. Cloning and characterization of a putative G-protein coupled receptor potentially involved in development. Mol Cell Neurosci 5: 201–209.

MacLennan A J, Marks, L, Gaskin, A A and Lee, N. 1997. Embryonic expression pattern of H218, a G-protein coupled receptor homolog, suggests rates in early mammalian nervous system development. Neuroscience 79: 217–224.

Okazaki, H, Ishizaka, N, Sakurai, T, Kurokawa, K, Goto, X, Kumada, M and Takuwa, Y, 1993. Molecule cloning of a novel putative G protein-coupled receptor expressed in the cardiovascular system. Biocehm Biophys Res Commun 190: 1104–1109.

Rius, R A, Edsall, L C and Spiegel, S. 1997. Activation of sphingosine kinase in pheochromocytoma PC12 neuronal cells in response to trophic factors. FEBB Lett 417: 173–176.

Shatrov, V A, Lehmann, V and Chouaib, S. 1997. Sphingosine-1-phosphate mobilizes intracellular calcium and activates transcription factor NF-κB in U937 cells. Biochem Biophys Res Commun 234: 121–124.

Spiegel, S. 1998. Use of sphingosine-1-phosptate to suppress progrmamed cell death. U.S. Pat. No. 5,712,262. Issued Jan. 27, 1998.

Taglialatela, G, Robinson, R and Perez-Polo, J R. 1997. Inhibition of nuclear factor kappa B (NFκB) activity induces nerve growth factor-resistanit apoptosis PC12 cells. J Neurosci Res 47: 155–162.

Yamaguchi, F. Tokuda, M, Hatase, O and Brenner, S. 1996. Molecular cloning of the novel human G protein-coupled receptor (GPCR) gene mapped on chromosome 9. Biochem Biophys Res Commun 227: 608–614.

Zondag, G C M, Postma, F R, van Etten, I, Verlaan, I and Moolenaar, W H. 1998. Biochem J 330

```

We claim:

1. A method of identifying a compound as an agonist for an EDG receptor, wherein agonist activation of the EDG receptor activates NF-κB, comprising the steps of:
   a. culturing cells which express said EDG receptor in medium with low-serum or defined medium designed to reduce basal levels of NF-κB activation;
   b. contacting said cultured cells with said compound to be tested for agonist activity at said EDG receptor; and
   c. identifying the compound as an agonist by quantitatively determining NF-κB activation in said cultured cells.

2. The method according to claim 1, wherein said receptor is selected from the group consisting of EDG-2, EDG-3, EDG-4, EDG-5 and EDG-6.

3. A method of identifying a compound as an agonist for an EDG receptor, wherein agonist activation of the EDG receptor produces IL-8, comprising the steps of:
   a. culturing cells which express said EDG receptor in a medium with low-serum or medium designed to reduce basal levels of IL-8 production;
   b. contacting said cultured cells with a candidate compound to be tested for agonist activity at said receptor; and
   c. identifying the compound as an agonist by quantitatively determining IL-8 production in said cultured cells.

4. The method according to claim 3, wherein said receptor is EDG-4.

5. A method of identifying a compound as an antagonist for an EDG receptor, wherein agonist activation of the EDG receptor activates NFκB, comprising the steps of:
   a. culturing cells which express an EDG receptor in a medium with low-serum or medium designed to reduce basal levels of N F-KB activation;
   b. contacting said cultured cells with a mixture comprising an agonist and a compound to be tested for antagonist activity at said receptor, wherein said agonist is selected from lysolipid or 20% FBS; and
   c. identifying the compound as an antagonist by quantitatively determining NF-κB activation in said cultured cells.

6. The method of claim 5, wherein said receptor is selected from the group consisting of EDG-2, EDG-3, EDG-4, EDG-5 and EDG-6.

7. A method of identifying a compound as an antagonist for an EDG receptor, wherein agonist activation of the EDG receptor produces IL-8, comprising the steps of:
   a. culturing cells which express an EDG receptor in a medium with low-serum or defined medium designed to reduce basal levels of IL-8 production;
   b. contacting said cultured cells with a mixture comprising an agonist and a compound to be tested for antagonist activity at said receptor, wherein said agonist is an lysolipid or 20% FBS; and
   c. identifying the compound as an antagonist by quantitatively determining IL-8 production in said cultured cells.

8. The method of claim 7, wherein said receptor is EDG-4.

9. A method of identifying a compound as an agonist of an EDG receptor with the amino acid sequence selected from the group consisting of (i) the amino acid sequence comprising SEQ ID NO: 17 and (ii) the amino acid sequence comprising SEQ ID NO: 22, comprising the steps of:
   a. culturing cells which express an EDG receptor;
   b. contacting said cultured cells with a compound to be tested for an agonist activity at said receptor; and
   c. measuring a response indicative of the degree of an agonist activity, wherein the response measured in step (c) is selected from the group consisting of activation of NFκB, activation of Serum Response Element (SRE), activation of AP-1, and increase in intracellular calcium levels.

10. The method according to claim 9, wherein the response in step (c) is activation of NFκB, or activation of Serum Response Element (SRE), and is measured through a reporter assay.

11. The method according to claim 9, wherein the response in step (C) is activation of NFκB and is measured by determining the level of cytokines production.

12. The method according to claim 11, wherein the cytokines are selected form the group consisting of IL-8, IL-6, and GM-CSF.

13. The method according to claim 12, wherein the level of cytokine production is determined using ELISA.

14. A method of identifying a compound as an antagonist of an EDG receptor with the amino acid sequence selected from the group consisting of (i) the amino acid sequence comprising SEQ ID NO: 17 and (ii) the amino acid sequence comprising SEQ ID NO: 22, comprising the steps of:
   a. culturing cells which express an EDG receptor;
   b. contacting said cultured cells with a compound to be tested for an antagonist activity at said receptor; and
   c. measuring a response indicative of the degree of an antagonist activity, wherein the response measured in step (c) is selected from the group consisting of activation of NFκB, activation of Serum Response Element (SRE), activation of AP-1, and increase in intracellular calcium levels.

15. The method according to claim 14, wherein the response in step (c) is activation of NFκB, or activation of Serum Response Element (SRE), and is measured through a reporter assay.

16. The method according to claim 14, wherein the response in step (c) is activation of NFκB and is measured by determining the level of cytokines production.

17. The method according to claim 16, wherein the cytokines are selected form the group consisting of IL-8, IL-6, and GM-CSF.

18. The method according to claim 17, wherein the level of cytokine production is determined using ELISA.

* * * * *